US012565639B2

(12) United States Patent
Tastad et al.

(10) Patent No.: US 12,565,639 B2
(45) Date of Patent: Mar. 3, 2026

(54) METHODS FOR DIFFERENTIATING DOPAMINERGIC NEURONS FROM STEM CELLS

(71) Applicant: Aspen Neuroscience, Inc., San Diego, CA (US)

(72) Inventors: David Tastad, San Diego, CA (US); Louisa Zebrowski, San Diego, CA (US); Ai Zhang, San Diego, CA (US); Branden Clark, San Diego, CA (US)

(73) Assignee: Aspen Neuroscience, Inc., San Diego, CA (US)

( * ) Notice: Subject to any disclaimer, the term of this patent is extended or adjusted under 35 U.S.C. 154(b) by 0 days.

(21) Appl. No.: 18/742,917

(22) Filed: Jun. 13, 2024

(65) Prior Publication Data

US 2024/0417683 A1 Dec. 19, 2024

Related U.S. Application Data

(60) Provisional application No. 63/472,789, filed on Jun. 13, 2023.

(51) Int. Cl.
*C12N 5/079* (2010.01)
*A01N 1/125* (2025.01)
*A61K 35/30* (2015.01)

(52) U.S. Cl.
CPC ........... *C12N 5/0618* (2013.01); *A01N 1/125* (2025.01); *A61K 35/30* (2013.01); *C12N 2500/38* (2013.01); *C12N 2500/40* (2013.01); *C12N 2501/13* (2013.01); *C12N 2501/15* (2013.01); *C12N 2501/155* (2013.01); *C12N 2501/16* (2013.01); *C12N 2501/41* (2013.01); *C12N 2501/42* (2013.01); *C12N 2501/727* (2013.01); *C12N 2506/45* (2013.01)

(58) Field of Classification Search
CPC .............. C12N 5/0618; C12N 2500/38; C12N 2500/40; C12N 2501/13; C12N 2501/15; C12N 2501/155; C12N 2501/16; C12N 2501/41; C12N 2501/42; C12N 2501/727; C12N 2506/45; A01N 1/0221; A61K 35/30
See application file for complete search history.

(56) References Cited

U.S. PATENT DOCUMENTS

| | | | | |
|---|---|---|---|---|
| 8,442,772 | B2 | 5/2013 | Loring | |
| 8,642,334 | B2 | 2/2014 | Chambers | |
| 9,453,198 | B2 | 9/2016 | Studer | |
| 10,260,041 | B2 | 4/2019 | Chambers | |
| 10,280,398 | B2 | 5/2019 | Studer | |
| 10,287,546 | B2 | 5/2019 | Chambers | |
| 10,711,243 | B2 | 7/2020 | Studer | |
| 10,828,335 | B2 | 11/2020 | George | |
| 11,236,302 | B2 | 2/2022 | Kirkeby | |
| 11,261,425 | B2 | 3/2022 | Takahashi | |
| 11,473,058 | B2 | 10/2022 | Takahashi | |
| 11,560,546 | B2 | 1/2023 | Chambers | |
| 2011/0118130 | A1 | 5/2011 | Loring | |
| 2015/0064139 | A1 | 3/2015 | Shoemaker | |
| 2015/0265652 | A1 | 9/2015 | George | |
| 2016/0201032 | A1 | 7/2016 | Studer | |
| 2017/0292112 | A1 | 10/2017 | Chang | |
| 2018/0094242 | A1* | 4/2018 | Studer | A61P 25/16 |
| 2018/0298326 | A1 | 10/2018 | Studer | |
| 2020/0407680 | A1 | 12/2020 | Studer | |
| 2021/0000929 | A1 | 1/2021 | Mason | |
| 2021/0123017 | A1 | 4/2021 | Ozaki | |
| 2021/0123018 | A1 | 4/2021 | Studer | |
| 2021/0292715 | A1 | 9/2021 | Schrepfer | |
| 2022/0177835 | A1 | 6/2022 | Studer | |
| 2022/0186180 | A1 | 6/2022 | Studer | |
| 2022/0254448 | A1 | 8/2022 | Loring | |
| 2023/0059010 | A1 | 2/2023 | Bratt-Leal | |
| 2023/0081881 | A1 | 3/2023 | Bratt-Leal | |
| 2023/0165909 | A1 | 6/2023 | Zhang | |

FOREIGN PATENT DOCUMENTS

| | | |
|---|---|---|
| CA | 3167713 | 7/2021 |
| EP | 3042951 | 7/2016 |
| EP | 3061809 | 8/2016 |
| EP | 3447130 | 2/2019 |
| WO | 2008132176 | 11/2008 |
| WO | 2011019092 | 2/2011 |

(Continued)

OTHER PUBLICATIONS

Precious et al. Dopaminergic Progenitors Derived From Epiblast Stem Cells Function Similarly to Primary VM-Derived Progenitors When Transplanted Into a Parkinson's Disease Model. Front Neurosci. Apr. 7, 2020:14:312. eCollection 2020 (Year: 2020).*
Bond et al. The Dynamic Role of Bone Morphogenetic Proteins in Neural Stem Cell Fate and Maturation. Dev Neurobiol. Jul. 2012; 72(7): 1068-1084. (Year: 2012).*
Jovanovic et al. BMP/SMAD Pathway Promotes Neurogenesis of Midbrain Dopaminergic Neurons In Vivo and in Human Induce Pluripotent and Neural Stem Cells. J Neurosci. Feb. 14, 2018; 38(7): 1662-1676. (Year: 2018).*
Chambers et al. Highly efficient neural conversion of human ES and iPS cells by dual inhibition of SMAD signaling. Nat Biotechnol. Mar. 2009;27(3):275-80. Epub Mar. 1, 2009. (Year: 2009).*
Cryoprotectant Definition. accessed at: https://wordshake.com/definition/cryoprotectant (Year: 2024).*
Kriks et al. Dopamine neurons derived from human ES cells efficiently engraft in animal models of Parkinson's disease. Nature. Nov. 6, 2011;480(7378):547-51. (Year: 2011).*

(Continued)

*Primary Examiner* — Valarie E Bertoglio
*Assistant Examiner* — Briana N Ebbinghaus
(74) *Attorney, Agent, or Firm* — Timothy L Smith

(57) ABSTRACT

The present disclosure provides methods of differentiating pluripotent stem cells, including induced pluripotent stem cells, into lineage-specific floor plate midbrain progenitor cells, determined dopaminergic neuronal progenitor cells, committed dopaminergic neuronal progenitor cells and/or dopaminergic neuronal cells. Also provided are compositions uses thereof, such as for treating neurodegenerative diseases and conditions, including Parkinson's disease, and articles of manufacture and kits for use thereof.

28 Claims, 9 Drawing Sheets

(56) References Cited

FOREIGN PATENT DOCUMENTS

| | | |
|---|---|---|
| WO | 2011149762 | 12/2011 |
| WO | 2013015457 | 1/2013 |
| WO | 2013067362 | 5/2013 |
| WO | 2015143342 | 9/2015 |
| WO | 2016162747 | 10/2016 |
| WO | 2017132596 | 8/2017 |
| WO | 2017160234 | 9/2017 |
| WO | 2019068854 | 4/2019 |
| WO | 2019111258 | 6/2019 |
| WO | 2021016607 | 1/2021 |
| WO | 2021081229 | 4/2021 |
| WO | 2021087145 | 5/2021 |
| WO | 2021146349 | 7/2021 |
| WO | 2021203009 | 10/2021 |
| WO | 2021216622 | 10/2021 |
| WO | 2021216623 | 10/2021 |
| WO | 2021216846 | 10/2021 |
| WO | 2021224496 | 11/2021 |
| WO | 2022062960 | 3/2022 |
| WO | 2022216911 | 10/2022 |
| WO | 2023004366 | 1/2023 |
| WO | 2023004370 | 1/2023 |
| WO | 2023004371 | 1/2023 |

OTHER PUBLICATIONS

Turksen. Bioreactors in Stem Cell Biology. Methods in Molecular Biology (2016) 1502; Published online: Feb. 3, 2016 (Year: 2016).*

Cell culture guidelines. Abcam. accessed at: https://web.archive.org/web/20180128010246/http://www.abcam.com/ps/pdf/protocols/cell_culture.pdf (Year: 2018).*

Cheng et al. CHIR99021 combined with retinoic acid promotes the differentiation of primordial germ cells from human embryonic stem cells. Oncotarget. Dec. 15, 2016;8(5):7814-7826. (Year: 2016).*

Arenas et al., "How to make a midbrain dopaminergic neuron," Development (2015) 142(11):1918-1936.

Kirkeby et al., "Generation of Regionally Specified Neural Progenitors and Functional Neurons from Human Embryonic Stem Cells under Defined Conditions," Cell Reports (2012) 1(6):703-714.

Lehnen et al., "IAP-Based Cell Sorting Results in Homogeneous Transplantable Dopaminergic Precursor Cells Derived from Human Pluripotent Stem Cells," Stem Cell Reports (2017) 9(4):1207-1220.

Liu et al., "Genome wide profiling of human embryonic stem cells (hESCs), their derivatives and embryonal carcinoma cells to develop base profiles of U.S. Federal government approved hESC lines," BMC Dev Biol (2006) 6:20.

Muller et al., "Regulatory networks define phenotypic classes of human stem cell lines," Nature (2008) 455:401-405.

Ninkovic et al., "The transcription factor Pax6 regulates survival of dopaminergic olfactory bulb neurons via crystallin αA, " Neuron (2010) 68(4):682-94.

Noisa et al., "Neural Progenitor Cells Derived from Human Embryonic Stem Cells as an Origin of Dopaminergic Neurons," Stem Cells Int (2015) 2015:647437.

Takahashi et al., "Induction of pluripotent stem cells from mouse embryonic and adult fibroblast cultures by defined factors," Cell (2006) 126(4):663-676.

Kirkeby Agnete et al, "Predictive Markers Guide Differentiation to Improve Graft Outcome in Clinical Translation of hESC-Based Therapy for Parkinson's Disease", Cell Stem Cell, Amsterdam, NL, (Jan. 1, 2017), vol. 20, No. 1, doi:10.1016/j.stem.2016.09.004, ISSN 1934-5909, pp. 135-148, XP055974965.

Arjona et al., "Autotransplantation of human carotid body cell aggregates for treatment of Parkinson's disease," Neurosurgery. (2003) 53(2):321-8.

Baden et al., "Insights into GBA Parkinson's disease pathology and therapy with induced pluripotent stem cell model systems," Neurobiol Dis. (2019), 127:1-12.

Lindvall et al., "Stem cells in human neurodegenerative disorders—time for clinical translation?" J Clin Invest. (2010) 120(1):29-40.

Reinhardt et al., "Genetic correction of a LRRK2 mutation in human iPSCs links parkinsonian neurodegeneration to ERK-dependent changes in gene expression," Cell Stem Cell (2013) 12(3):354-367.

Stepanichev, "Prospects for the Use of Genome-Editing Technology to Correct Neurodegenerative Diseases," Advances in Gerontology (2019) 9(2):154-163.

Ye et al., "FGF and Shh signals control dopaminergic and serotonergic cell fate in the anterior neural plate," Cell. (1998) 93(5):755-66.

Yu et al., "Human induced pluripotent stem cells free of vector and transgene sequences," Science (2009) 324 (5928):797-801.

Kim et al., "Neural stem cells derived from human midbrain organoids as a stable source for treating Parkinson's disease Midbrain organoid-NSCs (Og-NSC) as a stable source for PD treatment," Progress in Neurobiology (2021) 204:102086.

Tsuji et al., "Genetic heterogeneity in type 1 Gaucher disease: multiple genotypes in Ashkenazic and non-Ashkenazic individuals," Proceedings of the National Academy of Sciences (1988) 85(7):2349-2352.

Vakulskas et al., "A high-fidelity Cas9 mutant delivered as a ribonucleoprotein complex enables efficient gene editing in human hematopoietic stem and progenitor cells," Nature Medicine (2018) 24(8):1216-1224.

Velez-Pardo et al., "The distribution and risk effect of GBA variants in a large cohort of PD patients from Colombia and Peru," Parkinsonism & Related Disorders (2019) 63:204-208.

Vetchinova et al., "Cytogenetic analysis of the results of genome editing on the cell model of Parkinson's disease," Bulletin of Experimental Biology and Medicine (2018) 165(3):378-381.

Tieng et al., "Engineering of midbrain organoids containing long-lived dopaminergic neurons," Stem Cells and Development (2014) 23(13):1535-1547.

Takahashi, "Strategies for bringing stem cell-derived dopamine neurons to the clinic: The Kyoto trial," Prog Brain Res. (2017) 230:213-226.

Piccini et al., "Dopamine release from nigral transplants visualized in vivo in a Parkinson's patient," Nat Neurosci. (1999) 2(12):1137-40.

Raikwar et al., "Next generation precision medicine: CRISPR-mediated genome editing for the treatment of neurodegenerative disorders," Journal of Neuroimmune Pharmacology (2019) 14(4):608-641.

Tabar et al., "Therapeutic cloning in individual parkinsonian mice," Nat Med. (2008) 14(4):379-81.

Smits et al., "Modeling Parkinson's disease in midbrain-like organoids," NPJ Parkinson's Disease (2019) 5(1):1-8.

Romito et al., "Pluripotent Stem Cells: Current Understanding and Future Directions," Stem Cells Int. (2016) 2016:9451492, 20 pages.

Sanders et al., "LRRK2 mutations cause mitochondrial DNA damage in iPSC-derived neural cells from Parkinson's disease patients: reversal by gene correction," Neurobiology of Disease (2014) 62:381-386.

Sison et al., "Using patient-derived induced pluripotent stem cells to identify Parkinson's disease-relevant phenotypes," Current Neurology and Neuroscience Reports (2018) 18(12):1-14.

Badger et al., "Parkinson's disease in a dish—Using stem cells as a molecular tool," Neuropharmacology (2014) 76:88-96.

Bain et al., "Embryonic stem cells express neuronal properties in vitro," Dev Biol. (1995) 168(2):342-57.

Bakay et al., "Implantation of Spheramine in advanced Parkinson's disease (PD)," Front Biosci. (2004) 9:592-602.

Berge-Seidl et al., "The GBA variant E326K is associated with Parkinson's disease and explains a genome-wide association signal," Neuroscience Letters (2017) 658:48-52.

Bjorklund et al., "Neural transplantation for the treatment of Parkinson's disease," Lancet Neurol. (2003) 2(7):437-45.

Brundin et al., "Neural grafting in Parkinson's disease Problems and possibilities," Prog Brain Res. (2010) 184:265-94.

Brunet et al., "Metagenes and molecular pattern discovery using matrix factorization," Proceedings of the National Academy of Sciences (2004) 101(12):4164-4169.

Cyranoski, "'Reprogrammed' stem cells implanted into patient with Parkinson's disease," Nature. (2018) doi: https://doi.org/10.1038/d41586-018-07407-9.

(56) References Cited

OTHER PUBLICATIONS

Deng et al., "The genetics of Parkinson disease," Ageing Research Reviews (2018) 42:72-85.
Doi et al., "Isolation of human induced pluripotent stem cell-derived dopaminergic progenitors by cell sorting for successful transplantation," Stem Cell Reports (2014) 2(3):337-50.
Fitzpatrick et al., "Cell-based therapies for Parkinson's disease: past, present, and future," Antioxid Redox Signal. (2009) 11(9):2189-2208.
Ghatak et al., "Parkinson's disease: what the model systems have taught us so far," Journal of Genetics (2018) 97(3):729-751.
Han et al., "Generation of hypoimmunogenic human pluripotent stem cells," Proc Natl Acad Sci USA. (2019) 116 (21):10441-10446.
Heijer et al., "A Large-Scale Full GBA1 Gene Screening in Parkinson's Disease in the Netherlands," Mov Disord. (2020) 35(9):1667-1674.
Kan et al., "Dopaminergic differentiation of human mesenchymal stem cells—utilization of bioassay for tyrosine hydroxylase expression," Neurosci Lett (2007) 419(1):28-33.
Kawaguchi et al., "Single-cell gene profiling defines differential progenitor subclasses in mammalian neurogenesis," Development (2008) 135(18):3113-24.
Kim et al., "miR-371-3 expression predicts neural differentiation propensity in human pluripotent stem cells," Cell Stem Cell (2011) 8(6):695-706.
Kordower et al., "Neuropathological evidence of graft survival and striatal reinnervation after the transplantation of fetal mesencephalic tissue in a patient with Parkinson's disease," N Engl J Med. (1995) 332(17):1118-24.
Kriks et al., "Floor plate-derived dopamine neurons from hESCs efficiently engraft in animal models of PD," Nature (2011) 480(7378):547-51.
Lee et al., "Efficient generation of midbrain and hindbrain neurons from mouse embryonic stem cells," Nat Biotechnol. (2000) 18(6):675-9.
Madrazo et al., "Open microsurgical autograft of adrenal medulla to the right caudate nucleus in two patients with intractable Parkinson's disease," N Engl J Med. (1987) 316(14):831-4.
Martinez-Cerdeno et al., "Neural Progenitor Cell Terminology," Front Neuroanat (2018) 12:104.
Mendez et al., I., "Dopamine neurons implanted into people with Parkinson's disease survive without pathology for 14 years," Nat Med (2008) 14(5):507-509.
Nowrousian et al., "Next-generation sequencing techniques for eukaryotic microorganisms: sequencing-based solutions to biological problems," Eukaryot Cell. (2010) 9(9):1300-10.
Ochalek et al., "Generation of Cholinergic and Dopaminergic Interneurons from Human Pluripotent Stem Cells as a Relevant Tool for In Vitro Modeling of Neurological Disorders Pathology and Therapy," Stem Cells Int. (2016) 5838934:1-16.
Okabe et al., "Development of neuronal precursor cells and functional postmitotic neurons from embryonic stem cells in vitro," Mech Dev. (1996) 59(1):89-102.
Okamoto et al., "Highly efficient genome editing for single-base substitutions using optimized ssODNs with Cas9-RNPs," Scientific Reports (2019) 9(1):1-11.
Paix et al., "Precision genome editing using CRISPR-Cas9 and linear repair templates in C. elegans," Methods (2017) 121-122:86-93.
Vallier et al., "Signaling pathways controlling pluripotency and early cell fate decisions of human induced pluripotent stem cells," Stem Cells (2009) 27: 2655-2666.
Lavaute et al., "Regulation of Neural specification from human embryonic stem cells by BMP and FGF," Stem Cells (2009) 27: 1741-1749.
Patani et al., "Activin/Nodal inhibition alone accelerates highly efficient neural conversion from human embryonic stem cells and imposes a caudal positional identity," PlosOne (2009) 4:e7327.
Cuny et al., "Structure-activity relationship study of bone morphogenetic protein (BMP) signaling inhibitors," Bioorg & Medicinal Chemistry Letters (2008) 18: 4388-4392.
Hu et al., "Neural differentiation of human induced pluripotent stem cells follows developmental principles but with variable potency," Proc. Nat'l. Acad. Sci USA (2010) 9: 4335-4340.
Lamb et al., "Fibroblast growth factor is a direct neuronal inducer, which combined with noggin generates anterior-posterior neural pattern," Development (1995) 121: 3627-3636.
International Preliminary Report on Patentability for PCT/US2021/013324, Aspen Neuroscience, Inc., filed Jan. 13, 2021, dated Jul. 19, 2022.
European Patent Office Decision to Grant dated Jun. 5, 2024.
European Patent Office Communication pursuant to Article 94(3) EPC dated Nov. 27, 2023.

* cited by examiner

Non-Adherent Differentiation Method

BAGCT/DAPT = BDNF, GDNF, ascorbic acid, dbcAMP and TGFβ3

Figure 3A
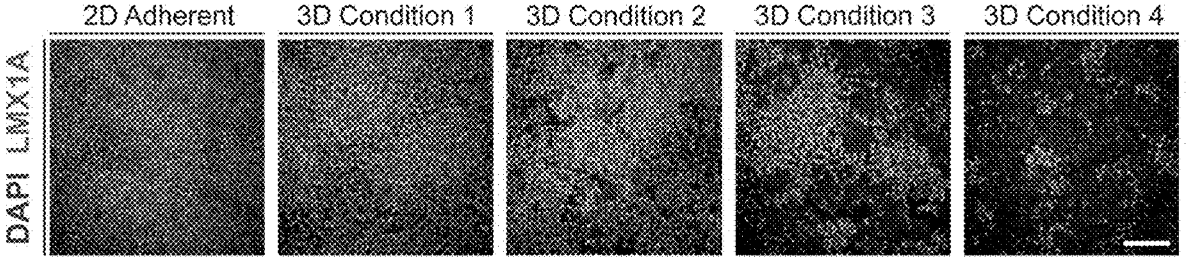
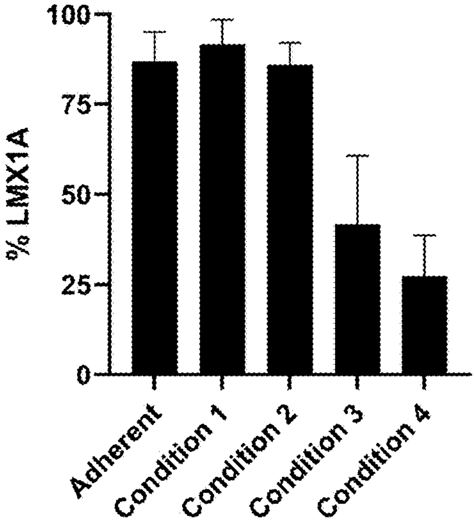
Figure 3B

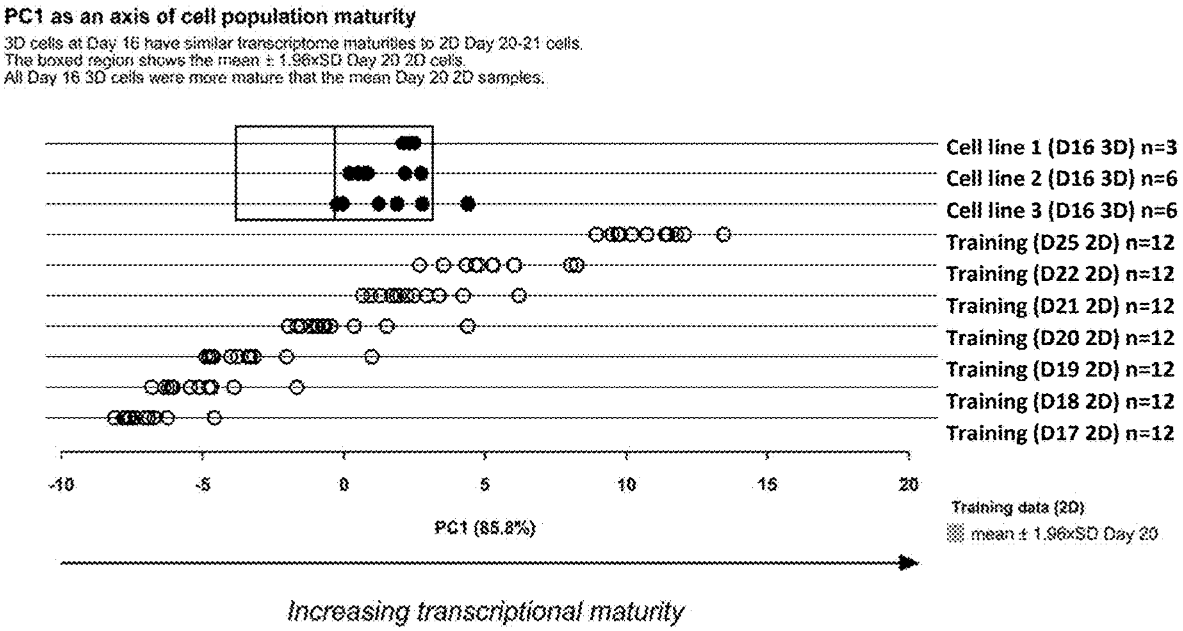

Figure 4

PC1 as an axis of cell population maturity

3D cells at Day 16 have similar transcriptome maturities to 2D Day 20-21 cells.
The boxed region shows the mean ± 1.96×SD Day 20 2D cells.
All Day 16 3D cells were more mature that the mean Day 20 2D samples.

Cell line 1 (D16 3D) n=3
Cell line 2 (D16 3D) n=6
Cell line 3 (D16 3D) n=6
Training (D25 2D) n=12
Training (D22 2D) n=12
Training (D21 2D) n=12
Training (D20 2D) n=12
Training (D19 2D) n=12
Training (D18 2D) n=12
Training (D17 2D) n=12

-10          -5          0          5          10          15          20

PC1 (85.8%)

Training data (2D)
mean ± 1.96×SD Day 20

*Increasing transcriptional maturity*

METHODS FOR DIFFERENTIATING DOPAMINERGIC NEURONS FROM STEM CELLS

CROSS-REFERENCE TO RELATED APPLICATIONS

This application claims priority to U.S. Provisional Application No. 63/472,789, filed Jun. 13, 2023, entitled "METHODS FOR DIFFERENTIATING DOPAMINERGIC NEURONS FROM STEM CELLS," the contents of which are incorporated herein by reference in its entirety for all purposes.

FIELD

The present disclosure relates to methods of differentiating pluripotent stem cells, including induced pluripotent stem cells, into lineage-specific floor plate midbrain progenitor cells, determined dopaminergic neuronal progenitor cells, committed dopaminergic neuronal progenitor cells and/or dopaminergic neuronal cells. Also provided are compositions of the differentiated cells and therapeutic uses thereof, such as for treating neurodegenerative conditions and diseases, including Parkinson's disease, and articles of manufacture and kits thereof.

BACKGROUND

Parkinson's Disease leads to debilitating motor complications and currently no restorative treatments are available. Parkinson's disease trails only Alzheimer's disease as the most common neurodegenerative disorder, affecting about 0.3% of the general population and 1-2% of the population over age 65. The prevalence of PD is expected to double or triple as the developed world population ages. Cha et al. (2023) *J. Mov. Disord.* 16:22-41; Rong et al. (2021) *Neurology* 97: e1986-e1993; Dorsey and Bloem (2018) *JAMA Neurol.* 75:9-10; de Lau and Breteler (2006) *Lancet Neurol.* 5:525-535.

Dopamine deficiency resulting from progressive loss of dopaminergic neurons in the substantia nigra is a common characteristic of PD. By the time of diagnosis, patients have already experienced significant nigrostriatal degeneration. Currently available treatments, such as dopamine replacement therapy (e.g., with L-dopa or dopamine agonists) benefit some patients, but have a limited therapeutic window due to side effects and decreasing efficacy. Cha et al., Weiss et al. (1971) *Lancet.* 1:1016-1017; Kang and Fahn (1988) *Ration. Drug Ther.* 22: 1-7.

Cell replacement therapies that aim to restore lost dopamine producing neurons have been in development for many years. A challenge in developing a cell-based therapy for Parkinson's Disease (PD) has been the identification of an appropriate cell source for use in neuronal replacement. One approach was the transplantation of fetal midbrain DA neurons, such as was performed in over 300 patients worldwide. Brundin et al., *Prog. Brain Res.* (2010) 184:265-94; Lindvall, & Kokaia, *J. Clin. Invest* (2010) 120:29-40. Therapy using human fetal tissue in these patients demonstrated evidence of DA neuron survival and in vivo DA release up to 10 or 20 years after transplantation in some patients. In many patients, though, fetal tissue transplantation fails to replace DA neuronal function. Moreover, Parkinson's disease patients who were treated with fetal cell transplants sometimes experience off-medication graft-induced dyskinesias. Evidence demonstrates that this serious side effect is caused by serotonin (5-HT) that is produced by the transplanted fetal cells. Politis et al., *Mov. Disord.* (2011) 26: 1997-2003. Further, fetal tissue transplantation is plagued by challenges including low quantity and quality of donor tissue, ethical and practical issues surrounding tissue acquisition, and the poorly defined heterogeneous nature of transplanted cells, which are some of the other factors contributing to the variable clinical outcomes. Mendez et al., *Nature Med.* (2008); Kordower et al., *N. Engl. J. Med.* (1995) 332:1118-24; and Piccini et al., *Nature Neuroscience* (1999) 2:1137-40. Hypotheses as to the limited efficacy observed in the human fetal grafting trials include that fetal grafting may not provide a sufficient number of cells at the correct developmental stage and that fetal tissue is quite poorly defined by cell type and variable with regard to the stage and quality of each tissue sample. Bjorklund et al., *Lancet Neurol.* (2003) 2:437-45. A further contributing factor may be inflammatory host response to the graft. Id.

Another approach is to use stem cell-derived cells, such as pluripotent stem cells (PSCs) as a source of cells for applications in regenerative medicine. Pluripotent stem cells have the ability to undergo self-renewal and give rise to all cells of the issues of the body. PSCs include two broad categories of cells: embryonic stem (ES) cells and induced pluripotent stem cells (iPSCs). ES cells are derived from the inner cell mass of preimplantation embryos and can be maintained indefinitely and expanded in their pluripotent state in vitro. Romito and Cobellis, *Stem Cells Int.* (2016) 2016:9451492. Recently, preliminary results were reported for a phase I clinical trial that involved implanting dopaminergic neuronal cells obtained by differentiation of ES cells into the brains of patients with Parkinson's disease (2023 International Congress of Parkinson's Disease and Movement Disorders, held August 27-31 in Copenhagen, Denmark). The results showed that the strategy was well tolerated, with no serious adverse effects related to the treatment. Preliminary efficacy data indicated improvements in motor functions. Despite these advances, the use of embryonic stem cells is plagued by ethical concerns, as well as the possibility that such cells may form tumors in patients. Finally, ES cell-derived transplants may cause immune reactions in patients in the context of allogeneic stem cell transplant.

The use of induced pluripotent stem cells (iPSCs), rather than ES-derived cells, has the advantages of avoiding ethical concerns. Further, derivation of iPSCs from a patient to be treated (i.e., the patient receives an autologous cell transplant) avoids risks of immune rejection inherent in the use of embryonic stem cells. iPSCs can be obtained by reprogramming ("dedifferentiating") adult somatic cells to become more ES cell-like, including having the ability to expand indefinitely and differentiate into all three germ layers. Id. Such reprogramming is often accomplished using the "Yamanaka factors. (Oct 3/4, Sox2, Klf4, and a Myc family member). See, e.g., U.S. Pat. No. 8,530,238.

Various methods for differentiating pluripotent stem cells into lineage specific cell populations and the resulting cellular compositions are contemplated to find use in cell replacement therapies for patients with diseases resulting in a loss of function of a defined cell population. However, in some cases, such methods are limited in their ability to produce cells with consistent physiological characteristics, and cells resulting from such methods may be limited in their ability to engraft and innervate other cells in vivo. As an example, neural cells obtained by differentiation from pluripotent stem cells may be more amenable to engraftment into the brain of a subject undergoing treatment when the neural cells are at an intermediate stage between earlier stages (e.g., that of precursor or progenitor cells) and later stages (e.g., that of differentiated cells). Moreover, there is a need for improving the manufacturability of lineage-specific cell populations, e.g., for therapeutic purposes, that are derived from pluripotent stem cells, such as by reducing the time and/or resources, including cost, required for such manufacturing. Accordingly, improved methods and cellular compositions thereof are needed. The present invention fulfils these and other needs.

SUMMARY OF THE INVENTION

The invention provides, in some embodiments, methods of differentiating pluripotent stem cells into dopaminergic neuronal progenitor cells. In some embodiments, the methods involve: (a) performing a first incubation comprising non-adherently culturing pluripotent stem cells in a first culture vessel under conditions to produce a cellular spheroid, wherein the first incubation comprises: (i) exposing the pluripotent stem cells to at least one inhibitor of TGF-β/activin-Nodal signaling and at least one inhibitor of bone morphogenetic protein (BMP) signaling for at least one day (Day 0) in the absence of: x) an activator of Sonic Hedgehog (SHH) signaling, and y) an inhibitor of glycogen synthase kinase 3β (GSK3β) signaling; and (ii) starting on the second day (Day 1) of the first incubation, exposing the pluripotent stem cells to at least one activator of Sonic Hedgehog (SHH) signaling and at least one inhibitor of glycogen synthase kinase 3β (GSK3β) signaling; and (b) performing a second incubation that includes adherently culturing cells of the spheroid in a second culture vessel under conditions to further differentiate the cells into dopaminergic neuronal progenitor cells.

In some embodiments, the dopaminergic neuronal progenitor cells are determined dopaminergic neuronal progenitor cells. In some embodiments, the pluripotent stem cells are induced pluripotent stem cells. In some embodiments, the pluripotent stem cells are autologous to a subject to be treated with the dopaminergic neuronal progenitor cells.

In some embodiments, the first incubation further includes exposing the pluripotent stem cells to a ROCK inhibitor (ROCKi) starting on Day 0. In some embodiments, the pluripotent stem cells were not exposed to a ROCKi prior to exposing the pluripotent stem cells to the inhibitor of TGF-β/activin-Nodal signaling and the inhibitor of bone morphogenetic protein (BMP) signaling in the first incubation.

In some embodiments, the method involves exposing the pluripotent stem cells to: (a) the inhibitor of TGF-β/activin-Nodal signaling beginning on Day 0 and through Day 4; (b) the inhibitor of BMP signaling beginning on Day 0 and through Day 10; (c) the activator of Sonic Hedgehog signaling beginning on Day 1 and through Day 6; and (d) the inhibitor of glycogen synthase kinase 3β (GSK3β) signaling beginning on Day 1 and through Day 12.

In some embodiments, the inhibitor of BMP signaling is LDN193189. In some embodiments, the cells are exposed to LDN193189 at a concentration of between about 10 nM and 500 nM, between about 20 nM and about 400 nM, between about 50 nM and about 200 nM, or between about 75 nM and about 150 nM, optionally about 100 nM.

In some embodiments, the inhibitor of TGF-β/activin-Nodal signaling is SB431542. In some embodiments, the cells are exposed to SB431542 at a concentration of between about 1 μM and about 20 μM, between about 5 μM and about 15 μM, or between about 8 μM and about 12 μM, optionally about 10 μM.

In some embodiments, the activator of SHH signaling is SHH or purmorphamine. In some embodiments, the cells are exposed to SHH at a concentration of between about 10 ng/mL and 500 ng/mL, between about 20 ng/mL and about 400 ng/mL, between about 50 ng/mL and about 200 ng/mL, or between about 75 ng/mL and about 150 ng/mL, optionally about 100 ng/mL. In some embodiments, the cells are exposed to purmorphamine at a concentration of between about 0.1 μM and about 20 μM, between about 0.5 μM and about 10 μM, between about 1 μM and about 5 μM, between about 1 μM and about 3 μM, or between about 1.5 μM and about 2.5 μM, optionally at about 2 μM.

In some embodiments, the inhibitor of GSK3β signaling is CHIR99021. In some embodiments, the cells are exposed to CHIR99021 at a concentration of between about 0.1 μM and about 5 μM, between about 0.5 μM and about 4 μM, between about 0.5 μM and about 2 μM, optionally about 1 μM; and on each of Days 2 through 12, the cells are exposed to CHIR99021 at a concentration of between about 0.1 μM and about 5 μM, between about 0.5 μM and about 4 μM, or between about 1 μM and about 3 μM, optionally about 2 μM.

In some embodiments, the first incubation includes a media exchange on one or more of Days 1 through 6. In some embodiments, the first incubation comprises a media exchange on each of Days 1 through 6. In some embodiments, the media exchange comprises replacing at or about 50% of the media. In some embodiments, the media exchange comprises replacing all or nearly all of the media.

In some embodiments, the second incubation begins on or about Day 7. In some embodiments, the cells of the spheroid are disassociated prior to the second incubation to form a cell suspension. In some embodiments, the dissociating is carried out at a time when the spheroid cells express at least one of PAX6 and OTX2. In some embodiments, the dissociating is carried out on about Day 7. In some embodiments, the second incubation involves adherently culturing the cell suspension in the second cell culture vessel.

In some embodiments, the second incubation includes exposing the cells of the spheroid to an inhibitor of bone morphogenetic protein (BMP) signaling and an inhibitor of GSK3β signaling. In some embodiments, the second incubation the second incubation further comprises exposing the cells to (i) brain-derived neurotrophic factor (BDNF); (ii) ascorbic acid; (iii) glial cell-derived neurotrophic factor (GDNF); (iv) dibutyryl cyclic AMP (dbcAMP); (v) transforming growth factor beta-3 (TGFβ3) (collectively, "BAGCT"); and (vi) an inhibitor of Notch signaling. In some embodiments, the cells are exposed to BAGCT and the inhibitor of Notch signaling beginning on Day 11. In some embodiments, the cells are exposed to BAGCT and the inhibitor of Notch signaling beginning at Day 11 and until harvest of the dopaminergic neuronal progenitor cells, optionally until Day 14, Day 15, Day 16, or Day 17.

In some embodiments, the second incubation comprises a media exchange on one or more of Days 7 through harvest or collection. In some embodiments, the second incubation comprises a media exchange on each of Days 7 through harvest or collection. In some embodiments, the media exchange on one or more of Days 7 through harvest comprises replacing at least 90%, 91%, 92%, 93%, 94%, 95%, 96%, 97%, 98%, or 99% of the media. In some embodiments, about or at least about 50% of the media is replaced on Days 1, 2, 3, 4, 5, and 6. In some embodiments, about 50% of the media is replaced on Days 1, 2, 3, 4, 5, and 6.

In some embodiments, all or nearly all of the media is replaced in the media exchange.

In some embodiments, the method further includes harvesting the dopaminergic neuronal progenitor cells. In some embodiments, the dopaminergic neuronal progenitor cells are harvested on Day 14 or later. In some embodiments, the dopaminergic neuronal progenitor cells are harvested between Day 14 and Day 17.

In some embodiments, the method further includes formulating the harvested dopaminergic neuronal progenitor cells with a cryoprotectant. In some embodiments, the cryoprotectant is selected from among the group consisting of: glycerol, propylene glycol, and dimethyl sulfoxide (DMSO). In some embodiments, the method further comprises cryopreserving the formulated harvested dopaminergic neuronal progenitor cells, and optionally thawing the cells prior to use. In some embodiments, the cryopreserving comprises controlled rate freezing.

In some embodiments, provided herein are therapeutic compositions that contain dopaminergic neuronal progenitor cells produced using a method that involves: (a) performing a first incubation comprising non-adherently culturing pluripotent stem cells in a first culture vessel under conditions to produce a cellular spheroid, wherein the first incubation comprises: (i) exposing the pluripotent stem cells to at least one inhibitor of TGF-β/activin-Nodal signaling and at least one inhibitor of bone morphogenetic protein (BMP) signaling for at least one day (Day 0) in the absence of: x) an activator of Sonic Hedgehog (SHH) signaling, and y) an inhibitor of glycogen synthase kinase 3β (GSK3β) signaling; and (ii) starting on the second day (Day 1) of the first incubation, exposing the pluripotent stem cells to at least one activator of Sonic Hedgehog (SHH) signaling and an inhibitor of glycogen synthase kinase 3β (GSK3β) signaling; and (b) performing a second incubation comprising adherently culturing cells of the spheroid in a second culture vessel under conditions to further differentiate the cells into dopaminergic neuronal progenitor cells.

In some embodiments, the therapeutic compositions provided herein include dopaminergic neuronal progenitor cells that, compared to neuronal cells produced using an adherent culture differentiation method, exhibit one or more properties selected from the group consisting of: (a) expressing a higher level of FOXA2; (b) expressing a lower level of PAX6; (c) having a higher predicted graft size after implantation; (d) having a higher predicted dopamine production level after implantation; (e) producing less serotonin; (f) comprising a higher percentage of viable cells; (g) expressing a higher level of CORIN; (h) expressing a lower level of PITX2; and (i) expressing a lower level of NKX2.1. In some embodiments, the cells of the therapeutic compositions exhibit two or more of these properties. In some embodiments, the cells exhibit three, four, five, six, seven, or eight or more of these properties. In some embodiments, the cells exhibit all nine of the listed properties.

In some embodiments, the therapeutic compositions provided herein include dopaminergic neuronal progenitor cells that exhibit one or more properties selected from the group consisting of: (a) produce serotonin at a level of less than 2 nM and increases less than two-fold when stimulated with KCl compared to unstimulated baseline; (b) more than 90% of the dopaminergic neuronal progenitor cells in the composition are viable; (c) express FOXA2 at greater than 100 TPM in bulk RNAseq analysis; (d) express CORIN at greater than 300 TPM in bulk RNAseq analysis; (e) express PITX2 at less than 50 TPM in bulk RNAseq analysis; (f) express NKX2.1 at less than 10 TPM in bulk RNAseq analysis; (g) greater than 90% FOXA2 positive cells; and (h) have a GraftTest™ score that is at least 1500. In some embodiments, the cells of the therapeutic compositions exhibit two or more of properties listed in this paragraph. In some embodiments, the cells exhibit three, four, five, six, or seven or more of these properties. In some embodiments, the cells exhibit all eight of the listed properties.

In some embodiments, the dopaminergic neuronal progenitor cells are determined dopaminergic neuron progenitor cells. In some embodiments, the dopaminergic neuronal progenitor cells are committed dopaminergic neuronal progenitor cells. In some embodiments, the dopaminergic neuronal progenitor cells are capable of innervating host tissue upon transplantation into a subject.

In some embodiments, the culture is performed in a microwell container. In these embodiments, the number of PSCs introduced into microwell container on Day 0 of the method is between about 100 pluripotent stem cells per well and about 5,000 pluripotent stem cells per well. In some embodiments, the number of pluripotent stem cells per well is between about 250 and 3,000, and in some embodiments, the number of PSCs introduced into the microwell container is between about 500 and 1,000 cells per microwell.

In some embodiments, the culture of pluripotent stem cells on Day 0 comprises a number of cells sufficient to produce a spheroid on about Day 7 comprising between about 1,000 cells and about 9,000 cells, or between about 2,000 cells and about 5,000 cells. In some embodiments, the culture of pluripotent stem cells on Day 0 comprises a number of cells sufficient to produce a spheroid on about Day 7 comprising about 2,000 cells. In some embodiments, the culture of pluripotent stem cells on Day 0 comprises a number of cells sufficient to produce a spheroid on about Day 7 comprising about 3,000 cells.

In some embodiments, the cells are exposed to an inhibitor of Rho-associated protein kinase (ROCK) signaling on Day 0 and/or Day 7. In some embodiments, the cells are exposed to an inhibitor of Rho-associated kinase protein (ROCK) signaling on Day 0 and Day 7. In some embodiments, the ROCK inhibitor is Y-27632. In some embodiments, the cells are exposed to the ROCK inhibitor at a concentration of between about 1 μM and about 20 μM, between about 5 μM and about 15 μM, or between about 8 μM and about 12 μM, optionally about 10 μM. In some embodiments, the pluripotent stem cells are not exposed to a ROCKi prior to exposing the pluripotent stem cells to the inhibitor of TGF-β/activin-Nodal signaling and the inhibitor of bone morphogenetic protein (BMP) signaling in the first incubation.

In some embodiments, the pluripotent stem cells are embryonic stem (ES) cells, induced pluripotent stem cells (iPSCs), or a combination thereof. In some embodiments, the pluripotent stem cells are embryonic stem (ES) cells, optionally mouse or human embryonic stem cells. In some embodiments, the pluripotent stem cells are human embryonic stem cells. In some embodiments, the pluripotent stem cells are induced pluripotent stem cells, optionally mouse or human induced pluripotent stem cells. In some embodiments, the pluripotent stem cells are human induced pluripotent stem cells.

In some embodiments, the pluripotent stem cells are autologous to a subject to be treated with the neurally differentiated cells. In some embodiments, the pluripotent stem cells are allogeneic to a subject to be treated with the dopaminergic neuronal progenitor cells.

In some embodiments, the pluripotent stem cells are from a healthy human subject. In some embodiments, the pluripotent stem cells are from a human subject with a neurodegenerative disease or condition. In some embodiments, the neurodegenerative disease or condition comprises the loss of dopaminergic neurons. In some embodiments, the neurodegenerative disease or condition is a Parkinsonism. In some embodiments, the neurodegenerative disease or condition is Parkinson's disease.

Also provided herein is a therapeutic composition comprising dopaminergic neuronal progenitor cells produced by any of the methods disclosed herein. In some embodiments, the therapeutic composition comprises dopaminergic neuronal progenitor cells produced by a method that includes: a) performing a first incubation that includes non-adherently culturing pluripotent stem cells in a first culture vessel under conditions to produce a cellular spheroid, wherein the first incubation includes: (i) starting on the first day (Day 0) of the first incubation, exposing the pluripotent stem cells to an inhibitor of TGF-β/activin-Nodal signaling and an inhibitor of bone morphogenetic protein (BMP) signaling in the absence of: x) an activator of Sonic Hedgehog (SHH) signaling, and y) an inhibitor of glycogen synthase kinase 3β (GSK3β) signaling; and (ii) starting on the second day (Day 1) of the first incubation, exposing the pluripotent stem cells to at least one activator of Sonic Hedgehog (SHH) signaling and an inhibitor of glycogen synthase kinase 3β (GSK3β) signaling; and (b) performing a second incubation that includes adherently culturing cells of the spheroid in a second culture vessel under conditions to further differentiate the cells into dopaminergic neuronal progenitor cells.

In some embodiments, the therapeutic composition includes dopaminergic neuronal progenitor cells that, compared to neuronal cells produced using an adherent culture differentiation method, exhibit one or more properties selected from the group consisting of: (a) expressing a higher level of FOXA2; (b) expressing a lower level of PAX6; (c) having a higher predicted graft size after implantation; (d) having a higher predicted dopamine production level after implantation; (e) producing less serotonin; (f) including a higher percentage of viable cells; (g) expressing a higher level of CORIN; (h) expressing a lower level of PITX2; and (i) expressing a lower level of NKX2.1.

In some embodiments, the dopaminergic neuronal progenitor cells are capable of engrafting and innervating other cells in vivo.

In some embodiments, the dopaminergic neuronal progenitor cells are capable of producing dopamine after administration to a subject and subsequent engraftment, optionally wherein the determined cells do not produce or do not substantially produce norepinephrine. In some embodiments, the cells do not produce or do not substantially produce serotonin.

In some embodiments, at least about 70%, 75%, 80%, 85%, 90%, or 95% of the total cells in the therapeutic composition are viable.

In some embodiments, the therapeutic composition comprises a cryoprotectant. In some embodiments, the cryoprotectant is selected from among the group consisting of: glycerol, propylene glycol, and dimethyl sulfoxide (DMSO).

Also provided herein is a population of differentiated neural cells produced by any of the methods disclosed herein.

Also provided herein is a therapeutic composition comprising any population of differentiated neural cells disclosed herein.

Also provided herein is a method of treatment, comprising administering to a subject in need thereof a therapeutically effective amount of any of the therapeutic compositions disclosed herein.

Also provided herein is a use of any of the compositions disclosed herein for manufacture of a medicament for treating a subject having a neurodegenerative disease or condition.

Also provided herein is any of the pharmaceutical compositions disclosed herein for use in treating a subject having a neurodegenerative disease or condition.

In some embodiments, the neurodegenerative disease or condition comprises the loss of dopaminergic neurons. In some embodiments, the subject has lost at least 50%, at least 60%, at least 70%, or at least 80% of dopaminergic neurons, optionally in the substantia nigra (SN), optionally in the SN *pars compacta* (SNc). In some embodiments, the neurodegenerative disease or condition is Parkinsonism. In some embodiments, the neurodegenerative disease or condition is Parkinson's disease, optionally idiopathic Parkinson's disease. In some embodiments, the cells of the composition are autologous to the subject. In some embodiments, the cells of the composition are allogeneic to the subject.

BRIEF DESCRIPTION OF THE DRAWINGS

FIG. 3A shows LMX1A and DAPI expression on cells cultured using each of the following methods: 2D adherent culture, 3D Condition 1, 3D Condition 2, 3D Condition 3, and 3D Condition 4. FIG. 3B shows a graph quantifying the percentage of LMX1A expressing cells in the cells from three cell lines cultured using each of the following methods: 2D adherent culture, 3D Condition 1, 3D Condition 2, 3D Condition 3, and 3D Condition 4.

FIG. 4 shows relative transcriptome maturity using a principal component analysis (PCA) using a training set based on the 2D adherent culture method and a test set being the non-adherent 3D culture method as described in Example 1. PC1 (x-axis) is the proxy of transcriptome maturity during differentiation, with lower values corresponding with earlier differentiation timepoints and higher values corresponding with later differentiation timepoints. The n=12 samples across seven training set time points are shown in the lowermost seven rows while the 3D-differentiated test sets are shown in the top three rows. The test set data are ranked by their mean PC1 value. The shaded box shows the mean±1.96×SD of the PC1 scores of Day 20 2D-differentiated samples.

DETAILED DESCRIPTION

Figure 1:
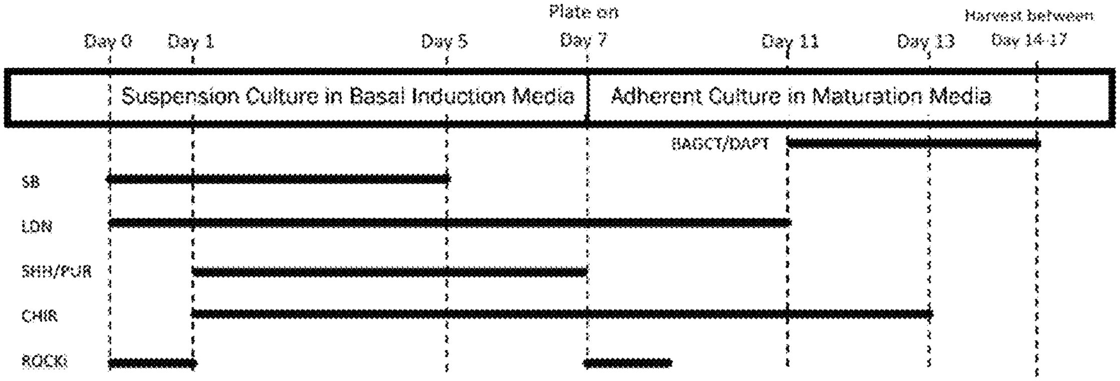
FIG. 1. shows an exemplary non-adherent protocol for the differentiation of pluripotent stem cells into dopaminergic neuronal progenitor cells, determined dopaminergic neuronal progenitor cells, committed dopaminergic neuronal progenitor cells or dopaminergic neuronal cells.

The present disclosure relates to methods of lineage-specific differentiation of pluripotent stem cells (PSCs), such as embryonic stem (ES) cells or induced pluripotent stem cells (iPSCs). Specifically provided are methods of directing lineage specific differentiation of PSCs or iPSCs into floor plate midbrain progenitor cells, dopaminergic neuronal progenitor cells, determined dopaminergic neuronal progenitor cells (DDPCs), committed dopaminergic neuronal progenitor cells and/or dopaminergic neuronal cells. The differentiated cells made using the methods provided herein are further contemplated for various uses including, but not limited to, use as a therapeutic to reverse disease of, or damage to, a lack of dopamine-producing neurons in a patient.

Provided herein are methods for lineage specific differentiation of pluripotent stem cells (PSCs), such as embryonic stem (ES) cells or induced pluripotent stem cells (iPSCs) into floor plate midbrain progenitor cells, dopaminergic neuronal progenitor cells, including determined dopaminergic neuronal progenitor cells, and/or dopaminergic neuronal cells. In some aspects, PSCs are differentiated into floor plate midbrain progenitor cells. In some aspects, such floor plate midbrain progenitor cells are further differentiated into dopaminergic neuronal progenitor cells, including determined dopaminergic neuronal progenitor cells. In some embodiments, determined dopaminergic progenitor cells are cells that differentiate into dopaminergic neuronal cells and cannot differentiate into non-dopaminergic neuronal cells. In some aspects, such determined dopamine neuronal progenitor cells are further differentiated into committed dopaminergic neuronal progenitor cells. In some aspects, PSCs are differentiated into floor plate midbrain progenitor cells, into dopaminergic neuronal cells, determined dopaminergic neuronal progenitor cells, committed dopaminergic neuronal progenitor cells, and finally, into dopaminergic neuronal cells.

The provided embodiments address problems related to the manufacture of cells that are useful for treating Parkinson's disease (PD), which is characterized by the selective degeneration of midbrain dopamine (mDA) neurons in patients' brains. Because PD symptoms are primarily due to the selective loss of DA neurons in the substantia nigra of the ventral midbrain, PD is considered suitable for cell replacement therapeutic strategies.

In some embodiments, the provided methods for differentiating PSCs into dopaminergic neuronal progenitor cells and related cell types are based on findings that initiating a culture of PSCs as non-adherent cells in the presence of SB and LDN on the day of seeding (Day 0), followed by further including SHH, PUR, and CHIR beginning on the second day of the first incubation (Day 1), to generate spheroid(s), followed by a further incubation of cells of the spheroid on a substrate-coated plate, produces differentiated cells with superior properties, and in an accelerated timeline that is superior to other methods. In particular, it was discovered that culturing PSCs in accordance with the methods described herein can accelerate the differentiation of PSCs into dopaminergic neuronal precursor cells that are suitable for therapeutic use several days faster than other methods. This is beneficial in several ways, including by reducing the amount of time and resources, including cost, needed to produce iPSC-derived dopaminergic neuronal precursor cells having the characteristics suitable for therapeutic purposes. Further aspects of the provided methods include harvesting cells at a time at which the cells are determined dopaminergic neuronal precursor cells or committed dopaminergic neuronal precursor cells that are cells that are able to differentiate into dopaminergic neurons but cannot differentiate into non-dopaminergic neurons. In some embodiments of the provided methods, such cells are cells that are differentiated in accord with the provided methods and are harvested between about Day 14 and about Day 17. This is earlier than other methods where differentiated determined dopaminergic neuronal precursor cells or committed dopaminergic progenitor cells are harvested at Day 20 or beyond, including Day 25.

In some cases, the methods described herein include culturing PSCs into spheroids in a non-adherent culture (i.e., suspension culture) for about 7 days, prior to dissociating the spheroids and continuing culture if the dissociated cells on a plate, e.g., a substrate-coated plate (i.e., as an adherent culture) until harvesting. The provided methods of differentiating cells in non-adherent cultures as described herein is associated with advantages compared to alternative methods, including those described above involving superior manufacturability, such as methods in which an entire process of differentiation is carried out by adherent culture of cells.

In some cases, the non-adherent culture of the provided methods is advantageous compared to differentiation methods that do not involve non-adherent culture of cells, because the effect of the variability of one or more substrates and/or one or more reagents on cell differentiation is reduced or eliminated during the non-adherent culture. Specifically, adherent culture may involve the coating of a plate with one or more substrates or reagents, and such coating may be uneven, thereby leading to variable provision of the one or more substrates and/or reagents to the adherent cells, particularly in methods in which the entire process of differentiation is carried out by adherent culture of cells. Such variable provision of substrates and/or reagents to adherent cells can increase variability in the harvested cells produced by the differentiation method. By contrast, substrates and/or reagents may either be unnecessary in a non-adherent culture, or are evenly dispersed throughout a non-adherent culture. In the case of the latter, the cultured cells (e.g., spheroids) are surrounded on all sides by the culture medium, such that cells are equally exposed to any substrates and/or reagents in the culture medium. Thus, in aspects of provided embodiments, cells produced by differentiation methods including non-adherent culture may exhibit reduced variability.

The non-adherent suspension culture methods described herein are also advantageous compared to methods that do not include non-adherent culture, because non-adherent culture allows for increased cell-to-cell interaction. In particular, cells in an adherent (e.g., monolayer) culture only contact other cells on their lateral surfaces. By contrast, cells in a non-adherent (e.g., suspension) culture are able to contact other cells across their entire surfaces. Such increased cell-to-cell contact in a non-adherent culture may be advantageous by more faithfully recapitulating the physiological environment. For example, the increased cell-to-cell contact allowed by the non-adherent culture methods described herein may upregulate cell-to-cell protein networks, as observed in vivo.

In some aspects, the provided non-adherent culture methods described herein provide for an ease and efficiency of culturing a greater number of cells, as compared to alternative methods, such as methods in which an entire process of differentiation is carried out by adherent culture of cells. For example, in an adherent (e.g., monolayer) culture, the number of cells cultured increases on a two-dimensional scale (i.e., the length and width of the culturing surface) with the surface area of the culturing surface. By contrast, in a non-adherent (e.g., suspension) culture, the number of cells cultured increases on a three-dimensional scale with the volume of the culturing vessel, or the volume of the culture medium contained therein. Thus, in some cases, non-adherent culture is more economical and efficient, in that fewer resources (e.g., culture vessels and reagents) are used, more cells can be generated, or both, as compared to adherent-culture. In this way, the provided methods of non-adherent culture can enable scaling in manufacturing and production processes.

In some aspects, cells produced by use of the provided non-adherent culture methods described herein also provide advantages over those produced using adherent methods and other non-adherent methods. For example, cells produced by exposing pluripotent stem cells to an inhibitor of TGF-β/activin-Nodal signaling (e.g., SB431542) and an inhibitor of bone morphogenetic protein (BMP) signaling (e.g., LDN193189) for one day (Day 0) starting when the cells are seeded, and then waiting until the second day (Day 1) to begin exposing the cells to at least one activator of Sonic Hedgehog (SHH) signaling (e.g., SHH protein and/or purmorphamine), and an inhibitor of glycogen synthase kinase 3β (GSK3β) signaling (e.g., CHIR99021) can advantageously exhibit one or more of: (i) increased expression of the dopaminergic lineage marker EN1 on or about Day 7 as compared to if the cells were exposed to each of these agents beginning on Day 0; (ii) reduced expression of the off-target non-dopaminergic lineage marker GBX2 on or about Day 7 as compared to if the cells were exposed to each of these agents beginning on Day 0; and (iii) increased expression of the dopaminergic lineage marker LMX1A on or about Day 10 as compared to if the cells were exposed to each of these agents beginning on Day 0. Accordingly, in some cases, exposing the cells to an inhibitor of TGF-β/activin-Nodal signaling (e.g., SB431542) and an inhibitor of BMP signaling (e.g., LDN193189) beginning on Day 0 when the cells are seeded, and then waiting until Day 1 to begin exposing the cells to at least one activator of SHH signaling (e.g., SHH protein and/or purmorphamine), and an inhibitor of GSK3β signaling (e.g., CHIR99021), advantageously results in increased specificity for the dopaminergic lineage as compared to if the cells were exposed to each of these agents beginning on Day 0.

In some aspects, the provided non-adherent culture methods described herein provide for advantages over adherent culture methods and other non-adherent culture methods with regards to manufacturability, including reduced cost and reduced time involved, by accelerating the differentiation timeline as compared to adherent culture methods. For instance, PSC-derived differentiated dopaminergic neurons cultured in accordance with the non-adherent culture methods described herein may exhibit a gene expression profile on, e.g., Day 16, that is comparable to the gene expression profile of, e.g., Day 20 or Day 21, of PSC-derived differentiated dopaminergic neurons cultured using an adherent culture method. This can advantageously reduce the amount of resources, including media, inhibitors, and other supplements, that are required, and can also advantageously reduce the amount of time required to produce PSC-derived differentiated dopaminergic neurons, e.g., by allowing for harvesting or collection between approximately Days 14-17, e.g., on or about Day 14, 15, 16, or 17.

Further, particular benefits are associated with methods of differentiating cells that include a non-adherent culture of only about 7 days. The non-adherent culture of about 7 days described herein produces spheroids. If non-adherent culture is allowed to proceed beyond 7 days, the increasing size of the spheroids may limit mass transport and result in reagent (e.g., morphogen) gradients across the diameter of the spheroids. Substantial reagent (e.g., morphogen) gradients across the diameter of the spheroids is undesirable, as different cells of the spheroids would be exposed to different concentration of a reagent (e.g., a morphogen), thereby leading to variable cell response and differentiation. Thus, the methods described herein including non-adherent culture of only about or up to 7 days are advantageous because variability in the concentration of reagents such as morphogen(s) to which the cells of the spheroids are exposed is minimized.

In some aspects, limiting the non-adherent culture component of the methods described herein to about 7 days also helps ensure the consistent differentiation of cultured cells. This is because long-term (e.g., greater than about 7 days) differentiation of PSCs in non-adherent (e.g., suspension) culture may allow PSCs to establish a microenvironment that allows for self-renewal in a pluripotent state. Thus, the methods described herein ensure the consistent and effective differentiation of the cultured cells by reducing or eliminating the opportunity for PSCs to persist in culture.

In some embodiments, cells produced using the methods described herein, or therapeutic compositions containing such cells, may exhibit an improved ability to engraft and/or innervate other cells compared to cells harvested at later times of the differentiation method (e.g., Day 25). In some embodiments, cells harvested between Days 14 and 17 may also exhibit improved efficacy in vivo, due to their state of differentiation and neuronal commitment. For example, cells harvested on Day 16 may demonstrate improved engraftment and/or innervation, improved efficacy, or both, as compared to cells harvested on Day 25. Accordingly, cells differentiated using the methods described herein may demonstrate improved engraftment and/or innervation, improved efficacy, or both, in addition to its improved manufacturability through reduced time and resources, including cost, involved.

In some embodiments, cells harvested by the provided differentiation method exhibit therapeutic effect(s) to treat a neurodegenerative disease. In some embodiments, the ability for differentiated cells to treat a neurodegenerative disease can be determined in an animal model of a neurodegenerative disease. In some embodiments, the neurodegenerative disease is Parkinson's disease. In some embodiments, differentiated cells harvested by provided method are screened using an animal model of Parkinson's disease. Any known and available animal model of Parkinson's disease can be used for screening. In some embodiments, the animal model is a lesion model wherein animals receive unilateral stereotaxic injection of 6-hydroxydopamine (6-OHDA) into the substantia nigra. In some embodiments, the animal model is a lesion model wherein animals receive unilateral stereotaxic injection of 6-OHDA into the medial forebrain bundle. In some embodiments, a therapeutic composition containing differentiated cells produced by the provided method, e.g., harvested cells, such as between Days 14 and 17, e.g., Day 16 cells, are implanted into the substantia nigra of the animal model. In some embodiments, a behavioral assay is performed to screen for therapeutic effects of the implantation on the animal model. In some embodiments, the behavioral assay comprises monitoring amphetamine-induced circling behavior. In some embodiments, differentiated cells exhibit a therapeutic effect to treat a neurodegenerative disease if it such cells are determined to reduce, decrease or reverse a Parkinsonian model brain lesion in this model.

Further, unlike certain previously reported methods, the differentiated cells produced by the methods described herein demonstrate physiological consistency. Importantly, this physiological consistency is maintained across cells differentiated from different subjects. This method therefore reduces variability both within and among subjects, and allows for better predictability of cell behavior in vivo. These benefits are associated with a successful therapeutic strategy, especially in the setting of autologous stem cell transplant, where cells are generated separately for each patient. Such reproducibility benefits among different subjects may also enable scaling in manufacturing and production processes.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

A. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known. Reference to "about" a value or parameter herein includes (and describes) embodiments that are directed to that value or parameter per se. For example, description referring to "about X" includes description of "X".

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker. When referring to a marker in the cell, such as a transcriptional or translational product, the term refers to the presence of detectable transcriptional or translational product, for example, wherein the product is detected at a level substantially above the level detected carrying out the same procedure with a control under otherwise identical conditions and/or at a level substantially similar to that for a cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker. When referring to a marker in the cell, such as a transcriptional or translational product, the term refers to the absence of detectable transcriptional or translational product, for example, wherein the product is not detected at a level substantially above the level detected carrying out the same procedure with a control under otherwise identical conditions, and/or at a level substantially lower than that for cell known to be positive for the marker, and/or at a level substantially similar as compared to that for a cell known to be negative for the marker.

The term "expression" or "expressed" as used herein in reference to a gene refers to the transcriptional and/or translational product of that gene. The level of expression of a DNA molecule in a cell may be determined on the basis of either the amount of corresponding mRNA that is present within the cell or the amount of protein encoded by that DNA produced by the cell RNA sequencing (RNAseq) is commonly used to determine the level of expression of a gene. See, e.g., Conesa et al. (2016) *Genome Biology* 17:13 for a review of RNAseq methods.

As used herein, the term "stem cell" refers to a cell characterized by the ability of self-renewal through mitotic cell division and the potential to differentiate into a tissue or an organ. Among mammalian stem cells, embryonic and somatic stem cells can be distinguished. Embryonic stem cells reside in the blastocyst and give rise to embryonic tissues, whereas somatic stem cells reside in adult tissues for the purpose of tissue regeneration and repair.

As used herein, the term "adult stem cell" refers to an undifferentiated cell found in an individual after embryonic development. Adult stem cells multiply by cell division to replenish dying cells and regenerate damaged tissue. An adult stem cell has the ability to divide and create another cell like itself or to create a more differentiated cell. Even though adult stem cells are associated with the expression of pluripotency markers such as Rex1, Nanog, Oct4 or Sox2, they do not have the ability of pluripotent stem cells to differentiate into the cell types of all three germ layers.

As used herein, the terms "induced pluripotent stem cell," "iPS" and "iPSC" refer to a pluripotent stem cell artificially derived (e.g., through man-made manipulation) from a non-pluripotent cell. A "non-pluripotent cell" can be a cell of lesser potency to self-renew and differentiate than a pluripotent stem cell. Cells of lesser potency can be, but are not limited to adult stem cells, tissue specific progenitor cells, primary or secondary cells.

As used herein, the term "pluripotent" or "pluripotency" refers to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism.

As used herein, the term "pluripotent stem cell characteristics" refer to characteristics of a cell that distinguish pluripotent stem cells from other cells. Expression or non-expression of certain combinations of molecular markers are examples of characteristics of pluripotent stem cells. More specifically, human pluripotent stem cells may express at least some, and optionally all, of the markers from the following non-limiting list: SSEA-3, SSEA-4, TRA-1-60, TRA-1-81, TRA-2-49/6E, ALP, Sox2, E-cadherin, UTF-1, Oct4, Lin28, Rex1, and Nanog. Cell morphologies associated with pluripotent stem cells are also pluripotent stem cell characteristics.

As used herein, the term "reprogramming" refers to the process of dedifferentiating a non-pluripotent cell into a cell exhibiting pluripotent stem cell characteristics.

The term "differentiated" or "committed" as used herein refers to a cell or cells that have acquired a cell type-specific function.

A "neuronal precursor cell" is a cell that has a tendency to differentiate into a neuronal or glial cell and does not have the pluripotent potential of a stem cell. A neuronal precursor is a cell that is committed to the neuronal or glial lineage and is characterized by expressing one or more marker genes that are specific for the neuronal or glial lineage. The terms "neural" and "neuronal" are used according to their common meaning in the art and can be used interchangeably herein throughout.

A "dopaminergic cell" or a "differentiated dopaminergic cell" as used herein refers to a cell capable of synthesizing the neurotransmitter dopamine. In some embodiments, the dopaminergic cell is an A9 dopaminergic cell. The term "A9 dopaminergic cell" refers to the most densely packed group of dopaminergic cells in the human brain, which are located in the *pars compacta* of the substantia nigra in the midbrain of healthy, adult humans.

The terms "dopaminergic neuronal progenitor cell" and "determined dopaminergic progenitor cell" as used herein refers to a cell that will differentiate into a dopaminergic neuron and cannot differentiate into a non-dopaminergic cell. A "determined dopaminergic progenitor cell" is a cell able to differentiate into a dopaminergic neuron independently of its environment. A determined dopaminergic progenitor cell may express Foxa2 or Nurrl. A determined dopaminergic progenitor cell, in some embodiments, does not express substantial levels of serotonin.

A "committed dopaminergic progenitor cell," as used herein, is a dopaminergic neuronal progenitor cell that is at a differentiation state that follows the determined dopaminergic neuronal progenitor cell stage of differentiation.

As used herein, the term "adherent culture vessel" refers to a culture vessel to which a cell may attach via extracellular matrix molecules and the like, and requires the use of an enzyme (e.g., trypsin, dispase, etc.) for detaching cells from the culture vessel. An "adherent culture vessel" is opposed to a culture vessel to which cell attachment is reduced and does not require the use of an enzyme for removing cells from the culture vessel.

As used herein, the term "non-adherent culture vessel" refers to a culture vessel to which cell attachment is reduced or limited, such as for a period of time. A non-adherent culture vessel may contain a low attachment or ultra-low attachment surface, such as may be accomplished by treating the surface with a substance to prevent cell attachment, such as a hydrogel (e.g., a neutrally charged and/or hydrophilic hydrogel) and/or a surfactant (e.g., pluronic acid). A non-adherent culture vessel may contain rounded or concave wells, and/or microwells (e.g., Aggrewells™). In some embodiments, a non-adherent culture vessel is an Aggrewell™ plate. For non-adherent culture vessels, use of an enzyme to remove cells from the culture vessel may not be required.

As used herein, the term "cell culture" may refer to an in vitro population of cells residing outside of an organism. The cell culture can be established from primary cells isolated from a cell bank or animal, or secondary cells that are derived from one of these sources and immortalized for long-term in vitro cultures.

As used herein, the terms "culture," "culturing," "grow," "growing," "maintain," "maintaining," "expand," "expanding," etc., when referring to cell culture itself or the process of culturing, can be used interchangeably to mean that a cell is maintained outside the body (e.g., ex vivo) under conditions suitable for survival. Cultured cells are allowed to survive, and culturing can result in cell growth, differentiation, or division.

As used herein, a composition refers to any mixture of two or more products, substances, or compounds, including cells. It may be a solution, a suspension, liquid, powder, a paste, aqueous, non-aqueous or any combination thereof.

The term "pharmaceutical composition" refers to a composition suitable for pharmaceutical use, such as in a mammalian subject (e.g., a human). A pharmaceutical composition typically comprises an effective amount of an active agent (e.g., cells) and a carrier, excipient, or diluent. The carrier, excipient, or diluent is typically a pharmaceutically acceptable carrier, excipient or diluent, respectively.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, a "subject" is a mammal, such as a human or other animal, and typically is human.

As used herein, "Day 0" refers to a 24-hour period in which the cells are plated/seeded at the initiation of the 24 hour period of Day 0, and "Day 1" refers to the subsequent day (also a 24 hour period) that begins 24 hours after the initiation of Day 0. Each subsequent day also refers to a 24 hour period, in succession.

B. Methods for Differentiating Cells

Provided herein are methods of differentiating stem cells, including induced pluripotent stem cells (iPSCs) and embryonic stem cells, into neural cells. In some embodiments, the methods involve performing a first incubation that includes culturing pluripotent stem cells in a non-adherent culture vessel under conditions to produce a cellular spheroid. The pluripotent stem cells are exposed to at least one inhibitor of TGF-β/activin-Nodal signaling and at least one inhibitor of bone morphogenetic protein (BMP) signaling for at least one day (Day 0) in the absence of: x) an activator of Sonic Hedgehog (SHH) signaling, and y) an inhibitor of glycogen synthase kinase 3β (GSK3β) signaling. Starting on the second day (Day 1) of the first incubation, the pluripotent stem cells are exposed to at least one activator of Sonic Hedgehog (SHH) signaling and at least one inhibitor of glycogen synthase kinase 3β (GSK3β) signaling. The spheroid cells are then subjected to a second incubation that includes culturing cells of the spheroid in a substrate-coated culture vessel under conditions to neurally differentiate the cells. In some embodiments, the first incubation involves non-adherent culturing conditions, e.g., as described in Section B.1, and, the second incubation involves adherent culture conditions, e.g., as described in Section B.4. A schematic of some embodiments of the provided methods is shown in FIG. 1.

The provided protocols involve subjecting iPSCs to cell culture methods that induce their differentiation into floor plate midbrain progenitor cells, dopaminergic neuronal progenitor cells, including determined dopaminergic neuronal progenitor cells, committed dopaminergic neuronal progenitor cells and/or, dopaminergic neuronal cells. The provided suspension culture methods of differentiating neural cells are sometimes referred to herein as "Day 1" suspension culture differentiation protocols, in reference to the first exposure of the cells to an activator of SHH and an inhibitor of glycogen synthase kinase 3β (GSK3β) signaling on Day 1 (the second day) of the protocol.

In some embodiments, iPSCs are generated from fibroblasts of human patients with Parkinson's disease. In a first incubation, the iPSCs were then differentiated to midbrain floor plate precursors and grown as spheroids in a non-adherent culture by exposure to small molecules, such as LDN, SB, PUR, SHH, CHIR, and combinations thereof, beginning on Day 0 (SB, LDN) or Day 1 (SHH/PUR, CHIR). The resulting spheroids are then transferred to an adherent culture as part of a second incubation, optionally following dissociation of the spheroid, before being exposed to additional small molecules (e.g., LDN, CHIR, BDNF, GDNF, ascorbic acid, dbcAMP, TGFβ3, DAPT, and combinations thereof) to induce further differentiation into engraftable determined dopaminergic neuronal progenitor cells, committed dopaminergic neuronal progenitor cells or dopaminergic neuronal cells.

1. Samples and Cell Preparation

In embodiments of the provided method, pluripotent stem cells are differentiated into floor plate midbrain progenitor cells, determined dopaminergic neuronal progenitor cells, committed dopaminergic neuronal progenitor cells, and/or, dopaminergic neuronal cells. Various sources of pluripotent stem cells can be used in the method, including embryonic stem (ES) cells and induced pluripotent stem cells (iPSCs).

In some aspects, pluripotency refers to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism. A standard art-accepted test, such as the ability to form a teratoma in 8-12 week old SCID mice, can be used to establish the pluripotency of a cell population. However, identification of various pluripotent stem cell characteristics can also be used to identify pluripotent cells. In some aspects, pluripotent stem cells can be distinguished from other cells by particular characteristics, including by expression or non-expression of certain combinations of molecular markers. More specifically, human pluripotent stem cells may express at least some, and optionally all, of the markers from the following non-limiting list: SSEA-3, SSEA-4, TRA-1-60, TRA-1-81, TRA-2-49/6E, ALP, Sox2, E-cadherin, UTF-1, Oct4, Lin28, Rex1, and Nanog. In some aspects, a pluripotent stem cell characteristic is a cell morphologies associated with pluripotent stem cells.

In some embodiments, pluripotent stem cells are induced pluripotent stem cells (iPSCs), artificially derived from a non-pluripotent cell. In some aspects, a non-pluripotent cell is a cell of lesser potency to self-renew and differentiate than a pluripotent stem cell. iPSCs may be generated by a process known as reprogramming, wherein non-pluripotent cells are effectively "dedifferentiated" to an embryonic stem cell-like state by engineering them to express genes such as OCT4, SOX2, and KLF4. Takahashi and Yamanaka (2006) *Cell* 126: 663-76.

Methods for generating iPSCs are known. For example, mouse iPSCs were reported in 2006 (Takahashi and Yamanaka), and human iPSCs were reported in late 2007 (Takahashi et al. (2007) *Cell* 131: 861-872 and Yu et al. (2007) Science 318: 1917-1920). Mouse iPSCs demonstrate important characteristics of pluripotent stem cells, including the expression of stem cell markers, the formation of tumors containing cells from all three germ layers, and the ability to contribute to many different tissues when injected into mouse embryos at a very early stage in development. Human iPSCs also express stem cell markers and are capable of generating cells characteristic of all three germ layers.

In some embodiments, the PSCs (e.g., iPSCs) are autologous to the subject to be treated, i.e., the PSCs are derived from the same subject to whom the differentiated cells are administered. In some embodiments, non-pluripotent cells (e.g., fibroblasts) derived from patients having Parkinson's disease (PD) are reprogrammed to become iPSCs before differentiation into neural and/or neuronal cells. In some embodiments, fibroblasts may be reprogrammed to iPSCs by transforming fibroblasts with genes (OCT4, SOX2, NANOG, LIN28, and KLF4) cloned into a plasmid (for example, see, Yu, et al., Science DOI: 10.1126/science.1172482). In some embodiments, non-pluripotent fibroblasts derived from patients having PD are reprogrammed to become iPSCs before differentiation into determined dopaminergic neuronal progenitor cells, committed dopaminergic neuronal progenitor cells and/or dopaminergic neuronal cells, such as by use of the non-integrating Sendai virus to reprogram the cells (e.g., use of CTS™ CytoTune™-iPS 2.1 Sendai Reprogramming Kit). In some embodiments, the resulting differentiated cells are then administered to the patient from whom they are derived in an autologous stem cell transplant. In some embodiments, the PSCs (e.g., iPSCs) are allogeneic to the subject to be treated, i.e., the PSCs are derived from a different individual than the subject to whom the differentiated cells will be administered. In some embodiments, non-pluripotent cells (e.g., fibroblasts) derived from another individual (e.g., an individual not having a neurodegenerative disorder, such as Parkinson's disease) are reprogrammed to become iPSCs before differentiation into determined dopaminergic neuronal progenitor cells, committed dopaminergic neuronal progenitor cells and/or dopaminergic neuronal cells. In some embodiments, reprogramming is accomplished, at least in part, by use of the non-integrating Sendai virus to reprogram the cells (e.g., use of CTS™ CytoTune™-iPS 2.1 Sendai Reprogramming Kit). In some embodiments, the resulting differentiated cells are then administered to an individual who is not the same individual from whom the differentiated cells are derived (e.g., allogeneic cell therapy or allogeneic cell transplantation).

In any of the provided embodiments, the PSCs described herein (e.g., allogeneic cells) may be genetically engineered to be hypoimmunogenic. Methods for reducing the immunogenicity are known, and include ablating polymorphic HLA-A/-B/-C and HLA class II molecule expression and introducing the immunomodulatory factors PD-L1, HLA-G, and CD47 into the AAVS1 safe harbor locus in differentiated cells. Han et al., PNAS (2019) 116(21):10441-46. Thus, in some embodiments, the PSCs described herein are engineered to delete highly polymorphic HLA-A/-B/-C genes and to introduce immunomodulatory factors, such as PD-L1, HLA-G, and/or CD47, into the AAVS1 safe harbor locus.

In some embodiments, PSC (e.g., iPSCs) are cultured in the absence of feeder cells, until they reach 75-90% confluency, at which point they are harvested and further cultured for differentiation (Day 0). In one aspect of the method described herein, once iPSCs reach 75-90% confluence, they are washed in phosphate buffered saline (PBS) and subjected to enzymatic dissociation, such as with Accutase™, until the cells are easily dislodged from the surface of a culture vessel. The dissociated iPSCs are then re-suspended in media for downstream differentiation into determined dopaminergic neuronal progenitor cells, committed dopaminergic neuronal progenitor cells, and/or dopaminergic neuronal cells.

In some embodiments, the PSCs are resuspended in a basal induction media. In some embodiments, the basal induction media is formulated to contain Neurobasal™ media and DMEM/F12 media at a 1:1 ratio, supplemented with N-2 and B27 supplements, non-essential amino acids (NEAA), GlutaMAX™, L-glutamine, β-mercaptoethanol, and insulin. In some embodiments, at the time of seeding (Day 0), the basal induction media is further supplemented with serum replacement, a Rho-associated protein kinase (ROCK) inhibitor, and certain small molecules, e.g., an inhibitor of TGF-β/activin-Nodal signaling, and an inhibitor of BMP signaling, for differentiation. In some embodiments, the PSCs are resuspended in the same media they will be cultured in for at least a portion of the first incubation.

2. Non-Adherent Culture

The provided methods include culturing PSCs (e.g., iPSCs) by incubation with certain molecules (e.g., small molecules) to induce their differentiation into floor plate midbrain progenitor cells, dopaminergic neuronal progenitor cells, including determined dopaminergic neuronal progenitor cells, committed dopaminergic neuronal progenitor cells and/or, dopaminergic neuronal cells. In particular, the provided embodiments include a first incubation of PSCs under non-adherent conditions to produce spheroids, in the presence of certain molecules (e.g., small molecules), at certain timing, which can, in some aspects, improve the consistency of producing physiologically relevant cells for implantation, and also improve manufacturing by accelerating the timeline for differentiating the iPSCs into, e.g., determined dopaminergic neuronal progenitor cells, committed dopaminergic neuronal progenitor cells, and/or dopaminergic neuronal cells, thereby advantageously reducing the amount of time and resources needed for the differentiation process. In some embodiments, the methods include performing a first incubation involving culturing pluripotent stem cells in a non-adherent culture vessel under conditions to produce a cell spheroid. The first incubation includes (i) exposing the pluripotent stem cells are exposed to at least one inhibitor of TGF-β/activin-Nodal signaling and at least one inhibitor of bone morphogenetic protein (BMP) signaling for at least one day (Day 0); and (ii) starting on the second day (Day 1) of the first incubation, exposing the pluripotent stem cells to at least one activator of Sonic Hedgehog (SHH) signaling and at least one inhibitor of glycogen synthase kinase 3β (GSK3β) signaling. In some embodiments, the Day 0 incubation is done in the absence of x) an activator of Sonic Hedgehog (SHH) signaling, and y) an inhibitor of glycogen synthase kinase 3β (GSK3β) signaling.

In some embodiments, a non-adherent culture vessel is a culture vessel with a low or ultra-low attachment surface, such as to inhibit or reduce cell attachment. In some embodiments, culturing cells in a non-adherent culture vessel does not prevent all cells of the culture from attaching the surface of the culture vessel.

In some embodiments, a non-adherent culture vessel is a culture vessel with an ultra-low attachment surface. In some aspects, an ultra-low attachment surface may inhibit cell attachment for a period of time. In some embodiments, an ultra-low attachment surface may inhibit cell attachment for the period of time necessary to obtain confluent growth of the same cell type on an adherent surface. In some embodiments, the ultra-low attachment surface is coated or treated with a substance to prevent cell attachment, such as a hydrogel layer (e.g., a neutrally charged and/or hydrophilic hydrogel layer). In some embodiments, a non-adherent culture vessel is coated or treated with a surfactant prior to the first incubation. In some embodiments, the surfactant is pluronic acid.

In some embodiments, a non-adherent culture vessel allows for three-dimensional formation of cell aggregates. In some embodiments, iPSCs are cultured in a non-adherent culture vessel, such as a multi-well plate, to produce cell aggregates (e.g., spheroids). In some embodiments, iPSCs are cultured in a non-adherent culture vessel, such as a multi-well plate, to produce cell aggregates (e.g., spheroids) on about Day 7 of the method. In some embodiments, the cell aggregate (e.g., spheroid) expresses at least one of PAX6 and OTX2 on or by about Day 7 of the method.

In some embodiments, the first incubation includes culturing pluripotent stem cells in a non-adherent culture vessel under conditions to produce a cellular spheroid.

In some embodiments, the non-adherent culture vessel is a plate, a dish, a flask, or a bioreactor. In some embodiments, the non-adherent culture vessel is a plate, such as a multi-well plate. In some embodiments, the non-adherent culture vessel is a 6-well or 24-well plate. In some embodiments, the wells of the multi-well plate further include micro-wells. In some of the provided embodiments, a non-adherent culture vessel, such as a multi-well plate, has round or concave wells and/or microwells. In some of the provided embodiments, a non-adherent culture vessel, such as a multi-well plate, does not have corners or seams.

In some embodiments, the non-adherent culture vessel is a multiwell plate in which each well contains microwells, and the number of PSCs plated on Day 0 of the method is approximately 3,000 cells per microwell. For example, in an AggreWell 400 24 well plate, each well contains about 1200 microwells that each have a 400 μM diameter, and approximately $3.6\times10^6$ cells are plated per well, thereby averaging approximately 3,000 cells per microwell. An AggreWell 400 6 well plate has about 5900 microwells per well that have a 400 μM diameter, so in some embodiments, when such a 6-well plate is used, approximately $17.7\times10^6$ cells are plated per well, thereby averaging approximately 3,000 cells per microwell.

In some embodiments, the number of PSCs plated on Day 0 of the method is between about between about $0.1\times10^6$ cells/cm$^2$ and about $2\times10^6$ cells/cm$^2$, between about $0.1\times10^6$ cells/cm$^2$ and about $1\times10^6$ cells/cm$^2$, between about $0.1\times10^6$ cells/cm$^2$ and about $0.8\times10^6$ cells/cm$^2$, between about $0.1\times10^6$ cells/cm$^2$ and about $0.6\times10^6$ cells/cm$^2$, between about $0.1\times10^6$ cells/cm$^2$ and about $0.4\times10^6$ cells/cm$^2$, between about $0.1\times10^6$ cells/cm$^2$ and about $0.2\times10^6$ cells/cm$^2$, between about $0.2\times10^6$ cells/cm$^2$ and about $2\times10^6$ cells/cm$^2$, between about $0.2\times10^6$ cells/cm$^2$ and about $1\times10^6$ cells/cm$^2$, between about $0.2\times10^6$ cells/cm$^2$ and about $0.8\times10^6$ cells/cm$^2$, between about $0.2\times10^6$ cells/cm$^2$ and about $0.6\times10^6$ cells/cm$^2$, between about $0.2\times10^6$ cells/cm$^2$ and about $0.4\times10^6$ cells/cm$^2$, between about $0.4\times10^6$ cells/cm$^2$ and about $2\times10^6$ cells/cm$^2$, between about $0.4\times10^6$ cells/cm$^2$ and about $1\times10^6$ cells/cm$^2$, between about $0.4\times10^6$ cells/cm$^2$ and about $0.8\times10^6$ cells/cm$^2$, between about $0.4\times10^6$ cells/cm$^2$ and about $0.6\times10^6$ cells/cm$^2$, between about $0.6\times10^6$ cells/cm$^2$ and about $2\times10^6$ cells/cm$^2$, between about $0.6\times10^6$ cells/cm$^2$ and about $1\times10^6$ cells/cm$^2$, between about $0.6\times10^6$ cells/cm$^2$ and about $0.8\times10^6$ cells/cm$^2$, between about $0.8\times10^6$ cells/cm$^2$ and about $2\times10^6$ cells/cm$^2$, between about $0.8\times10^6$ cells/cm$^2$ and about $1\times10^6$ cells/cm$^2$, or between about $1.0\times10^6$ cells/cm$^2$ and about $2\times10^6$ cells/cm$^2$. In some embodiments, the number of cells plated on the substrate-coated culture vessel is between about $0.4\times10^6$ cells/cm$^2$ and about $0.8\times10^6$ cells/cm$^2$.

In some embodiments, the number of PSCs plated on Day 0 of the method is between about $1\times10^5$ pluripotent stem cells per well and about $20\times10^6$ pluripotent stem cells per well, between about $1\times10^5$ pluripotent stem cells per well and about $15\times10^6$ pluripotent stem cells per well, between about 1×10 pluripotent stem cells per well and about $10\times10^6$ pluripotent stem cells per well, between about 1×10 pluripotent stem cells per well and about $5\times10^6$ pluripotent stem cells per well, between about 1×10 pluripotent stem cells per well and about $1\times10^6$ pluripotent stem cells per well, between about $1\times10^1$ pluripotent stem cells per well and about $5\times10$ pluripotent stem cells per well, between about $5\times10$ pluripotent stem cells per well and about $20\times10^6$ pluripotent stem cells per well, between about $5\times10^5$ pluripotent stem cells per well and about $15\times10^6$ pluripotent stem cells per well, between about $5\times10^5$ pluripotent stem cells per well and about $10\times10^6$ pluripotent stem cells per well, between about $5\times10^5$ pluripotent stem cells per well and about $5\times10^6$ pluripotent stem cells per well, between about $5\times10^5$ pluripotent stem cells per well and about $1\times10^6$ pluripotent stem cells per well, between about $1\times10^6$ pluripotent stem cells per well and about $20\times10^6$ pluripotent stem cells per well, between about $1\times10^6$ pluripotent stem cells per well and about $15\times10^6$ pluripotent stem cells per well, between about $1\times10^6$ pluripotent stem cells per well and about $10\times10^6$ pluripotent stem cells per well, between about $1\times10^6$ pluripotent stem cells per well and about $5\times10^6$ pluripotent stem cells per well, between about $5\times10^6$ pluripotent stem cells per well and about $20\times10^6$ pluripotent stem cells per well, between about $5\times10^6$ pluripotent stem cells per well and about $15\times10^6$ pluripotent stem cells per well, between about $5\times10^6$ pluripotent stem cells per well and about $10\times10^6$ pluripotent stem cells per well, between about $10\times10^6$ pluripotent stem cells per well and about $20\times10^6$ pluripotent stem cells per well, between about $10\times10^6$ pluripotent stem cells per well and about $15\times10^6$ pluripotent stem cells per well, or between about $15\times10^6$ pluripotent stem cells per well and about $20\times10^6$ pluripotent stem cells per well.

In some embodiments, the number of PSCs plated on Day 0 of the method is between about $1\times10^6$ pluripotent stem cells per well and about $10\times10^6$ pluripotent stem cells per well, between about $2\times10^6$ pluripotent stem cells per well and about $8\times10^6$ pluripotent stem cells per well, between about $2.5\times10^6$ pluripotent stem cells per well and about $5\times10^6$ pluripotent stem cells per well, or between about $3\times10^6$ pluripotent stem cells per well and about $4\times10^6$ pluripotent stem cells per well. In some embodiments, the number of PSCs plated on Day 0 of the method is at or about $3.6\times10^6$ pluripotent stem cells per well.

In some days, the number of PSCs plated on Day 0 of the method is a number of cells sufficient to produce a cellular spheroid containing between about 1,000 cells and about 5,000 cells, or between about 2,000 cells and about 3,000 cells. In some days, the number of PSCs plated on Day 0 of the method is a number of cells sufficient to produce a cellular spheroid containing between about 1,000 cells and about 5,000 cells. In some days, the number of PSCs plated on Day 0 of the method is a number of cells sufficient to produce a cellular spheroid containing between about 2,000 cells and about 3,000 cells. In some days, the number of PSCs plated on Day 0 of the method is a number of cells sufficient to produce a cellular spheroid containing about 2,000 cells. In some days, the number of PSCs plated on Day 0 of the method is a number of cells sufficient to produce a cellular spheroid containing about 3,000 cells. In some embodiments, the spheroids containing the desired number is produced by the method on or by about Day 7.

In some embodiments of the method provided herein, the first incubation includes culturing pluripotent stem cells in a non-adherent culture vessel under conditions to produce a cellular spheroid. In some embodiments, the first incubation is from about Day 0 through about Day 6. In some embodiments, the first incubation comprises culturing pluripotent stem cells in a culture media ("media"). In some embodiments, the media of the first incubation is a basal induction media for inducing differentiation of the PSCs into floor plate midbrain progenitor cells. In some embodiments, the first incubation comprises culturing pluripotent stem cells in the media from about Day 0 through about Day 6. In some embodiments, the first incubation comprises culturing pluripotent stem cells in the media to induce differentiation of the PSCs into floor plate midbrain progenitor cells.

In some embodiments, the media is also supplemented with a serum replacement containing minimal non-human-derived components (e.g., KnockOut™ serum replacement). In some embodiments, the serum replacement is provided in the media at 5% (v/v) for at least a portion of the first incubation. In some embodiments, the serum replacement is provided in the media at 5% (v/v) on Day 0 and Day 1. In some embodiments, the serum replacement is provided in the media at 2% (v/v) for at least a portion of the first incubation. In some embodiments, the serum replacement is provided in the media at 2% (v/v) from Day 2 through Day 6. In some embodiments, the serum replacement is provided in the media at 5% (v/v) on Day 0 and Day 1, and at 2% (v/v) from Day 2 through Day 6.

In some embodiments, the media is further supplemented with small molecules, such as any described above. In some embodiments, the small molecules are selected from among the group consisting of: a Rho-associated protein kinase (ROCK) inhibitor, an inhibitor of TGF-β/activin-Nodal signaling, at least one activator of Sonic Hedgehog (SHH) signaling, an inhibitor of bone morphogenetic protein (BMP) signaling, an inhibitor of glycogen synthase kinase 3β (GSK3β) signaling, and combinations thereof.

In some embodiments the media is supplemented with a Rho-associated protein kinase (ROCK) inhibitor on one or more days when cells are passaged. In some embodiments, the media is supplemented with a ROCK inhibitor each day that cells are passaged. In some embodiments the media is supplemented with a ROCK inhibitor on Day 0. In some embodiments, the pluripotent stem cells are not exposed to a ROCKi prior to exposing the pluripotent stem cells to the inhibitor of TGF-β/activin-Nodal signaling and the inhibitor of bone morphogenetic protein (BMP) signaling in the first incubation.

In some embodiments, cells are exposed to the ROCK inhibitor at a concentration of between about 1 μM and about 20 μM, between about 5 μM and about 15 μM, or between about 8 μM and about 12 μM. In some embodiments, cells are exposed to the ROCK inhibitor at a concentration of between about 1 μM and about 20 μM. In some embodiments, cells are exposed to the ROCK inhibitor at a concentration of between about 5 μM and about 15 μM. In some embodiments, cells are exposed to the ROCK inhibitor at a concentration of between about 8 μM and about 12 μM. In some embodiments, cells are exposed to the ROCK inhibitor at a concentration of at or about 10 μM.

In some embodiments, the ROCK inhibitor is selected from among the group consisting of: Fasudil, Ripasudil, Netarsudil, RKI-1447, Y-27632, GSK429286A, Y-30141, and combinations thereof. In some embodiments, the ROCK inhibitor is a small molecule. In some embodiments, the ROCK inhibitor selectively inhibits p160ROCK. In some embodiments, the ROCK inhibitor is Y-27632, having the formula:

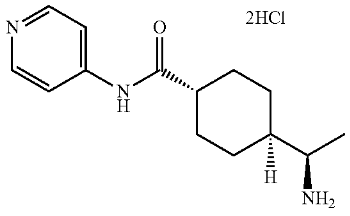 [SMILES: C[C@@H](N)[C@H]1CC[C@H](C(=O)Nc2ccncc2)CC1]

In some embodiments, cells are exposed to Y-27632 at a concentration of at or about 10 μM. In some embodiments, cells are exposed to Y-27632 at a concentration of at or about 10 μM on Day 0.

In some embodiments the media is supplemented with an inhibitor of TGF-β/activin-Nodal signaling. In some embodiments the media is supplemented with an inhibitor of TGF-β/activin-Nodal signaling up to about Day 5 (e.g., Day 4 or Day 5). In some embodiments the media is supplemented with an inhibitor of TGF-β/activin-Nodal signaling from about Day 0 through Day 4, each day inclusive.

In some embodiments, cells are exposed to the inhibitor of TGF-β/activin-Nodal signaling at a concentration of between about 1 μM and about 20 μM, between about 5 μM and about 15 μM, or between about 8 μM and about 12 μM. In some embodiments, cells are exposed to the inhibitor of TGF-β/activin-Nodal signaling at a concentration of between about 1 μM and about 20 μM. In some embodiments, cells are exposed to the inhibitor of TGF-β/activin-Nodal signaling at a concentration of between about 5 μM and about 15 μM. In some embodiments, cells are exposed to the inhibitor of TGF-β/activin-Nodal signaling at a concentration of between about 8 μM and about 12 μM. In some embodiments, cells are exposed to the inhibitor of TGF-β/activin-Nodal signaling at a concentration of at or about 10 μM.

In some embodiments, the media is partially or completely exchanged on one or more days of the first incubation, e.g., on each of Days 1 through 6. In some embodiments, the media exchange comprises replacing at or about 50% of the media with fresh media, which can be the same as or different than the previous media. In some embodiments, the media exchange comprises replacing between about 25% and about 75% of the media. In some embodiments, the media on one or more days of the first incubation, e.g., each of Days 1 through 6, is added by a 50% media exchange. For instance, the media on one or more of Days 1 through 6 is added by removing about 50% of the previous media and replacing it with an equal volume of the new media prepared for that day. Accordingly, the concentration of certain small molecules included in the media to be added through a 50% media exchange is included in the new media at a double (2×) concentration of what the cells are intended to be exposed to on that day. In some embodiments, the media added on each of Days 1 through 4 includes a concentration of the inhibitor of TGF-β/activin-Nodal signaling that is double the concentration of the inhibitor of TGF-β/activin-Nodal signaling that was included in the Day 0 media.

In some embodiments, the media added by the media exchange, e.g., a 50% media exchange, on each of Days 1 through 4 comprises an inhibitor of TGF-β/activin-Nodal signaling at a concentration of between about 2 μM and about 40 μM, between about 10 μM and about 30 μM, or between about 16 μM and about 24 μM. In some embodiments, the media added by the media exchange, e.g., a 50% media exchange, on each of Days 1 through 4 comprises the inhibitor of TGF-β/activin-Nodal signaling at a concentration of between about 2 μM and about 40 μM. In some embodiments, the media added by the media exchange, e.g., a 50% media exchange, on each of Days 1 through 4 comprises the inhibitor of TGF-β/activin-Nodal signaling at a concentration of between about 10 μM and about 30 μM. In some embodiments, the media added by the media exchange, e.g., a 50% media exchange, on each of Days 1 through 4 comprises the inhibitor of TGF-β/activin-Nodal signaling at a concentration of between about 16 μM and about 24 μM. In some embodiments, the media added by the media exchange, e.g., a 50% media exchange, on each of Days 1 through 4 comprises the inhibitor of TGF-β/activin-Nodal signaling at a concentration of at or about 20 μM.

In some embodiments, the inhibitor of TGF-β/activin-Nodal signaling is a small molecule. In some embodiments, the inhibitor of TGF-β/activin-Nodal signaling is capable of lowering or blocking transforming growth factor beta (TGFβ)/Activin-Nodal signaling. In some embodiments, the inhibitor of TGF-β/activin-Nodal signaling inhibits ALK4, ALK5, ALK7, or combinations thereof. In some embodiments, the inhibitor of TGF-β/activin-Nodal signaling inhibits ALK4, ALK5, and ALK7. In some embodiments, the inhibitor of TGF-β/activin-Nodal signaling does not inhibit ALK2, ALK3, ALK6, or combinations thereof. In some embodiments, the inhibitor does not inhibit ALK2, ALK3, or ALK6. In some embodiments, the inhibitor of TGF-β/activin-Nodal signaling is SB431542 (e.g., CAS 301836-41-9, molecular formula of C22H18N4$O_3$, and name of 4-[4-(1,3-benzodioxol-5-yl)-5-(2-pyridinyl)-1H-imidazol-2-yl]-benzamide), having the formula:

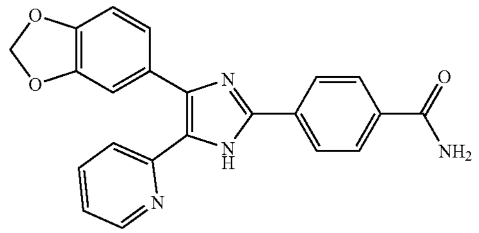 [SMILES: NC(=O)c1ccc(-c2nc(-c3ccc4c(c3)OCO4)c(-c3ccccn3)[nH]2)cc1]

In some embodiments, cells are exposed to SB431542 at a concentration of about 10 μM. In some embodiments, cells are exposed to SB431542 at a concentration of about 10 μM until about Day 5. In some embodiments, cells are exposed to SB431542 at a concentration between about 8 μM and about 15 μM from about Day 0 through about Day 4, inclusive of each day. In some embodiments, cells are exposed to SB431542 at a concentration of at or about 10 μM from about Day 0 through about Day 4, inclusive of each day.

In some embodiments the media is supplemented with an inhibitor of BMP signaling. In some embodiments the media is supplemented with an inhibitor of BMP signaling up to about Day 7 (e.g., Day 6 or Day 7). In some embodiments the media is supplemented with an inhibitor of BMP signaling from about Day 0 through Day 6, each day inclusive.

In some embodiments, cells are exposed to the inhibitor of BMP signaling at a concentration of between about 0.01 μM and about 5 μM, between about 0.05 μM and about 1 μM, between about 0.05 μM and about 0.2 μM, or between about 0.1 μM and about 0.5 μM, each inclusive. In some embodiments, cells are exposed to the inhibitor of BMP signaling at a concentration of between about 0.01 μM and about 5 μM. In some embodiments, cells are exposed to the inhibitor of BMP signaling at a concentration of between about 0.05 μM and about 1 μM. In some embodiments, cells are exposed to the inhibitor of BMP signaling at a concentration of between about 0.1 μM and about 0.5 μM. In some embodiments, cells are exposed to the inhibitor of BMP signaling at a concentration of between about 0.05 μM and about 0.2 μM. In some embodiments, cells are exposed to the inhibitor of BMP signaling at a concentration of between about 0.08 μM and about 0.15 μM. In some embodiments, cells are exposed to the inhibitor of BMP signaling at a concentration of at or about 0.1 μM.

In some embodiments, the media is at least partially exchanged with fresh media, and the media added on each of Days 1 through 6 during the media exchange includes a concentration of the inhibitor of BMP signaling that is double the concentration of the inhibitor of the inhibitor of BMP signaling that was included in the Day 0 media, e.g., due to the media being added by a 50% media exchange. In some embodiments, the media added by the media exchange, e.g., a 50% media exchange, on each of Days 1 through 6 comprises an inhibitor of BMP signaling at a concentration of between about 0.02 μM and about 10 μM, between about 0.1 μM and about 2 μM, between about 0.1 μM and about 0.4 μM, or between about 0.2 μM and about 1 μM, each inclusive. In some embodiments, the media added by the media exchange, e.g., a 50% media exchange, on each of Days 1 through 6 comprises an inhibitor of BMP signaling at a concentration of between about 0.02 μM and about 10 μM. In some embodiments, the media added by the media exchange, e.g., a 50% media exchange, on each of Days 1 through 6 comprises an inhibitor of BMP signaling at a concentration of between about 0.1 μM and about 2 μM. In some embodiments, the media added by the media exchange, e.g., a 50% media exchange, on each of Days 1 through 6 comprises an inhibitor of BMP signaling at a concentration of between about 0.2 μM and about 1 μM. In some embodiments, the media added by the media exchange, e.g., a 50% media exchange, on each of Days 1 through 6 comprises an inhibitor of BMP signaling at a concentration of between about 0.1 μM and about 0.4 μM. In some embodiments, the media added by the media exchange, e.g., a 50% media exchange, on each of Days 1 through 6 comprises an inhibitor of BMP signaling at a concentration of between about 0.16 μM and about 0.3 μM. In some embodiments, the media added by a 50% media exchange on each of Days 1 through 6 comprises an inhibitor of BMP signaling at a concentration of at or about 0.2 μM.

In some embodiments, the inhibitor of BMP signaling is a small molecule. In some embodiments, the inhibitor of BMP signaling is selected from LDN193189 or K02288. In some embodiments, the inhibitor of BMP signaling is capable of inhibiting "Small Mothers Against Decapentaplegic" SMAD signaling. In some embodiments, the inhibitor of BMP signaling inhibits ALK1, ALK2, ALK3, ALK6, or combinations thereof. In some embodiments, the inhibitor of BMP signaling inhibits ALK1, ALK2, ALK3, and ALK6. In some embodiments, the inhibitor of BMP signaling inhibits BMP2, BMP4, BMP6, BMP7, and Activin cytokine signals and subsequently SMAD phosphorylation of Smad1, Smad5, and Smad8. In some embodiments, the inhibitor of BMP signaling is LDN193189. In some embodiments, the inhibitor of BMP signaling is LDN193189 (e.g., IUPAC name 4-(6-(4-(piperazin-1-yl)phenyl)pyrazolo[1,5-a]pyrimidin-3-yl)quinoline, with a chemical formula of C25H22N6), having the formula:

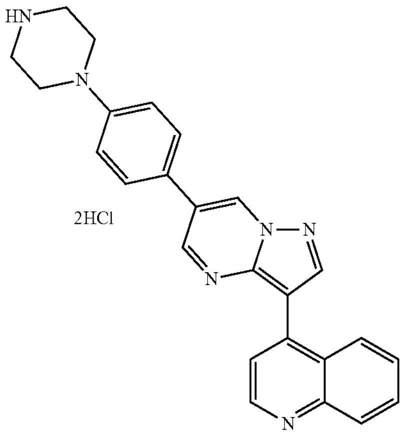 [SMILES: c1ccc2c(-c3cnn4cc(-c5ccc(N6CCNCC6)cc5)cnc34)ccnc2c1]

In some embodiments, cells are exposed to LDN193189 at a concentration of about 0.1 μM. In some embodiments, cells are exposed to LDN193189 at a concentration of about 0.1 μM up to about Day 7 (e.g., Day 6 or Day 7). In some embodiments, cells are exposed to LDN193189 at a concentration of about 0.1 μM on Day 0 and are exposed to LDN193189 at a concentration of from about 0.08 μM to about 0.15 μM from about Day 0 through about Day 6, inclusive of each day. In some embodiments, cells are exposed to LDN193189 at a concentration of about 0.1 μM from about Day 0 through about Day 6, inclusive of each day.

In some embodiments the media is supplemented with an inhibitor of GSK3β signaling. In some embodiments the media is supplemented with an inhibitor of GSK3β signaling beginning on Day 1 and up to about Day 7 (e.g., Day 6 or Day 7). In some embodiments the media is supplemented with an inhibitor of GSK3β signaling from about Day 1 through Day 6, each day inclusive. In some embodiments, the cells are not exposed to an inhibitor of GSK3β signaling prior to Day 1 of the incubation process.

In some embodiments, cells are exposed to the inhibitor of GSK3β signaling at a concentration of between about 0.1 μM and about 10 μM, between about 0.5 μM and about 8 μM, between about 0.5 μM and about 2 μM, between about 1 μM and about 4 μM, or between about 2 μM and about 3 μM, each inclusive. In some embodiments, cells are exposed to the inhibitor of GSK3β signaling at a concentration of between about 0.1 μM and about 10 μM. In some embodiments, cells are exposed to the inhibitor of GSK3β signaling at a concentration of between about 0.5 μM and about 8 μM. In some embodiments, cells are exposed to the inhibitor of GSK3β signaling at a concentration of between about 0.5 μM and about 2 μM. In some embodiments, cells are exposed to the inhibitor of GSK3β signaling at a concentration of between about 1 μM and about 4 μM. In some embodiments, cells are exposed to the inhibitor of GSK3β signaling at a concentration of between about 2 μM and about 3 μM. In some embodiments, cells are exposed to the inhibitor of GSK3β signaling at a concentration of about 1 μM on Day 1, and about 2 μM on each of Days 2 through 6. In some embodiments, cells are exposed to the inhibitor of GSK3β signaling on Day 1 at a concentration that is 50% of the concentration of the inhibitor of GSK3β signaling that the cells are exposed to on each of Days 2 through 6.

In some embodiments, the media is at least partially exchanged with fresh media, and the media added on each of Days 1 through 6 includes a concentration of the inhibitor of GSK3β signaling that is double the concentration of the inhibitor of GSK3β signaling that is intended to contact the cells, e.g., due to the media being added by a 50% media exchange. In some embodiments, the media added by a 50% media exchange on Day 1 comprises an inhibitor of GSK3β signaling at a concentration that is 50% of the concentration of the inhibitor of GSK3β signaling in the media added by a 50% media exchange on each of Days 2 through 6.

In some embodiments, the media added by the media exchange, e.g., a 50% media exchange, on each of Days 1 through 6 independently comprises an inhibitor of GSK3β signaling at a concentration of between about 0.2 μM and about 20 μM, between about 1 μM and about 16 μM, or between about 2 μM and about 8 μM, or between about 4 μM and about 6 μM, each inclusive. In some embodiments, the media added by the media exchange, e.g., a 50% media exchange, on Day 1 comprises an inhibitor of GSK3β signaling at a concentration of between about 0.1 μM and about 10 μM. In some embodiments, the media added by the media exchange, e.g., a 50% media exchange, on Day 1 comprises an inhibitor of GSK3β signaling at a concentration of between about 0.5 μM and about 8 μM. In some embodiments, the media added by the media exchange, e.g., a 50% media exchange, on Day 1 comprises an inhibitor of GSK3β signaling at a concentration of between about 1 μM and about 4 μM. In some embodiments, the media added by the media exchange, e.g., a 50% media exchange, on Day 1 comprises an inhibitor of GSK3β signaling at a concentration of between about 1 μM and about 3 μM. In some embodiments, the media added by the media exchange, e.g., a 50% media exchange, on Day 1 comprises an inhibitor of GSK3β signaling at a concentration of between about 1.5 μM and about 2.5 μM. In some embodiments, the media added by a 50% media exchange on Day 1 comprises an inhibitor of GSK3β signaling at a concentration of about 2 μM.

In some embodiments, the media added by the media exchange, e.g., a 50% media exchange, on each of Days 2 through 6 comprises an inhibitor of GSK3β signaling at a concentration of between about 0.2 μM and about 20 μM. In some embodiments, the media added by the media exchange, e.g., a 50% media exchange, on each of Days 2 through 6 comprises an inhibitor of GSK3β signaling at a concentration of between about 1 μM and about 16 μM. In some embodiments, the media added by the media exchange, e.g., a 50% media exchange, on each of Days 2 through 6 comprises an inhibitor of GSK3β signaling at a concentration of between about 2 μM and about 8 μM. In some embodiments, the media added by the media exchange, e.g., a 50% media exchange, on each of Days 2 through 6 comprises an inhibitor of GSK3β signaling at a concentration of between about 4 μM and about 6 μM. In some embodiments, the media added by the media exchange, e.g., a 50% media exchange, on each of Days 2 through 6 comprises an inhibitor of GSK3β signaling at a concentration of between about 3 μM and about 5 μM. In some embodiments, the media added by a 50% media exchange on each of Days 2 through 6 comprises an inhibitor of GSK3β signaling at a concentration of about 4 μM.

In some embodiments, the inhibitor of GSK3β signaling is selected from among the group consisting of: lithium ion, valproic acid, iodotubercidin, naproxen, famotidine, curcumin, olanzapine, CHIR99012, and combinations thereof. In some embodiments, the inhibitor of GSK3β signaling is a small molecule. In some embodiments, the inhibitor of GSK3β signaling inhibits a glycogen synthase kinase 3β enzyme. In some embodiments, the inhibitor of GSK3β signaling inhibits GSK3α. In some embodiments, the inhibitor of GSK3β signaling modulates TGF-β and MAPK signaling. In some embodiments, the inhibitor of GSK3β signaling is an agonist of wingless/integrated (Wnt) signaling. In some embodiments, the inhibitor of GSK3β signaling has an IC50=6.7 nM against human GSK3p. In some embodiments, the inhibitor of GSK3β signaling is CHIR99021 (e.g., "3-[3-(2-Carboxyethyl)-4-methylpyrrol-2-methylidenyl]-2-indolinone" or IUPAC name 6-(2-(4-(2,4-dichlorophenyl)-5-(4-methyl-1H-imidazol-2-yl)pyrimidin-2-ylamino)ethylamino)nicotinonitrile), having the formula:

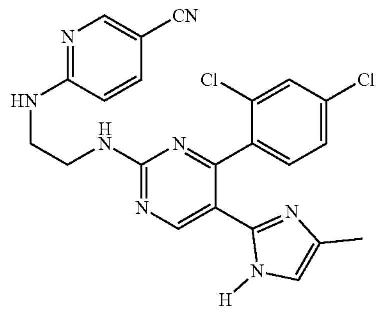 [SMILES: Cc1c[nH]c(-c2cnc(NCCNc3ccc(C#N)cn3)nc2-c2ccc(Cl)cc2Cl)n1]

In some embodiments the media is supplemented with at least one activator of sonic hedgehog (SHH) signaling. SHH refers to a protein that is one of at least three proteins in the mammalian signaling pathway family called hedgehog, another is desert hedgehog (DHH) while a third is Indian hedgehog (IHH). Shh interacts with at least two transmembrane proteins by interacting with transmembrane molecules Patched (PTC) and Smoothened (SMO). In some embodiments the media is supplemented with the at least one activator of SHH signaling beginning on Day 1 and up to about Day 7 (e.g., Day 6 or Day 7). In some embodiments the media is supplemented with the at least one activator of SHH signaling from about Day 1 through Day 6, each day inclusive. In some embodiments, the cells are not exposed to an activator of sonic hedgehog (SHH) signaling prior to Day 1 of the differentiation protocol.

In some embodiments, the at least one activator of SHH signaling is SHH protein. In some embodiments, the at least one activator of SHH signaling is recombinant SHH protein. In some embodiments, the at least one activator of SHH signaling is recombinant mouse SHH protein. In some embodiments, the at least one activator of SHH signaling is recombinant human SHH protein. In some embodiments, the least one activator of SHH signaling is a recombinant N-Terminal fragment of a full-length murine sonic hedgehog protein capable of binding to the SHH receptor for activating SHH. In some embodiments, the at least one activator of SHH signaling is C25II SHH protein.

In some embodiments, cells are exposed to the at least one activator of SHH signaling at a concentration of between about 10 ng/mL and about 500 ng/mL, between about 20 ng/mL and 400 ng/mL, between about 30 ng/mL and about 300 ng/mL, between about 40 ng/mL and about 200 ng/mL, between about 50 ng/mL and 150 ng/mL, between about 50 ng/mL and about 100 ng/mL, or between about 75 ng/mL and 125 ng/mL, each inclusive. In some embodiments, cells are exposed to the at least one activator of SHH signaling at a concentration of between about 75 ng/mL and about 125 ng/mL, each inclusive. In some embodiments, cells are exposed to the at least one activator of SHH signaling at a concentration of between about 50 ng/mL and about 100 ng/mL, each inclusive. In some embodiments, cells are exposed to the at least one activator of SHH signaling at a concentration of at or about 100 ng/mL. In some embodiments, the cells are exposed to SHH protein at or about 100 ng/mL. In some embodiments, the cells are exposed to recombinant SHH protein at or about 100 ng/mL. In some embodiments, the cells are exposed to recombinant mouse SHH protein at or about 100 ng/mL. In some embodiments, the cells are exposed to C25II SHH protein at or about 100 ng/mL.

In some embodiments, cells are exposed to recombinant SHH protein at a concentration of at or about 100 ng/mL. In some embodiments, cells are exposed to recombinant SHH protein at a concentration of at or about 100 ng/mL beginning on Day 1 and up to about Day 7 (e.g., Day 6 or Day 7). In some embodiments, cells are exposed to recombinant SHH protein at a concentration of about 100 ng/mL from about Day 1 through about Day 6, inclusive of each day.

In some embodiments, cells are exposed to the at least one activator of SHH signaling at a concentration of between about 1 μM and about 20 μM, between about 5 μM and about 15 μM, or between about 8 μM and about 12 μM. In some embodiments, cells are exposed to the at least one activator of SHH signaling at a concentration of between about 1 μM and about 20 μM. In some embodiments, cells are exposed to the at least one activator of SHH signaling at a concentration of between about 5 μM and about 15 μM. In some embodiments, cells are exposed to the at least one activator of SHH signaling at a concentration of between about 8 μM and about 12 μM. In some embodiments, cells are exposed to the at least one activator of SHH signaling at a concentration of about 10 μM.

In some embodiments, the media is at least partially exchanged, and the media added on each of Days 1 through 6 by the media exchange includes at least one activator of SHH signaling at a concentration that is double the concentration of the at least one activator of SHH signaling that is intended to contact the cells, e.g., due to the media being added by a 50% media exchange.

In some embodiments, the media added by the media exchange, e.g., a 50% media exchange, on each of Days 1 through 6 comprises at least one activator of SHH signaling, e.g., SHH protein, at a concentration of between about 20 ng/mL and about 1 μg/mL, between about 40 ng/mL and 800 ng/mL, between about 60 ng/mL and about 600 ng/mL, between about about 80 ng/mL and about 400 ng/mL, between about 100 ng/mL and 300 ng/mL, between about 100 ng/mL and about 200 ng/mL, or between about 150 ng/mL and 250 ng/mL, each inclusive. In some embodiments, cells are exposed to the at least one activator of SHH signaling, e.g., SHH protein, at a concentration of between about 75 ng/mL and about 125 ng/mL, each inclusive. In some embodiments, the media added by the media exchange, e.g., a 50% media exchange, on each of Days 1 through 6 comprises at least one activator of SHH signaling, e.g., SHH protein, at a concentration of between about 150 ng/mL and about 250 ng/mL, each inclusive. In some embodiments, the media added by the media exchange, e.g., a 50% media exchange, on each of Days 1 through 6 comprises at least one activator of SHH signaling, e.g., SHH protein, at a concentration of between about 175 ng/mL and about 225 ng/mL, each inclusive. In some embodiments, the media added by the media exchange, e.g., a 50% media exchange, on each of Days 1 through 6 comprises at least one activator of SHH signaling, e.g., SHH protein, at a concentration of at or about 200 ng/mL.

In some embodiments, the at least one activator of SHH signaling is an activator of the Hedgehog receptor Smoothened. It some embodiments, the at least one activator of SHH signaling is a small molecule. In some embodiments, the least one activator of SHH signaling is purmorphamine (e.g., CAS 483367-10-8), having the formula below:

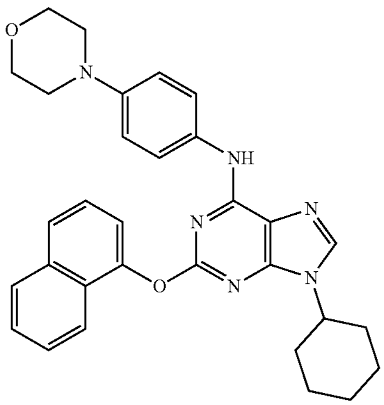 [SMILES: c1ccc2c(Oc3nc(Nc4ccc(N5CCOCC5)cc4)c4ncn(C5CCCCC5)c4n3)cccc2c1]

In some embodiments, cells are exposed to purmorphamine at a concentration of about 2 μM. In some embodiments, cells are exposed to purmorphamine at a concentration of about 2 μM beginning on Day 1 and up to Day 7 (e.g., Day 6 or Day 7). In some embodiments, cells are exposed to purmorphamine at a concentration of about 2 μM from about Day 1 through about Day 6, inclusive of each day.

In some embodiments, cells are exposed to purmorphamine at a concentration of between about 0.1 μM and about 20 μM, between about 0.5 μM and about 10 μM, between about 1 μM and about 5 μM, between about 1 μM and about 3 μM, or between about 1.5 μM and about 2.5 μM. In some embodiments, cells are exposed to purmorphamine at a concentration of about 2 μM.

In some embodiments, the media is at least partially exchanged, and the media added on each of Days 1 through 6 by the media exchange includes purmorphamine at a concentration that is double the concentration of the purmorphamine that is intended to contact the cells, e.g., due to the media being added by a 50% media exchange.

In some embodiments, the media added by the media exchange, e.g., a 50% media exchange, on each of Days 1 through 6 comprises purmorphamine at a concentration between about 0.2 μM and about 40 μM, between about 1 μM and about 20 μM, between about 2 μM and about 10 μM, between about 2 μM and about 6 μM, or between about 3 μM and about 5 μM. In some embodiments, the media added by the media exchange, e.g., a 50% media exchange, on each of Days 1 through 6 comprises purmorphamine at a concentration between about 3 μM and about 5 μM. In some embodiments, the media added by a 50% media exchange on each of Days 1 through 6 comprises purmorphamine at a concentration of about 4 μM.

In some embodiments, the at least one activator of SHH signaling is SHH protein and purmorphamine. In some embodiments, cells are exposed to SHH protein and purmorphamine beginning on Day 1 and up to about Day 7 (e.g., Day 6 or Day 7). In some embodiments, cells are exposed to SHH protein and purmorphamine from about Day 1 through about Day 6, inclusive of each day. In some embodiments, cells are exposed to about 100 ng/mL SHH protein and about 2 μM purmorphamine beginning on Day 1 and up to about Day 7 (e.g., Day 6 or Day 7). In some embodiments, cells are exposed to about 100 ng/mL SHH protein and about 2 μM purmorphamine from about Day 1 through about Day 6, inclusive of each day.

In some embodiments, there is a media exchange on each of Days 1 through 6. In some embodiments, the media exchange comprises replacing at or about 50% of the media. In some embodiments, the media exchange comprises replacing between about 25% and about 75% of the media. In some embodiments, from about Day 1 to about Day 6, between about 25% and about 75% of the media is replaced daily. In some embodiments, from about Day 1 to about Day 6, at least about 50% of the media is replaced daily. In some embodiments, from about Day 1 to about Day 6, about 50% of the media is replaced daily, every other day, or every third day. In some embodiments, from about Day 1 to about Day 6, about 50% of the media is replaced daily. In some embodiments, about 50% of the media is replaced on each of Days 1, 2, 3, 4, 5, and 6. Replacing about 50% of the media is also referred to herein as "a 50% media exchange." In some embodiments, the replacement media for each of Days 1 through 6 contains small molecules about twice as concentrated as compared to the concentration of the same small molecules in the media on Day 0.

In some embodiments, the first incubation comprises culturing pluripotent stem cells in a "basal induction media." In some embodiments, the first incubation comprises culturing pluripotent stem cells in the basal induction media from about Day 0 through about Day 6. In some embodiments, the first incubation comprises culturing pluripotent stem cells in the basal induction media to induce differentiation of the PSCs into floor plate midbrain progenitor cells.

In some embodiments, the basal induction media is formulated to contain Neurobasal™ media and DMEM/F12 media at a 1:1 ratio, supplemented with N-2 and B27 supplements, non-essential amino acids (NEAA), GlutaMAX™, L-glutamine, β-mercaptoethanol, and insulin. In some embodiments, the basal induction media is further supplemented with any of the small molecules as described above.

3. Transfer and/or Dissociation of Spheroids

In some embodiments, cell aggregates (e.g., spheroids) that are produced following the first incubation of culturing pluripotent stem cells in a non-adherent culture vessel are transferred or dissociated, prior to carrying out a second incubation of the cells under adherent culture.

In some embodiments, the first incubation is carried out to produce a cell aggregate (e.g., a spheroid) that expresses at least one of PAX6 and OTX2. In some embodiments, the first incubation produces a cell aggregate (e.g., a spheroid) that expresses PAX6 and OTX2. In some embodiments, the first incubation produces a cell aggregate (e.g., a spheroid) on or by about Day 7 of the methods provided herein. In some embodiments, the first incubation produces a cell aggregate (e.g., a spheroid) that expresses at least one of PAX6 and OTX2 on or by about Day 7 of the methods provided herein. In some embodiments, the first incubation produces a cell aggregate (e.g., a spheroid) that expresses PAX6 and OTX2 on or by about Day 7 of the methods provided herein.

In some embodiments, the cell aggregate (e.g., spheroid) produced by the first incubation is dissociated prior to the second incubation of the cells under adherent conditions. In some embodiments, the cell aggregate (e.g., spheroid) produced by the first incubation is dissociated to produce a cell suspension. In some embodiments, the cell suspension produced by the dissociation is a single cell suspension. In some embodiments, the dissociation is carried out at a time when the spheroid cells express at least one of PAX6 and OTX2. In some embodiments, the dissociation is carried out at a time when the spheroid cells express PAX6 and OTX2. In some embodiments, the dissociation is carried out on about Day 7. In some embodiments, the cell aggregate (e.g., spheroid) is dissociated by enzymatic dissociation. In some embodiments, the enzyme is selected from among the group consisting of: Accutase™, dispase, collagenase, and combinations thereof. In some embodiments, the enzyme comprises Accutase. In some embodiments, the enzyme is accutase. In some embodiments, the enzyme is dispase. In some embodiments, the enzyme is collagenase. In some embodiments, the enzyme is dispase and collagenase.

In some embodiments, the cell aggregate or cell suspension produced therefrom is transferred to a second culture vessel for a second incubation under adherent conditions. In some embodiments, the cell aggregate (e.g., spheroid) or cell suspension produced therefrom is transferred to a substrate-coated culture vessel following dissociation of the cell aggregate (e.g., spheroid). In some embodiments, the transferring is carried out immediately after the dissociating. In some embodiments, the transferring is carried out on about Day 7.

In some embodiments, the cell aggregate (e.g., spheroid) is not dissociated prior to a second incubation. In some embodiments, a cell aggregate (e.g., spheroid) is transferred in its entirety to a second culture vessel for a second incubation in which the cells adhere to the second culture vessel. In some embodiments, the transferring is carried out at a time when the spheroid cells express at least one of PAX6 and OTX2. In some embodiments, the transferring is carried out at a time when the spheroid cells express PAX6 and OTX2. In some embodiments, the transferring is carried out on about Day 7.

4. Adherent Culture

In some embodiments, the cell aggregate or cell suspension cells are subjected to a second incubation that is performed in adherent culture as shown in FIG. 1. The cell aggregate or cell suspension cells are transferred to a second culture vessel that is treated so that the cells adhere to the culture vessel. In some embodiments, the culture vessel is a plate, a dish, a flask, or a bioreactor. In some embodiments, the culture vessel is substrate-coated. In some embodiments, the substrate is a basement membrane protein. In some embodiments, the substrate is selected from laminin or a fragment thereof, collagen, entactin, heparin sulfate proteoglycans, and combinations thereof. In some embodiments, the substrate is laminin. In some embodiments, the substrate is recombinant. In some embodiments, the substrate is recombinant laminin or a fragment thereof. In some embodiments, the substrate is xeno-free. In some embodiments, the substrate is xeno-free laminin or a fragment thereof.

In some embodiments, the laminin or fragment thereof comprises an alpha chain, a beta chain, and a gamma chain. In some embodiments, the alpha chain is LAMA1, LAMA2, LAMA3, LAMA4, LAMA5, or a combination thereof. In some embodiments, the beta chain is LAMB1, LAMB2, LAMB3, LAMB4, or a combination thereof. In some embodiments, the gamma chain is LAMC1, LAMC2, LAMC3, or a combination thereof. In some embodiments, the laminin or a fragment thereof comprises any alpha, beta, and/or gamma chains as described in Aumailley, (2013) *Cell Adh Migra* 7(1):48-55.

In some embodiments, the laminin or a fragment thereof is selected from the group consisting of: laminin 111, laminin 121, laminin 211, laminin 213, laminin 221, laminin 3A32, laminin 3B32, laminin 3A11, laminin 3A21, laminin 411, laminin 421, laminin 423, laminin 511, laminin 521, laminin 522, laminin 523, or a fragment of any of the foregoing. In some embodiments, the laminin is selected from laminin 521, laminin 111, laminin 511, and laminin 511-E8. In some embodiments, the laminin or a fragment thereof comprises an E8 fragment of LAMA5, an E8 fragment of LAMB1, and an E8 fragment of LAMC1. In some embodiments, the laminin or a fragment thereof is laminin 511-E8 fragment. See Miyazaki et al. (2012) Nat Commun 3:1236. In some embodiments, the substrate-coated culture vessel is exposed to poly-L-ornithine, optionally prior to being used for culturing cells.

In some embodiments, the substrate-coated culture vessel is a plate, a dish, a flask, or a bioreactor. In some embodiments, the substrate-coated culture vessel is a 6-well, 12-well, or 24-well plate. In some embodiments, the substrate-coated culture vessel is a 6-well plate. In some embodiments, the substrate-coated culture vessel is a 12-well plate. In some embodiments, the substrate-coated culture vessel is a 24-well plate.

In some embodiments, the methods include performing a second incubation of the spheroid cells transferred to a second culture vessel and subjected to culture under adherent conditions. In some embodiments, culturing the cells of the spheroid under adherent conditions induces their differentiation into floor plate midbrain progenitor cells, dopaminergic neuronal progenitor cells, including determined dopaminergic neuronal progenitor cells, committed dopaminergic neuronal progenitor cells and/or, dopaminergic neuronal cells.

In some embodiments, the second incubation involves culturing cells of the spheroid in a second culture vessel that is coated with a substrate that promotes adhesion of the cells to the culture vessel. Beginning when the cells are placed in the second culture vessel, typically on Day 7, the cells are exposed to (i) an inhibitor of BMP signaling and (ii) an inhibitor of GSK3β signaling; and beginning on Day 11, the cells are exposed to (i) brain-derived neurotrophic factor (BDNF); (ii) ascorbic acid; (iii) glial cell-derived neurotrophic factor (GDNF); (iv) dibutyryl cyclic AMP (db-cAMP); (v) transforming growth factor beta-3 (TGFβ3); and (vi) an inhibitor of Notch signaling.

In some embodiments, the second culture vessel allows for a monolayer cell culture. In some embodiments, cells derived from the cell aggregate (e.g., spheroid) produced by the first incubation are cultured in a monolayer culture on the second culture vessel. In some embodiments, cells derived from the cell aggregate (e.g., spheroid) produced by the first incubation are cultured to produce a monolayer culture of cells positive for one or more of LMX1A, FOXA2, EN1, CORIN, and combinations thereof. In some embodiments, cells derived from the cell aggregate (e.g., spheroid) produced by the first incubation are cultured to produce a monolayer culture of cells, wherein at least some of the cells are positive for EN1 and CORIN. In some embodiments, cells derived from the cell aggregate (e.g., spheroid) produced by the first incubation are cultured to produce a monolayer culture of cells, wherein at least some of the cells are positive for EN1. In some embodiments, cells derived from the cell aggregate (e.g., spheroid) produced by the first incubation are cultured to produce a monolayer culture of cells, wherein at least some of the cells are TH+. In some embodiments, at least some cells are TH+ by or on about Day 16. In some embodiments, cells derived from the cell aggregate (e.g., spheroid) produced by the first incubation are cultured to produce a monolayer culture of cells, wherein at least some of the cells are TH+FOXA2+. In some embodiments, at least some cells are TH+FOXA2+ by or on about Day 16.

In the methods provided herein, the second incubation involves culturing cells of the spheroid in a second culture vessel under conditions to induce neural differentiation of the cells. In some embodiments, the cells of the spheroid are plated on the second culture vessel on about Day 7.

In some embodiments, the number of cells plated on the second culture vessel is between about $0.1\times10^6$ cells/$cm^2$ and about $2\times10^6$ cells/$cm^2$, between about $0.1\times10^6$ cells/$cm^2$ and about $1.5\times10^6$ cells/$cm^2$, between about $0.1\times10^6$ cells/$cm^2$ and about $1\times10^6$ cells/$cm^2$, between about $0.1\times10^6$ cells/$cm^2$ and about $0.8\times10^6$ cells/$cm^2$, between about $0.2\times10^6$ cells/$cm^2$ and about $2\times10^6$ cells/$cm^2$, between about $0.2\times10^6$ cells/$cm^2$ and about $1.5\times10^6$ cells/$cm^2$, between about $0.2\times10^6$ cells/$cm^2$ and about $1\times10^6$ cells/$cm^2$, between about $0.2\times10^6$ cells/$cm^2$ and about $0.8\times10^6$ cells/$cm^2$, between about $0.4\times10^6$ cells/$cm^2$ and about $2\times10^6$ cells/$cm^2$, between about $0.4\times10^6$ cells/$cm^2$ and about $1.5\times10^6$ cells/$cm^2$, between about $0.4\times10^6$ cells/$cm^2$ and about $1\times10^6$ cells/$cm^2$, between about $0.4\times10^6$ cells/$cm^2$ and about $0.8\times10^6$ cells/$cm^2$, between about $0.6\times10^6$ cells/$cm^2$ and about $2\times10^6$ cells/$cm^2$, between about $0.6\times10^6$ cells/$cm^2$ and about $1.5\times10^6$ cells/$cm^2$, between about $0.6\times10^6$ cells/$cm^2$ and about $1\times10^6$ cells/$cm^2$, between about $0.6\times10^6$ cells/$cm^2$ and about $0.8\times10^6$ cells/$cm^2$, between about $0.8\times10^6$ cells/$cm^2$ and about $2\times10^6$ cells/$cm^2$, or between about $0.8\times10^6$ cells/$cm^2$ and about $1\times10^6$ cells/$cm^2$. In some embodiments, the number of cells plated on the second culture vessel is between about $0.6\times10^6$ cells/$cm^2$ and about $1.0\times10^6$ cells/$cm^2$. In some embodiments, the number of cells plated on the second culture vessel is at or about $0.8\times10^6$ cells/$cm^2$.

In some embodiments, the second incubation involves culturing cells derived from the cell aggregate (e.g., spheroid) in a culture media ("media").

In some embodiments, the second incubation involves culturing the cells derived from the cell aggregate in the media from about Day 7 until harvest or collection. In some embodiments, the media is at least partially exchanged on each day beginning on Day 8 until harvest or collection. In the media exchange, new media replaces the media added on the prior day, e.g., there is a complete or near complete replacement or exchange of the media on each of these days. In some embodiments, cells are cultured in the media to produce determined dopaminergic neuronal progenitor cells, committed dopaminergic neuronal progenitor cells or dopaminergic neuronal cells.

In some embodiments, the media is also supplemented with a serum replacement containing minimal non-human-derived components (e.g., KnockOut™ serum replacement). In some embodiments, the media is supplemented with the serum replacement from about Day 7 through about Day 10. In some embodiments, the media is supplemented with about 2% (v/v) of the serum replacement. In some embodiments, the media is supplemented with about 2% (v/v) of the serum replacement from about Day 7 through about Day 10.

In some embodiments, the media is further supplemented with small molecules. In some embodiments, the small molecules are selected from among the group consisting of: a Rho-associated protein kinase (ROCK) inhibitor, an inhibitor of bone morphogenetic protein (BMP) signaling, an inhibitor of glycogen synthase kinase 3β (GSK3β) signaling, and combinations thereof.

In some embodiments the media is supplemented with a Rho-associated protein kinase (ROCK) inhibitor on one or more days when cells are passaged. In some embodiments, the cells are passaged on or about Day 7. In some embodiments the media is supplemented with a ROCK inhibitor each day that cells are passaged, e.g., on Day 7. In some embodiments the media is supplemented with a ROCK inhibitor on Day 7.

In some embodiments, cells are exposed to the ROCK inhibitor at a concentration of between about 1 μM and about 20 μM, between about 5 μM and about 15 μM, or between about 8 μM and about 12 μM. In some embodiments, cells are exposed to the ROCK inhibitor at a concentration of between about 1 μM and about 20 μM. In some embodiments, cells are exposed to the ROCK inhibitor at a concentration of between about 5 μM and about 15 μM. In some embodiments, cells are exposed to the ROCK inhibitor at a concentration of between about 8 μM and about 12 μM. In some embodiments, cells are exposed to the ROCK inhibitor at a concentration of at or about 10 μM. In some embodiments, cells are exposed to Y-27632 at a concentration of about 10 μM. In some embodiments, cells are exposed to Y-27632 at a concentration of at or about 10 μM on Day 7.

In some embodiments the media is supplemented with an inhibitor of BMP signaling. In some embodiments the media is supplemented with an inhibitor of BMP signaling from about Day 7 up to about Day 11 (e.g., up to Day 10 or Day 11). In some embodiments the media is supplemented with an inhibitor of BMP signaling from about Day 7 through Day 10, each day inclusive.

In some embodiments, cells are exposed to the inhibitor of BMP signaling at a concentration of between about 0.01 μM and about 5 μM, between about 0.05 μM and about 1 μM, between about 0.05 μM and about 0.2 μM, or between about 0.1 μM and about 0.5 μM, each inclusive. In some embodiments, cells are exposed to the inhibitor of BMP signaling at a concentration of between about 0.01 μM and about 5 μM. In some embodiments, cells are exposed to the inhibitor of BMP signaling at a concentration of between about 0.05 μM and about 1 μM. In some embodiments, cells are exposed to the inhibitor of BMP signaling at a concentration of between about 0.05 μM and about 0.2 μM. In some embodiments, cells are exposed to the inhibitor of BMP signaling at a concentration of about 0.1 μM. In some embodiments, cells are exposed to LDN193189 at a concentration of about 0.1 μM. In some embodiments, cells are exposed to LDN193189 at a concentration of about 0.1 μM from about Day 7 up to about Day 11 (e.g., Day 10 or Day 11). In some embodiments, cells are exposed to LDN193189 at a concentration of about 0.1 μM from about Day 7 through about Day 10, inclusive of each day.

In some embodiments the media is supplemented with an inhibitor of GSK3β signaling. In some embodiments the media is supplemented with an inhibitor of GSK3β signaling from about Day 7 up to about Day 13 (e.g., Day 12 or Day 13). In some embodiments the media is supplemented with an inhibitor of GSK3β signaling from about Day 7 through Day 12, each day inclusive.

In some embodiments, cells are exposed to the inhibitor of GSK3β signaling at a concentration of between about 0.1 μM and about 10 μM, between about 0.5 μM and about 8 μM, or between about 1 μM and about 4 μM, between about 1.5 μM and about 3 μM, or between about 1.5 μM and about 2.5 μM, each inclusive. In some embodiments, cells are exposed to the inhibitor of GSK3β signaling at a concentration of between about 0.1 μM and about 10 μM. In some embodiments, cells are exposed to the inhibitor of GSK3β signaling at a concentration of between about 0.5 μM and about 8 μM. In some embodiments, cells are exposed to the inhibitor of GSK3β signaling at a concentration of between about 1 μM and about 4 μM. In some embodiments, cells are exposed to the inhibitor of GSK3β signaling at a concentration of between about 1.5 μM and about 3 μM. In some embodiments, cells are exposed to the inhibitor of GSK3β signaling at a concentration of about 2 μM. In some embodiments, cells are exposed to CHIR99021 at a concentration of about 2.0 μM. In some embodiments, cells are exposed to CHIR99021 at a concentration of about 2.0 μM from about Day 7 up to about Day 13 (e.g., up to Day 12 or Day 13). In some embodiments, cells are exposed to CHIR99021 at a concentration of about 2.0 μM from about Day 7 through about Day 12, inclusive of each day.

In some embodiments the media is supplemented with brain-derived neurotrophic factor (BDNF). In some embodiments the media is supplemented with BDNF beginning on about Day 11. In some embodiments the media is supplemented with BDNF from about Day 11 until harvest or collection. In some embodiments the media is supplemented with BDNF from about Day 11 through about Day 14, 15, 16, or 17. In some embodiments the media is supplemented with BDNF from about Day 11 through Day 14. In some embodiments the media is supplemented with BDNF from about Day 11 through Day 15. In some embodiments the media is supplemented with BDNF from about Day 11 through Day 16. In some embodiments the media is supplemented with BDNF from about Day 11 through Day 17.

In some embodiments, cells are exposed to BDNF at a concentration of between about 1 ng/mL and 100 ng/mL, between about 5 ng/mL and about 50 ng/mL, between about 10 ng/mL and about 30 ng/mL. In some embodiments, cells are exposed to BDNF at a concentration of between about 10 ng/mL and about 30 ng/mL. In some embodiments, cells are exposed to BDNF at a concentration of about 20 ng/mL.

In some embodiments, the media is supplemented with about 20 ng/mL BDNF beginning on about Day 11. In some embodiments the media is supplemented with 20 ng/mL BDNF from about Day 11 until harvest or collection. In some embodiments the media is supplemented with about 20 ng/mL BDNF from about Day 11 through about Day 14, 15, 16, or 17. In some embodiments the media is supplemented with about 20 ng/mL BDNF from about Day 11 through Day 14. In some embodiments the media is supplemented with about 20 ng/mL BDNF from about Day 11 through Day 15. In some embodiments the media is supplemented with about 20 ng/mL BDNF from about Day 11 through Day 16. In some embodiments the media is supplemented with about 20 ng/mL BDNF from about Day 11 through Day 17.

In some embodiments the media is supplemented with glial cell-derived neurotrophic factor (GDNF). In some embodiments the media is supplemented with GDNF beginning on about Day 11. In some embodiments the media is supplemented with GDNF from about Day 11 until harvest or collection. In some embodiments the media is supplemented with GDNF from about Day 11 through about Day 14, 15, 16, or 17. In some embodiments the media is supplemented with GDNF from about Day 11 through Day 14. In some embodiments the media is supplemented with GDNF from about Day 11 through Day 15. In some embodiments the media is supplemented with GDNF from about Day 11 through Day 16. In some embodiments the media is supplemented with GDNF from about Day 11 through Day 17.

In some embodiments, cells are exposed to GDNF at a concentration of between about 1 ng/mL and 100 ng/mL, between about 5 ng/mL and about 50 ng/mL, between about 10 ng/mL and about 30 ng/mL. In some embodiments, cells are exposed to GDNF at a concentration of between about 10 ng/mL and about 30 ng/mL. In some embodiments, cells are exposed to GDNF at a concentration of about 20 ng/mL.

In some embodiments, the media is supplemented with about 20 ng/mL GDNF beginning on about Day 11. In some embodiments the media is supplemented with 20 ng/mL GDNF from about Day 11 until harvest or collection. In some embodiments the media is supplemented with about 20 ng/mL GDNF from about Day 11 through about Day 14, 15, 16, or 17. In some embodiments the media is supplemented with about 20 ng/mL GDNF from about Day 11 through Day 14. In some embodiments the media is supplemented with about 20 ng/mL GDNF from about Day 11 through Day 15. In some embodiments the media is supplemented with about 20 ng/mL GDNF from about Day 11 through Day 16. In some embodiments the media is supplemented with about 20 ng/mL GDNF from about Day 11 through Day 17.

In some embodiments the media is supplemented with ascorbic acid. In some embodiments the media is supplemented with ascorbic acid beginning on about Day 11. In some embodiments the media is supplemented with ascorbic acid from about Day 11 until harvest or collection. In some embodiments the media is supplemented with ascorbic acid from about Day 11 through about Day 14, 15, 16, or 17. In some embodiments the media is supplemented with ascorbic acid from about Day 11 through Day 14. In some embodiments the media is supplemented with ascorbic acid from about Day 11 through Day 15. In some embodiments the media is supplemented with ascorbic acid from about Day 11 through Day 16. In some embodiments the media is supplemented with ascorbic acid from about Day 11 through Day 17.

In some embodiments, cells are exposed to ascorbic acid at a concentration of between about 0.05 mM and 5 mM, between about 0.1 mM and about 1 mM, between about 0.2 mM and about 0.5 mM, each inclusive. In some embodiments, cells are exposed to ascorbic acid at a concentration of between about 0.05 mM and about 5 mM, each inclusive. In some embodiments, cells are exposed to ascorbic acid at a concentration of between about 0.1 mM and about 1 mM, each inclusive. In some embodiments, cells are exposed to ascorbic acid at a concentration of about 0.2 mM.

In some embodiments, the media is supplemented with about 0.2 mM ascorbic acid beginning on about Day 11. In some embodiments the media is supplemented with 0.2 mM ascorbic acid from about Day 11 until harvest or collection. In some embodiments the media is supplemented with about 0.2 mM ascorbic acid from about Day 11 through about Day 14, 15, 16, or 17. In some embodiments the media is supplemented with about 0.2 mM ascorbic acid from about Day 11 through Day 14. In some embodiments the media is supplemented with about 0.2 mM ascorbic acid from about Day 11 through Day 15. In some embodiments the media is supplemented with about 0.2 mM ascorbic acid from about Day 11 through Day 16. In some embodiments the media is supplemented with about 0.2 mM ascorbic acid from about Day 11 through Day 17.

In some embodiments the media is supplemented with dibutyryl cyclic AMP (dbcAMP). In some embodiments the media is supplemented with dbcAMP beginning on about Day 11. In some embodiments the media is supplemented with dbcAMP from about Day 11 until harvest or collection. In some embodiments the media is supplemented with dbcAMP from about Day 11 through about Day 14, 15, 16, or 17. In some embodiments the media is supplemented with dbcAMP from about Day 11 through Day 14. In some embodiments the media is supplemented with dbcAMP from about Day 11 through Day 15. In some embodiments the media is supplemented with dbcAMP from about Day 11 through Day 16. In some embodiments the media is supplemented with dbcAMP from about Day 11 through Day 17.

In some embodiments, cells are exposed to dbcAMP at a concentration of between about 0.05 mM and 5 mM, between about 0.1 mM and about 3 mM, between about 0.2 mM and about 1 mM, each inclusive. In some embodiments, cells are exposed to dbcAMP at a concentration of between about 0.1 mM and about 3 mM, each inclusive. In some embodiments, cells are exposed to dbcAMP at a concentration of between about 0.2 mM and about 1 mM, each inclusive. In some embodiments, cells are exposed to dbcAMP at a concentration of about 0.5 mM.

In some embodiments, the media is supplemented with about 0.5 mM dbcAMP beginning on about Day 11. In some embodiments the media is supplemented with 0.5 mM dbcAMP from about Day 11 until harvest or collection. In some embodiments the media is supplemented with about 0.5 mM dbcAMP from about Day 11 through about Day 14, 15, 16, or 17. In some embodiments the media is supplemented with about 0.5 mM dbcAMP from about Day 11 through Day 14. In some embodiments the media is supplemented with about 0.5 mM dbcAMP from about Day 11 through Day 15. In some embodiments the media is supplemented with about 0.5 mM dbcAMP from about Day 11 through Day 16. In some embodiments the media is supplemented with about 0.5 mM dbcAMP from about Day 11 through Day 17.

In some embodiments the media is supplemented with transforming growth factor beta 3 (TGFβ3). In some embodiments the media is supplemented with TGFβ3 beginning on about Day 11. In some embodiments the media is supplemented with TGFβ3 from about Day 11 until harvest or collection. In some embodiments the media is supplemented with TGFβ3 from about Day 11 through about Day 14, 15, 16, or 17. In some embodiments the media is supplemented with TGFβ3 from about Day 11 through Day 14. In some embodiments the media is supplemented with TGFβ3 from about Day 11 through Day 15. In some embodiments the media is supplemented with TGFβ3 from about Day 11 through Day 16. In some embodiments the media is supplemented with TGFβ3 from about Day 11 through Day 17.

In some embodiments, cells are exposed to TGFβ3 at a concentration of between about 0.1 ng/mL and 10 ng/mL, between about 0.5 ng/mL and about 5 ng/mL, or between about 1.0 ng/mL and about 2.0 ng/mL. In some embodiments, cells are exposed to TGFβ3 at a concentration of between about 1.0 ng/mL and about 2.0 ng/mL, each inclusive. In some embodiments, cells are exposed to TGFβ3 at a concentration of about 1 ng/mL.

In some embodiments, the media is supplemented with about 1 ng/mL TGFβ3 beginning on about Day 11. In some embodiments the media is supplemented with 1 ng/mL TGFβ3 from about Day 11 until harvest or collection. In some embodiments the media is supplemented with about 1 ng/mL TGFβ3 from about Day 11 through about Day 14, 15, 16, or 17. In some embodiments the media is supplemented with about 1 ng/mL TGFβ3 from about Day 11 through Day 14. In some embodiments the media is supplemented with about 1 ng/mL TGFβ3 from about Day 11 through Day 15. In some embodiments the media is supplemented with about 1 ng/mL TGFβ3 from about Day 11 through Day 16. In some embodiments the media is supplemented with about 1 ng/mL TGFβ3 from about Day 11 through Day 17.

In some embodiments the media is supplemented with an inhibitor of Notch signaling. In some embodiments the media is supplemented with an inhibitor of Notch signaling beginning on about Day 11. In some embodiments the media is supplemented with an inhibitor of Notch signaling from about Day 11 until harvest or collection. In some embodiments the media is supplemented with an inhibitor of Notch signaling from about Day 11 through about Day 14, 15, 16, or 17. In some embodiments the media is supplemented with an inhibitor of Notch signaling from about Day 11 through Day 14. In some embodiments the media is supplemented with an inhibitor of Notch signaling from about Day 11 through Day 15. In some embodiments the media is supplemented with an inhibitor of Notch signaling from about Day 11 through Day 16. In some embodiments the media is supplemented with an inhibitor of Notch signaling from about Day 11 through Day 17.

In some embodiments, an inhibitor of Notch signaling is selected from cowanin, PF-03084014, L685458, LY3039478, DAPT, or a combination thereof. In some embodiments, the inhibitor of Notch signaling inhibits gamma secretase. In some embodiments, the inhibitor of Notch signaling is a small molecule. In some embodiments, the inhibitor of Notch signaling is DAPT, having the following formula:

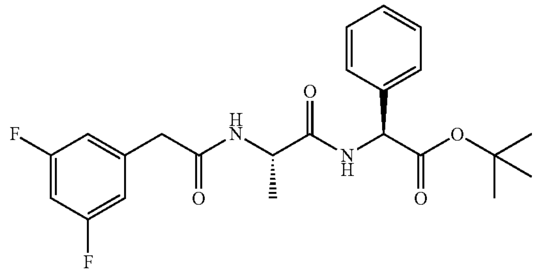 [SMILES: C[C@H](NC(=O)Cc1cc(F)cc(F)c1)C(=O)N[C@H](C(=O)OC(C)(C)C)c1ccccc1]

In some embodiments, cells are exposed to DAPT at a concentration of between about 1 μM and about 20 μM, between about 5 μM and about 15 μM, or between about 8 μM and about 12 μM. In some embodiments, cells are exposed to DAPT at a concentration of between about 1 μM and about 20 μM. In some embodiments, cells are exposed to DAPT at a concentration of between about 5 μM and about 15 μM. In some embodiments, cells are exposed to DAPT at a concentration of between about 8 μM and about 12 μM. In some embodiments, cells are exposed to DAPT at a concentration of about 10 μM.

In some embodiments, the media is supplemented with about 10 μM DAPT beginning on about Day 11. In some embodiments the media is supplemented with 10 μM DAPT from about Day 11 until harvest or collection. In some embodiments the media is supplemented with about 10 μM DAPT from about Day 11 through about Day 14, 15, 16, or 17. In some embodiments the media is supplemented with about 10 μM DAPT from about Day 11 through Day 14. In some embodiments the media is supplemented with about 10 μM DAFT from about Day 11 through Day 15. In some embodiments the media is supplemented with about 10 μM DAFT from about Day 11 through Day 16. In some embodiments the media is supplemented with about 10 μM DAFT from about Day 11 through Day 17.

In some embodiments, beginning on about Day 11, the media is supplemented with about 20 ng/mL BDNF, about 20 ng/mL GDNF, about 0.2 mM ascorbic acid, about 0.5 mM dbcAMP, about 1 ng/mL TGFβ3, and about 10 μM DAFT. In some embodiments, from about Day 11 until harvest or collection, the media is supplemented with about 20 ng/mL BDNF, about 20 ng/mL GDNF, about 0.2 mM ascorbic acid, about 0.5 mM dbcAMP, about 1 ng/mL TGFβ3, and about 10 μM DAFT. In some embodiments, from about Day 11 until about Day 14, 15, 16, or 17, the media is supplemented with about 20 ng/mL BDNF, about 20 ng/mL GDNF, about 0.2 mM ascorbic acid, about 0.5 mM dbcAMP, about 1 ng/mL TGFβ3, and about 10 μM DAFT. In some embodiments, from about Day 11 until Day 14, the media is supplemented with about 20 ng/mL BDNF, about 20 ng/mL GDNF, about 0.2 mM ascorbic acid, about 0.5 mM dbcAMP, about 1 ng/mL TGFβ3, and about 10 μM DAFT. In some embodiments, from about Day 11 until Day 15, the media is supplemented with about 20 ng/mL BDNF, about 20 ng/mL GDNF, about 0.2 mM ascorbic acid, about 0.5 mM dbcAMP, about 1 ng/mL TGFβ3, and about 10 μM DAFT. In some embodiments, from about Day 11 until Day 16, the media is supplemented with about 20 ng/mL BDNF, about 20 ng/mL GDNF, about 0.2 mM ascorbic acid, about 0.5 mM dbcAMP, about 1 ng/mL TGFβ3, and about 10 μM DAFT. In some embodiments, from about Day 11 until Day 17, the media is supplemented with about 20 ng/mL BDNF, about 20 ng/mL GDNF, about 0.2 mM ascorbic acid, about 0.5 mM dbcAMP, about 1 ng/mL TGFβ3, and about 10 μM DAFT.

In some embodiments, a serum replacement is provided in the media from about Day 7 through about Day 10. In some embodiments, the serum replacement is provided at 2% (v/v) in the media on Day 7 through Day 10.

In some embodiments, from about Day 7 to harvest or collection, e.g., about Day 14, 15, 16, or 17, the media is replaced daily. In some embodiments, from Day about 7 to harvest or collection, e.g., about Day 14, 15, 16, or 17, at least 90%, 91%, 92%, 93%, 94%, 95%, 96%, 97%, 98%, or 99% of the media is replaced daily. In some embodiments, from Day about 7 to harvest or collection, e.g., about Day 14, 15, 16, or 17, at least 95%, 96%, 97%, 98%, or 99% of the media is replaced daily. In some embodiments, from about Day 7 to harvest or collection, e.g., about Day 14, 15, 16, or 17, at least 98% or 99% of the media is replaced daily.

In some embodiments, the second incubation involves culturing cells derived from the cell aggregate (e.g., spheroid) in a "basal induction media." In some embodiments, the second incubation involves culturing cells derived from the cell aggregate (e.g., spheroid) in a "maturation media." In some embodiments, the second incubation involves culturing cells derived from the cell aggregate (e.g., spheroid) in the basal induction media, and then in the maturation media.

In some embodiments, the second incubation involves culturing the cells in the basal induction media from about Day 7 through about Day 10. In some embodiments, the second incubation involves culturing the cells in the maturation media beginning on about Day 11. In some embodiments, the second incubation involves culturing the cells in the basal induction media from about Day 7 through about Day 10, and then in the maturation media beginning on about Day 11. In some embodiments, the second incubation involves culturing the cells in the basal induction media from about Day 7 through about Day 10, and then in the maturation media beginning on about Day 11 until collection or harvest. In some embodiments, cells are cultured in the maturation media to produce determined dopaminergic neuronal progenitor cells, committed dopaminergic neuronal progenitor cells, and/or dopaminergic neuronal cells.

In some embodiments, the basal induction media is formulated to contain Neurobasal™ media and DMEM/F12 media at a 1:1 ratio, supplemented with N-2 and B27 supplements, non-essential amino acids (NEAA), GlutaMAX™, L-glutamine, β-mercaptoethanol, and insulin. In some embodiments, the basal induction media is further supplemented with any of the molecules described in Section B.

In some embodiments, the maturation media is formulated to contain Neurobasal™ media, supplemented with N-2 and B27 supplements, non-essential amino acids (NEAA), and GlutaMAX™. In some embodiments, the maturation media is further supplemented with any of the molecules described in Section B.

In some embodiments, the cells are cultured in the basal induction media from about Day 7 up to about Day 11 (e.g., Day 10 or Day 11). In some embodiments, the cells are cultured in the basal induction media from about Day 7 through Day 10, each day inclusive. In some embodiments, the cells are cultured in the maturation media beginning on about Day 11. In some embodiments, the cells are cultured in the basal induction media from about Day 7 through about Day 10, and then the cells are cultured in the maturation media beginning on about Day 11. In some embodiments, the cells are cultured in the maturation media from about Day 11 until harvest or collection of the cells.

In some embodiments, the second incubation is from about Day 7 until harvesting of the cells. In some embodiments, the method further includes harvesting the differentiated cells. In some embodiments, the differentiated cells are harvested between about Day 14 and about Day 17. In some embodiments, the differentiated cells are harvested on or about Day 14, Day 15, Day 16, or Day 17. In some embodiments, the differentiated cells are harvested on or about Day 14. In some embodiments, the differentiated cells are harvested on or about Day 15. In some embodiments, the differentiated cells are harvested on or about Day 16. In some embodiments, the differentiated cells are harvested on or about Day 17. In some embodiments, the second incubation is from about Day 7 until about Day 14. In some embodiments, the second incubation is from about Day 7 until about Day 15. In some embodiments, the second incubation is from about Day 7 until about Day 16. In some embodiments, the second incubation is from about Day 7 until about Day 17.

5. Harvesting, Collecting, and Formulating Differentiated Cells

In embodiments of the provided methods, neutrally differentiated cells produced by the methods provided herein can be harvested or collected, such as for formulation and use of the cells. In some embodiments, the provided methods for producing differentiated cells, such as for use as a cell therapy in the treatment of a neurodegenerative disease may include formulation of cells, such as formulation of differentiated cells resulting from the provided methods described herein. In some embodiments, the dose of cells comprising differentiated cells (e.g., determined DA neuronal progenitor cells, committed dopaminergic neuronal progenitor cells, or dopaminergic neuronal cells), is provided as a composition or formulation, such as a pharmaceutical composition or formulation. Such compositions can be used in accord with the provided methods, such as in the prevention or treatment of neurodegenerative disorders, including Parkinson's disease.

In some cases, the cells are processed in one or more steps for manufacturing, generating or producing a cell therapy and/or differentiated cells may include formulation of cells, such as formulation of differentiated cells resulting from the methods. In some cases, the cells can be formulated in an amount for dosage administration, such as for a single unit dosage administration or multiple dosage administration.

In certain embodiments, one or more compositions of differentiated cells are formulated. In particular embodiments, one or more compositions of differentiated cells are formulated after the one or more compositions have been produced. In some embodiments, the one or more compositions have been previously cryopreserved and stored, and are thawed prior to the administration.

In certain embodiments, the differentiated cells include dopaminergic neuronal progenitor cells, including determined dopaminergic neuronal progenitor cells. In some embodiments, a formulated composition of differentiated cells is a composition enriched for determined DA neuronal progenitor cells. In certain embodiments, the differentiated cells include committed dopaminergic neuronal progenitor cells. In some embodiments, a formulated composition of differentiated cells is a composition enriched for committed dopaminergic neuronal progenitor cells. In certain embodiments, the differentiated cells include dopaminergic neuronal cells. In some embodiments, a formulated composition of differentiated cells is a composition enriched for dopaminergic neuronal cells.

6. Exemplary Processes

As described by the methods provided herein, pluripotent stem cells may be differentiated into lineage specific cell populations, including determined DA progenitors cells and DA neurons. These cells may then be used in cell replacement therapy. As described by the methods here, in some embodiments, the pluripotent stem cells are differentiated into floor plate midbrain progenitor cells, and the resulting spheroid cells are further differentiated into determined dopaminergic neuronal progenitor cells, committed dopaminergic neuronal progenitor cells, and/or dopaminergic neuronal cells. In some embodiments, the pluripotent stem cells are differentiated into determined DA neuron progenitor cells. In some embodiments, the pluripotent stem cells are differentiated into DA neurons. In some embodiments, pluripotent stem cells are embryonic stem cells, e.g., isolated embryonic stem cells. In some embodiments, pluripotent stem cells are induced pluripotent stem cells.

In some embodiments, embryonic stem cells, e.g., isolated embryonic stem cells, are differentiated into floor plate midbrain progenitor cells, and then into determined dopaminergic neuronal progenitor cells, committed dopaminergic neuronal progenitor cells, and/or dopaminergic neuronal cells. In some embodiments, embryonic stem cells, e.g., isolated embryonic stem cells, are differentiated into determined dopaminergic neuronal progenitor cells. In some embodiments, embryonic stem cells, e.g., isolated embryonic stem cells, are differentiated into committed dopaminergic neuronal progenitor cells. In some embodiments, embryonic stem cells, e.g., isolated embryonic stem cells, are differentiated into dopaminergic neuronal cells.

In some embodiments, induced pluripotent stem cells are differentiated into floor plate midbrain progenitor cells, and then into determined dopaminergic neuronal progenitor cells, committed dopaminergic neuronal progenitor cells, and/or dopaminergic neuronal cells. In some embodiments, induced pluripotent stem cells are differentiated into determined dopaminergic neuronal progenitor cells. In some embodiments, induced pluripotent stem cells are differentiated into committed dopaminergic neuronal progenitor cells. In some embodiments, induced pluripotent stem cells are differentiated into dopaminergic neuronal cells.

In some embodiments, the method involves (a) performing a first incubation including culturing pluripotent stem cells in a non-adherent culture vessel under conditions to produce a cellular spheroid, wherein (i) starting on the first day (Day 0) of the first incubation, the cells are exposed to an inhibitor of TGF-β/activin-Nodal signaling, and an inhibitor of bone morphogenetic protein (BMP) signaling; and (ii) starting on the second day of the first incubation (Day 1), the cells are exposed to at least one activator of Sonic Hedgehog (SHH) signaling, and an inhibitor of glycogen synthase kinase 3β (GSK3β) signaling; and (b) performing a second incubation including culturing cells of the spheroid in a substrate-coated culture vessel under conditions to induce neural differentiation of the cells. In some embodiments, the Day 0 incubation is done in the absence of (x) an activator of Sonic Hedgehog (SHH) signaling, and (y) an inhibitor of glycogen synthase kinase 3β signaling. These methods are sometimes referred to herein as the "Day 1" suspension culture differentiation protocol due to the first exposure of the cells to the SHH activator and the GSK3β signaling inhibitor on Day 1 (the second day) of the first incubation.

In some embodiments, culturing the cells under conditions to induce neural differentiation of the cells involves exposing the cells to (i) brain-derived neurotrophic factor (BDNF); (ii) ascorbic acid; (iii) glial cell-derived neurotrophic factor (GDNF); (iv) dibutyryl cyclic AMP (dbcAMP); (v) transforming growth factor beta-3 (TGFβ3); and (vi) an inhibitor of Notch signaling.

In some embodiments, the method involves (a) performing a first incubation including culturing pluripotent stem cells in a plate having microwells under conditions to produce a cellular spheroid, wherein (i) starting on the first day (Day 0) of the first incubation, the cells are exposed to an inhibitor of TGF-β/activin-Nodal signaling, an inhibitor of bone morphogenetic protein (BMP) signaling, and a serum replacement; and (ii) starting on the second day of the first incubation (Day 1), the cells are exposed to at least one activator of Sonic Hedgehog (SHH) signaling, an inhibitor of glycogen synthase kinase 3β (GSK3β) signaling, and serum replacement; (b) dissociating the cells of the spheroid to produce a cell suspension; (c) transferring cells of the cell suspension to a laminin-coated culture vessel; (d) performing a second incubation including culturing cells of the spheroid in the laminin-coated culture vessel under conditions to induce neural differentiation of the cells; and (e) harvesting the neurally differentiated cells. In some embodiments, the Day 0 incubation is done in the absence of (x) an activator of Sonic Hedgehog (SHH) signaling, and (y) an inhibitor of glycogen synthase kinase 33 signaling. In some embodiments, the second incubation involves culturing cells in the presence of a serum replacement. In some embodiments, culturing the cells under conditions to induce neural differentiation of the cells involves exposing the cells to (i) brain-derived neurotrophic factor (BDNF); (ii) ascorbic acid; (iii) glial cell-derived neurotrophic factor (GDNF); (iv) dibutyryl cyclic AMP (dbcAMP); (v) transforming growth factor beta-3 (TGFβ3); and (vi) an inhibitor of Notch signaling.

In some embodiments, the cells are exposed to the inhibitor of TGF-β/activin-Nodal (e.g., SB431542 or "SB") from Day 0 up to about Day 5 (e.g., Day 4 or Day 5). In some embodiments, the cells are exposed to the inhibitor of TGF-β/activin-Nodal (e.g., SB431542 or "SB") from Day 0 through Day 4, inclusive of each day. In some embodiments, the cells are exposed to the at least one activator of SHH signaling (e.g., SHH protein and purmorphamine, collectively "SHH/PUR") from Day 1 up to about Day 7 (e.g., Day 6 or Day 7). In some embodiments, the cells are exposed to the at least one activator of SHH signaling (e.g., SHH protein and purmorphamine, collectively "SHH/PUR") from Day 1 through Day 6, inclusive of each day. In some embodiments, the cells are exposed to the inhibitor of BMP signaling (e.g., LDN193189 or "LDN") from Day 0 up to about Day 11 (e.g., Day 10 or Day 11). In some embodiments, the cells are exposed to the inhibitor of BMP signaling (e.g., LDN193189 or "LDN") from Day 0 through Day 10, inclusive of each day. In some embodiments, the cells are exposed to the inhibitor of GSK3β signaling (e.g., CHIR99021 or "CHIR") from Day 1 up to about Day 13 (e.g., Day 12 or Day 13). In some embodiments, the cells are exposed to the inhibitor of GSK3β signaling (e.g., CHIR99021 or "CHIR") from Day 1 through Day 12.

In some embodiments, the cells are exposed to (i) an inhibitor of TGF-β/activin-Nodal signaling from Day 0 up to about Day 5 (e.g., Day 4 or Day 5); (ii) at least one activator of Sonic Hedgehog (SHH) signaling from Day 1 up to about Day 7 (e.g., Day 6 or Day 7); (iii) an inhibitor of bone morphogenetic protein (BMP) signaling from Day 0 up to about Day 11 (e.g., Day 10 or Day 11); and (iv) an inhibitor of glycogen synthase kinase 3β (GSK3β) signaling from Day 0 up to about Day 13 (e.g., Day 12 or Day 13). In some embodiments, the cells are exposed to (i) SB from Day 0 up to about Day 5 (e.g., Day 4 or Day 5); (ii) SHH/PUR from Day 1 up to about Day 7 (e.g., Day 6 or Day 8); (iii) LDN from Day 0 up to about Day 11 (e.g., Day 10 or Day 11); and (iv) CHIR from Day 1 up to about Day 13 (e.g., Day 12 or Day 13). In some embodiments, the cells are exposed to (i) an inhibitor of TGF-β/activin-Nodal signaling from Day 0 through Day 5, each day inclusive; (ii) at least one activator of Sonic Hedgehog (SHH) signaling from Day 1 through Day 6, each day inclusive; (iii) an inhibitor of bone morphogenetic protein (BMP) signaling from Day 0 through Day 10, each day inclusive; and (iv) an inhibitor of glycogen synthase kinase 3β (GSK3β) signaling from Day 1 through Day 12, each day inclusive. In some embodiments, the cells are exposed to (i) SB from Day 0 through Day 5, each day inclusive; (ii) SHH/PUR from Day 1 through Day 6, each day inclusive; (iii) LDN from Day 0 through Day 10, each day inclusive; and (iv) CHIR from Day 1 through Day 12, each day inclusive.

In some embodiments, the cells are exposed to brain-derived neurotrophic factor (BDNF) beginning on Day 11. In some embodiments, the cells are exposed to ascorbic acid. In some embodiments, the cells are exposed to glial cell-derived neurotrophic factor (GDNF) beginning on Day 11. In some embodiments, the cells are exposed to dibutyryl cyclic AMP (dbcAMP) beginning on Day 11. In some embodiments, the cells are exposed to transforming growth factor beta-3 (TGFβ3) beginning on Day 11. In some embodiments, the cells are exposed to the inhibitor of Notch signaling (e.g., DAPT) beginning on Day 11. In some embodiments, beginning on Day 11, the cells are exposed to (i) brain-derived neurotrophic factor (BDNF); (ii) ascorbic acid; (iii) glial cell-derived neurotrophic factor (GDNF); (iv) dibutyryl cyclic AMP (dbcAMP); (v) transforming growth factor beta-3 (TGFβ3); and (vi) the inhibitor of Notch signaling (e.g., DAPT) (collectively "BAGCT/DAPT"). In some embodiments, the cells are exposed to BAGCT/DAPT beginning on Day 11 until harvest or collection. In some embodiments, the cells are exposed to BAGCT/DAPT from Day 11 through about Day 14, 15, 16, or 17. In some embodiments, the cells are exposed to BAGCT/DAPT from Day 11 through Day 14. In some embodiments, the cells are exposed to BAGCT/DAPT from Day 11 through Day 15. In some embodiments, the cells are exposed to BAGCT/DAPT from Day 11 through Day 16. In some embodiments, the cells are exposed to BAGCT/DAPT from Day 11 through Day 17.

In some embodiments, the cells are exposed to a Rho-associated protein kinase (ROCK) inhibitor on Day 0. In some embodiments, the cells are exposed to a Rho-associated protein kinase (ROCK) inhibitor on Day 7. In some embodiments, the cells are exposed to a ROCK inhibitor on the day on which the cells are passaged. In some embodiments, the pluripotent stem cells were not exposed to a ROCKi prior to exposing the pluripotent stem cells to the inhibitor of TGF-β/activin-Nodal signaling and the inhibitor of bone morphogenetic protein (BMP) signaling in the first incubation. In some embodiments, the cells are passaged on Day 0 and Day 7.

In some embodiments, the cells are cultured in a basal induction medium comprising DMEM/F-12 and Neurobasal media (e.g., at a 1:1 ratio), supplemented with N2, B27, non-essential amino acids (NEAA), Glutamax, L-glutamine, β-mercaptoethanol, and insulin. In some embodiments, the cells are cultured in the basal induction media from about Day 0 through about Day 10. In some embodiments, the basal induction media is for differentiating pluripotent stem cells into floor plate midbrain progenitor cells.

In some embodiments, the cells are cultured in a maturation medium comprising Neurobasal media, supplemented with N2, B27, non-essential amino acids (NEAA), and Glutamax. In some embodiments, the cells are cultured in the basal induction media from about Day 11 until harvest or collection. In some embodiments, the cells are cultured in the basal induction media from about Day 11 through about Day 14, 15, 16, or 17. In some embodiments, the maturation media is for differentiating floor plate midbrain progenitor cells into determined dopaminergic neuronal progenitor cells, committed dopaminergic neuronal progenitor cells, and/or dopaminergic neuronal cells. In some embodiments, the cells are cultured in the basal induction media from about Day 11 through Day 14. In some embodiments, the cells are cultured in the basal induction media from about Day 11 through Day 15. In some embodiments, the cells are cultured in the basal induction media from about Day 11 through Day 16. In some embodiments, the cells are cultured in the basal induction media from about Day 11 through Day 17. In some embodiments, the maturation media is for differentiating floor plate midbrain progenitor cells into dopaminergic neuronal cells.

In some embodiments, the media is supplemented with small molecules as described above, including SB, SHH/PUR, LDN, CHIR, BAGCT/DAPT, and ROCKi. In some embodiments, the media is changed every day or every other day. In some embodiments the media is changed every day. In some embodiments the media is changed every other day. In some embodiments, the media is changed every day from about Day 1 up to about Day 14, 15, 16, or 17. In some embodiments, the media is changed every day from about Day 1 until harvest or collection, e.g., on Day 14, 15, 16, or 17. In some embodiments, the media is changed by a 50% media exchange every day from about Day 1 through Day 6, and then the media is changed by complete or nearly complete replacement (e.g., at least 95%, 96%, 97%, 98%, or 99% of the media is replaced) every day until harvest or collection, e.g., on Day 14, 15, 16, or 17.

In some embodiments, a serum replacement is provided in the media from about Day 0 up to about Day 10 (e.g., Day 9 or Day 11). In some embodiments, the serum replacement is provided at 5% (v/v) in the media on Day 0 and Day 1. In some embodiments, the serum replacement is provided at 2% (v/v) in the media on Day 2 through Day 10. In some embodiments, the serum replacement is provided at 5% (v/v) in the media on Day 0 and Day 1 and at 2% (v/v) in the media on Day 2 through Day 10. In some embodiments, serum replacement is not provided in the media after Day 10.

In some embodiments, at least about 50% or at least about 75% of the media is changed on one or more of the days. In some embodiments, at least about 50% of the media is changed on one or more of the days, e.g., on Day 1 through Day 6. In some embodiments, at least about 75% of the media is changed on one or more of the days, e.g., on Day 7 through harvest or collection, e.g., Day 14, 15, 16, or 17. In some embodiments, at least 95% of the media is changed on one or more of the days, e.g., on Day 7 through harvest or collection, e.g., Day 14, 15, 16, or 17. In some embodiments about 100% of the media is changed on one or more of the days, e.g., on Day 7 through harvest or collection, e.g., Day 14, 15, 16, or 17.

In some embodiments, about 50% or about 75% of the media is changed. In some embodiments, about 50% of the media is changed. In some embodiments, about 75% of the media is changed. In some embodiments about 100% of the media is changed.

In some embodiments, the media is supplemented with small molecules selected from SB, SHH/PUR, LDN, CHIR, BAGCT/DAPT, ROCKi, or a combination thereof. In some embodiments, when about 50% of the media is changed, the concentration of each small molecule is doubled as compared to its intended concentration in the combined media contacting the cells.

In some embodiments, cells are harvested between about Day 14 and about Day 17. In some embodiments, cells are harvested between about Day 14 and about Day 16. In some embodiments, cells are harvested between about Day 15 and about Day 17. In some embodiments, cells are harvested on about Day 14. In some embodiments, cells are harvested on about Day 15. In some embodiments, cells are harvested on about Day 16. In some embodiments, cells are harvested on about Day 17. In some embodiments, the harvested cells are formulated with a cryopreservant, e.g., DMSO. In some embodiments, the harvested cells produced by the method are cryopreserved before use. In some embodiments, such cryopreserved cells are thawed before use or administration to a subject, e.g., a human patient with a neurodegenerative disease or condition, such as Parkinson's disease.

In some embodiments, compositions comprising cells generated by the methods provided herein are used for the treatment of a neurodegenerative disease or condition, such as Parkinson's disease. In some embodiments, a composition of cells generated by any of the methods described herein are administered to a subject who has Parkinson's disease. In some embodiments, a composition of cells generated by any of the methods described herein are administered by stereotactic injection, such as with a catheter. In some embodiments, a composition of cells generated by any of the methods described herein are administered to the striatum of a subject with Parkinson's disease.

C. Compositions and Formulations

Provided herein are therapeutic compositions containing differentiated cells that are dopaminergic neuronal progenitor cells, including determined dopaminergic neuronal progenitor cells. Also provided herein are therapeutic compositions containing differentiated cells produced by any of the provided methods. In some embodiments, the differentiated cells produced by any of the methods described herein are determined dopaminergic neuronal progenitor cells, committed dopaminergic neuronal progenitor cells, or dopaminergic neuronal cells. In some embodiments, the therapeutic composition comprises dopaminergic neuronal progenitor cells produced by a method that includes: a) performing a first incubation that includes non-adherently culturing pluripotent stem cells in a first culture vessel under conditions to produce a cellular spheroid, wherein the first incubation includes: (i) starting on the first day (Day 0) of the first incubation, exposing the pluripotent stem cells to an inhibitor of TGF-0/activin-Nodal signaling and an inhibitor of bone morphogenetic protein (BMP) signaling in the absence of: x) an activator of Sonic Hedgehog (SHH) signaling, and y) an inhibitor of glycogen synthase kinase 3β (GSK3β) signaling; and (ii) starting on the second day (Day 1) of the first incubation, exposing the pluripotent stem cells to at least one activator of Sonic Hedgehog (SHH) signaling and an inhibitor of glycogen synthase kinase 3β (GSK3β) signaling; and (b) performing a second incubation that includes adherently culturing cells of the spheroid in a second culture vessel under conditions to further differentiate the cells into dopaminergic neuronal progenitor cells.

In some embodiments, the differentiated cells in the provided therapeutic compositions, including those produced by any of the methods described herein, are capable of producing dopamine (DA). In some embodiments, the differentiated cells in the provided therapeutic compositions, including those produced by any of the methods described herein, do not produce or do not substantially produce norepinephrine (NE). Thus, in some embodiments, the differentiated cells in the therapeutic compositions provided herein, including those produced by any of the methods described herein, are capable of producing DA but do not produce or do not substantially produce NE. In some embodiments, the differentiated cells in the provided therapeutic compositions, including those produced by any of the methods described herein, do not produce or do not substantially produce serotonin. Thus, in some embodiments, the differentiated cells in the therapeutic compositions provided herein, including those produced by any of the methods described herein, are capable of producing DA but do not produce or do not substantially produce serotonin.

In some embodiments, the therapeutic compositions include dopaminergic neuronal progenitor cells that have one or more improved properties with respect to use as a treatment for a neurodegenerative disease such as Parkinson's disease, compared to neuronal cells produced using other differentiation methods, such as adherent culture differentiation methods. These improved properties can include, for example, one or more of the following: (a) expressing a higher level of FOXA2; (b) expressing a lower level of PAX6; (c) having a higher predicted graft size after implantation; (d) producing less serotonin; (e) including a higher percentage of viable cells; (f) expressing a higher level of CORIN; (g) expressing a lower level of PITX2; and (h) expressing a lower level of NKX2.1. In some embodiments, the dopaminergic neuronal progenitor cells in the therapeutic composition have two or more of these properties. In some embodiments, the cells have three or more of the properties, and in some embodiments, the cells have four, five, six, or seven or more of the properties. In some embodiments, the cells have all eight of the listed properties.

In some embodiments, the therapeutic compositions provided herein include dopaminergic neuronal progenitor cells that, compared to neuronal cells produced using an adherent culture differentiation method, exhibit one or more properties selected from the group consisting of: (a) expressing a higher level of FOXA2; (b) expressing a lower level of PAX6; (c) having a higher predicted graft size after implantation; (d) having a higher predicted dopamine production level after implantation; (e) producing less serotonin; (f) comprising a higher percentage of viable cells; (g) expressing a higher level of CORIN; (h) expressing a lower level of PITX2; and (i) expressing a lower level of NKX2.1. In some embodiments, the cells of the therapeutic compositions exhibit two or more of these properties. In some embodiments, the cells exhibit three, four, five, six, seven, or eight or more of these properties. In some embodiments, the cells exhibit all nine of the listed properties.

In some embodiments, the therapeutic compositions include dopaminergic neuronal progenitor cells that have a GraftTest score of at least 1,500, calculated as described in U.S. Provisional Application No. 63/598,533, entitled "METHODS OF PREDICTING CHARACTERISTICS OF DIFFERENTIATED NEURONAL CELLS," filed Nov. 13, 2023. In some embodiments, the dopaminergic neuronal progenitor cells in the therapeutic compositions produce serotonin at a level that increases less than two-fold when stimulated with KCl compared to unstimulated baseline. In some embodiments, more than 99% of the dopaminergic neuronal progenitor cells in the therapeutic compositions are viable. In some embodiments, the therapeutic composition includes dopaminergic neuronal progenitor cells that express FOXA2 at greater than 100 TPM, based on bulk RNAseq analysis. In some embodiments, the dopaminergic neuronal progenitor cells in the therapeutic compositions express CORIN at greater than 300 TPM. In some embodiments, the dopaminergic neuronal progenitor cells in the therapeutic compositions express PITX2 at less than 50 TPM. In some embodiments, the dopaminergic neuronal progenitor cells in the therapeutic compositions express NKX2.1 at less than 10 TPM. In some embodiments, the dopaminergic neuronal progenitor cells in the therapeutic composition have two or more of these properties. In some embodiments, the cells have three or more of the properties, and in some embodiments, the cells have four, five, or six or more of the properties. In some embodiments, the cells have all seven of the properties listed in this paragraph.

In some embodiments, the differentiated cells produced by any of the methods described herein are dopaminergic neuronal progenitor cells, including determined dopaminergic neuronal progenitor cells or committed dopaminergic neuronal progenitor cells (e.g., midbrain fate DA neurons). In some embodiments, the midbrain fate determined dopaminergic neuronal progenitor cells or committed dopaminergic neuronal progenitor cells are FOXA2+/TH+ at the time of harvest. In some embodiments, the midbrain fate determined dopaminergic neuronal progenitor cells or committed dopaminergic neuronal progenitor cells are FOXA2+/TH+ by or on about Day 14. In some embodiments, the midbrain fate determined dopaminergic neuronal progenitor cells or committed dopaminergic neuronal progenitor cells are FOXA2+/TH+ by or on about Day 15. In some embodiments, the midbrain fate determined dopaminergic neuronal progenitor cells or committed dopaminergic neuronal progenitor cells are FOXA2+/TH+ by or on about Day 16. In some embodiments, the midbrain fate determined dopaminergic neuronal progenitor cells or committed dopaminergic neuronal progenitor cells are FOXA2+/TH+ by or on about Day 17.

Methods for measuring or assessing gene expression or gene products (including the transcriptional and/or translation products) include those described in Section A. Further, in some embodiments, measuring or assessing gene expression or gene products is or includes assessing, measuring, determining, and/or quantifying a level, amount, or concentration of a gene product (transcription and/or translational) in the sample.

In some embodiments, gene expression is or includes a process by which information of the gene is used in the synthesis of a gene product. Thus, in some embodiments, a gene product is any biomolecule that is assembled, generated, and/or synthesized with information encoded by a gene, and may include polynucleotides and/or polypeptides. In particular embodiments, assessing, measuring, and/or determining gene expression is or includes determining or measuring the level, amount, or concentration of the gene product. In certain embodiments, the level, amount, or concentration of the gene product may be transformed (e.g., normalized) or directly analyzed (e.g., raw).

In some embodiments, the gene product is or includes a protein, i.e., a polypeptide, that is encoded by and/or expressed by the gene. In particular embodiments, the gene product encodes a protein that is localized and/or exposed on the surface of a cell. In some embodiments, the protein is a soluble protein. In certain embodiments, the protein is secreted by a cell. In particular embodiments, the gene expression is the amount, level, and/or concentration of a protein that is encoded by the gene. In certain embodiments, one or more protein gene products are measured by any suitable means known in the art. Suitable methods for assessing, measuring, determining, and/or quantifying the level, amount, or concentration or more or more protein gene products include, but are not limited to detection with immunoassays, nucleic acid-based or protein-based aptamer techniques, HPLC (high precision liquid chromatography), peptide sequencing (such as Edman degradation sequencing or mass spectrometry (such as MS/MS), optionally coupled to HPLC), and microarray adaptations of any of the foregoing (including nucleic acid, antibody or protein-protein (i.e., non-antibody) arrays). In some embodiments, the immunoassay is or includes methods or assays that detect proteins based on an immunological reaction, e.g., by detecting the binding of an antibody or antigen binding antibody fragment to a gene product. Immunoassays include, but are not limited to, quantitative immunocytochemistry or immunohistochemistry, ELISA (including direct, indirect, sandwich, competitive, multiple and portable ELISAs (see, e.g., U.S. Pat. No. 7,510,687), western blotting (including one, two or higher dimensional blotting or other chromatographic means, optionally including peptide sequencing), enzyme immunoassay (EIA), RIA (radioimmunoassay), and SPR (surface plasmon resonance).

In certain embodiments, the gene product is a polynucleotide, e.g., an mRNA or a protein, that is encoded by the gene. In some embodiments, the gene product is a polynucleotide that is expressed by and/or encoded by the gene. In certain embodiments, the polynucleotide is an RNA. In some embodiments, the gene product is a messenger RNA (mRNA), a transfer RNA (tRNA), a ribosomal RNA, a small nuclear RNA, a small nucleolar RNA, an antisense RNA, long non-coding RNA, a microRNA, a Piwi-interacting RNA, a small interfering RNA, and/or a short hairpin RNA. In particular embodiments, the gene product is an mRNA.

CALIMIn certain embodiments, the RNA gene product is assessed, measured, determined, and/or quantified by directly assessing, measuring, determining, and/or quantifying a cDNA polynucleotide and/or a cDNA oligonucleotide that is derived from the RNA gene product.

In particular embodiments, the amount or level of a polynucleotide in a sample may be assessed, measured, determined, and/or quantified by any suitable means known in the art. For example, in some embodiments, the amount or level of a polynucleotide gene product can be assessed, measured, determined, and/or quantified by polymerase chain reaction (PCR), including reverse transcriptase (rt) PCR, droplet digital PCR, real-time and quantitative PCR (qPCR) methods (including, e.g., TAQMAN®, molecular beacon, LIGHTUP™, SCORPION™, SIMPLEPROBES®; see, e.g., U.S. Pat. Nos. 5,538,848; 5,925,517; 6,174,670; 6,329,144; 6,326,145 and 6,635,427); northern blotting; Southern blotting, e.g., of reverse transcription products and derivatives; array based methods, including blotted arrays, microarrays, or in situ-synthesized arrays; and sequencing, e.g., sequencing by synthesis, pyrosequencing, dideoxy sequencing, or sequencing by ligation, or any other methods known in the art, such as discussed in Shendure et al., *Nat. Rev. Genet.* 5:335-44 (2004) or Nowrousian, *Euk. Cell* 9 (9): 1300-1310 (2010), including such specific platforms as HELICOS®, ROCHE 454, ILLUMINA®/SOLEXA®, ABI SOLID®, and POLONATOR® sequencing. In particular embodiments, the levels of nucleic acid gene products are measured by quantitative PCR (qPCR) methods, such qRT-PCR. In some embodiments, the qRT-PCR uses three nucleic acid sets for each gene, where the three nucleic acids comprise a primer pair together with a probe that binds between the regions of a target nucleic acid where the primers bind-known commercially as a TAQMAN® assay.

In particular embodiments, the expression of two or more of the genes are measured or assessed simultaneously. In certain embodiments, a multiplex PCR, e.g., a multiplex rt-PCR assessing or a multiplex quantitative PCR (qPCR) for, measuring, determining, and/or quantifying the level, amount, or concentration of two or more gene products. In some embodiments, microarrays (e.g., AFFYMETRIX®, AGILENT® and ILLUMINA®-style arrays) are used for assessing, measuring, determining, and/or quantifying the level, amount, or concentration of two or more gene products. In some embodiments, microarrays are used for assessing, measuring, determining, and/or quantifying the level, amount, or concentration of a cDNA polynucleotide that is derived from an RNA gene product. In some embodiments, the expression of one or more gene products, e.g., polynucleotide gene products, is determined by sequencing the gene product and/or by sequencing a cDNA polynucleotide that is derived from the from the gene product. In some embodiments, the sequencing is performed by a non-Sanger sequencing method and/or a next generation sequencing (NGS) technique. Examples of Next Generation Sequencing techniques include, but are not limited to Massively Parallel Signature Sequencing (MPSS), Polony sequencing, pyrosequencing, Reversible dye-terminator sequencing, SOLID sequencing, Ion semiconductor sequencing, DNA nanoball sequencing, Helioscope single molecule sequencing, Single molecule real time (SMRT) sequencing, Single molecule real time (RNAP) sequencing, and Nanopore DNA sequencing.

In some embodiments, the NGS technique is RNA sequencing (RNA-Seq). In particular embodiments, the expression of the one or more polynucleotide gene products is measured, determined, and/or quantified by RNA-Seq. RNA-Seq, also called whole transcriptome shotgun sequencing determines the presence and quantity of RNA in a sample. RNA sequencing methods have been adapted for the most common DNA sequencing platforms (HiSeq systems (Illumina), 454 Genome Sequencer FLX System (Roche), Applied Biosystems SOLID (Life Technologies), IonTorrent (Life Technologies). These platforms require initial reverse transcription of RNA into cDNA. Conversely, the single molecule sequencer HeliScope (Helicos BioSciences) is able to use RNA as a template for sequencing. A proof of principle for direct RNA sequencing on the PacBio RS platform has also been demonstrated (Pacific Bioscience). In some embodiments, the one or more RNA gene products are assessed, measured, determined, and/or quantified by RNA-seq. In some embodiments, the RNA-seq is a tag-based RNA-seq. In tag-based methods, each transcript is represented by a unique tag. Initially, tag-based approaches were developed as a sequence-based method to measure transcript abundance and identify differentially expressed genes, assuming that the number of tags (counts) directly corresponds to the abundance of the mRNA molecules. The reduced complexity of the sample, obtained by sequencing a defined region, was essential to make the Sanger-based methods affordable. When NGS technology became available, the high number of reads that could be generated facilitated differential gene expression analysis. A transcript length bias in the quantification of gene expression levels, such as observed for shotgun methods, is not encountered in tag-based methods. All tag-based methods are by definition strand specific. In particular embodiments, the one or more RNA gene products are assessed, measured, determined, and/or quantified by tag-based RNA-seq.

In some embodiments, the RNA-seq is a shotgun RNA-seq. Numerous protocols have been described for shotgun RNA-seq, but they have many steps in common: fragmentation (which can occur at RNA level or cDNA level, conversion of the RNA into cDNA (performed by oligo dT or random primers), second-strand synthesis, ligation of adapter sequences at the 3' and 5' ends (at RNA or DNA level) and final amplification. In some embodiments, RNA-seq can focus only on polyadenylated RNA molecules (mainly mRNAs but also some lncRNAs, snoRNAs, pseudogenes and histones) if poly(A)+RNAs are selected prior to fragmentation, or may also include non-polyadenylated RNAs if no selection is performed. In the latter case, ribosomal RNA (more than 80% of the total RNA pool) needs to be depleted prior to fragmentation. It is, therefore, clear that differences in capturing of the mRNA part of the transcriptome lead to a partial overlap in the type of detected transcripts. Moreover, different protocols may affect the abundance and the distribution of the sequenced reads. This makes it difficult to compare results from experiments with different library preparation protocols.

In some embodiments, RNA from each sample is obtained, fragmented and used to generate complementary DNA (cDNA) samples, such as cDNA libraries for sequencing. Reads may be processed and aligned to the human genome and the expected number of mappings per gene/isoform are estimated and used to determine read counts. In some embodiments, read counts are normalized by the length of the genes/isoforms and number of reads in a library to yield FPKM normalized, e.g., by length of the genes/isoforms and number of reads in the library, to yield fragments per kilobase of exon per million mapped reads (FPKM) according to the gene length and total mapped reads. In some aspects, between-sample normalization is achieved by normalization, such as 75th quantile normalization, where each sample is scaled by the median of 75th quantiles from all samples, e.g., to yield quantile-normalized FPKM (FPKQ) values. The FPKQ values may be log-transformed (log 2).

In some embodiments, RNA from each sample is obtained, fragmented and used to generate complementary DNA (cDNA) samples, such as cDNA libraries for sequencing. Reads may be processed and aligned to the human genome and the expected number of mappings per gene/isoform are estimated and used to determine read counts. In some embodiments, read counts are normalized by the length of the genes/isoforms and number of reads in a library. In some embodiments, read counts are provided as counts per million (CPM).

In some embodiments, relative gene expression is measured by comparing the CPM of a target gene to the CPM of a housekeeping gene. In some embodiments, the housekeeping gene is GAPDH. In some embodiments, the relative gene expression of a target gene is determined as the ratio of the CPM of the target gene to CPM of a housekeeping gene (e.g., GAPDH).

In some embodiments, among any of the provided compositions are pharmaceutical compositions containing a pharmaceutically acceptable carrier. In some embodiments, the dose of cells comprising cells produced by any of the methods disclosed herein, is provided as a composition or formulation, such as a pharmaceutical composition or formulation. Such compositions can be used in accord with the provided methods, articles of manufacture, and/or with the provided compositions, such as in the prevention or treatment of diseases, conditions, and disorders, such as neurodegenerative disorders.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell or agent and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredient useful for the particular indication, disease, or condition being prevented or treated with the cells or agents, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as carbidopa-levodopa (e.g., Levodopa), dopamine agonists (e.g., pramipexole, ropinirole, rotigotine, and apomorphine), MAO B inhibitors (e.g., selegiline, rasagiline, and safinamide), catechol O-methyltransferase (COMT) inhibitors (e.g., entacapone and tolcapone), anticholinergics (e.g., benztropine and trihexylphenidyl), amantadine, etc. In some embodiments, the agents or cells are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The formulation or composition may also be administered in combination with another form of treatment useful for the particular indication, disease, or condition being prevented or treated with the cells or agents, where the respective activities do not adversely affect one another. Thus, in some embodiments, the pharmaceutical composition is administered in combination with deep brain stimulation (DBS).

The pharmaceutical composition in some embodiments contains agents or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The agents or cells can be administered by any suitable means, for example, by stereotactic injection (e.g., using a catheter). In some embodiments, a given dose is administered by a single bolus administration of the cells or agent. In some embodiments, it is administered by multiple bolus administrations of the cells or agent, for example, over a period of months or years. In some embodiments, the agents or cells can be administered by stereotactic injection into the brain, such as in the striatum.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

The cells or agents may be administered using standard administration techniques, formulations, and/or devices. Provided are formulations and devices, such as syringes and vials, for storage and administration of the compositions. With respect to cells, administration can be autologous. For example, non-pluripotent cells (e.g., fibroblasts) can be obtained from a subject, and administered to the same subject following reprogramming and differentiation. When administering a therapeutic composition (e.g., a pharmaceutical composition containing a genetically reprogrammed and/or differentiated cell or an agent that treats or ameliorates symptoms of a disease or disorder, such as a neurodegenerative disorder), it will generally be formulated in a unit dosage injectable form (solution, suspension, emulsion). Formulations include those for stereotactic administration, such as into the brain (e.g., the striatum).

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the agent or cells in a solvent, such as in admixture with a suitable carrier, diluent, or excipient such as sterile water, physiological saline, glucose, dextrose, or the like.

The formulations to be used for in vivo administration are generally sterile. Sterility may be readily accomplished, e.g., by filtration through sterile filtration membranes.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

In some embodiments, the formulation buffer contains a cryopreservative. In some embodiments, the cells are formulated with a cryopreservative solution that contains 1.0% to 30% DMSO solution, such as a 5% to 20% DMSO solution or a 5% to 10% DMSO solution. In some embodiments, the cryopreservation solution is or contains, for example, PBS containing 20% DMSO and 8% human serum albumin (HSA), or other suitable cell freezing media. In some embodiments, the cryopreservative solution is or contains, for example, at least or about 7.5% DMSO. In some embodiments, the processing steps can involve washing the differentiated cells to replace the cells in a cryopreservative solution. In some embodiments, the cells are frozen, e.g., cryopreserved or cryoprotected, in media and/or solution with a final concentration of or of about 12.5%, 12.0%, 11.5%, 11.0%, 10.5%, 10.0%, 9.5%, 9. 0%, 8.5%, 8.0%, 7.5%, 7.0%, 6.5%, 6.0%, 5.5%, or 5.0% DMSO, or between 1% and 15%, between 6% and 12%, between 5% and 10%, or between 6% and 8% DMSO. In particular embodiments, the cells are frozen, e.g., cryopreserved or cryoprotected, in media and/or solution with a final concentration of or of about 5.0%, 4.5%, 4.0%, 3.5%, 3.0%, 2.5%, 2.0%, 1.5%, 1.25%, 1.0%, 0.75%, 0.5%, or 0.25% HSA, or between 0.1% and −5%, between 0.25% and 4%, between 0.5% and 2%, or between 1% and 2% HSA.

In particular embodiments, the composition of differentiated cells are formulated, cryopreserved, and then stored for an amount of time. In certain embodiments, the formulated, cryopreserved cells are stored until the cells are released for administration. In particular embodiments, the formulated cryopreserved cells are stored for between 1 day and 6 months, between 1 month and 3 months, between 1 day and 14 days, between 1 day and 7 days, between 3 days and 6 days, between 6 months and 12 months, or longer than 12 months. In some embodiments, the cells are cryopreserved and stored for, for about, or for less than 1 days, 2 days, 3 days, 4 days, 5 days, 6 days, or 7 days. In certain embodiments, the cells are thawed and administered to a subject after the storage.

In some embodiments, the formulation is carried out using one or more processing step including washing, diluting or concentrating the cells. In some embodiments, the processing can include dilution or concentration of the cells to a desired concentration or number, such as unit dose form compositions including the number of cells for administration in a given dose or fraction thereof. In some embodiments, the processing steps can include a volume-reduction to thereby increase the concentration of cells as desired. In some embodiments, the processing steps can include a volume-addition to thereby decrease the concentration of cells as desired. In some embodiments, the processing includes adding a volume of a formulation buffer to differentiated cells. In some embodiments, the volume of formulation buffer is from or from about 1 μL to 5000 μL, such as at least or about at least or about or 5 μL, 10 μL, 20 μL, 50 μL, 100 μL, 200 μL, 300 μL, 400 μL, 500 μL, 1000 μL, 2000 μL, 3000 μL, 4000 μL, or 5000 μL.

A container may generally contain the cells to be administered, e.g., one or more unit doses thereof. The unit dose may be an amount or number of the cells to be administered to the subject or twice the number (or more) of the cells to be administered. It may be the lowest dose or lowest possible dose of the cells that would be administered to the subject.

In some embodiments, such cells produced by the method, or a composition comprising such cells, are administered to a subject for treating a neurodegenerative disease or condition.

D. Methods of Treatment

Provided herein are methods of using any of the provided compositions for treating a disease or condition in a subject in need thereof. In particular embodiments, the composition is produced by the methods provided herein. Such methods and uses include therapeutic methods and uses, for example, involving administration of the therapeutic cells, or compositions containing the same, to a subject having a disease, condition, or disorder. In some embodiments the disease or condition is a neurodegenerative disease or condition. In some embodiments, the cells or pharmaceutical composition thereof is administered in an effective amount to effect treatment of the disease or disorder. Uses include uses of the cells or pharmaceutical compositions thereof in such methods and treatments, and in the preparation or manufacture of a medicament in order to carry out such therapeutic methods. In some embodiments, the methods thereby treat the disease or condition or disorder in the subject.

The present disclosure relates to methods of lineage specific differentiation of pluripotent stem cells (PSCs), including embryonic stem (ES) cells and induced pluripotent stem cells (iPSCs), for use in neurodegenerative diseases. Specifically, the methods, compositions, and uses thereof provided herein contemplate differentiation of pluripotent stem cells for administration to subjects exhibiting a loss of dopaminergic neuronal cells, including Parkinson's disease.

Parkinson's disease (PD) is the second most common neurodegenerative, estimated to affect 4-5 million patients worldwide. This number is predicted to more than double by 2030. PD is the second most common neurodegenerative disorder after Alzheimer's disease, affecting approximately 1 million patients in the US with 60,000 new patients diagnosed each year. Currently there is no cure for PD, which is characterized pathologically by a selective loss of midbrain DA neurons in the substantia nigra. A fundamental characteristic of PD is therefore progressive, severe and irreversible loss of midbrain dopaminergic neuronal cells resulting in ultimately disabling motor dysfunction.

In some embodiments, a subject has a neurodegenerative disease. In some embodiments, the neurodegenerative disease comprises the loss of dopamine neurons in the brain. In some embodiments, the subject has lost dopamine neurons in the substantia nigra (SN). In some embodiments, the subject has lost dopamine neurons in the substantia nigra *pas compacta* (SNc). In some embodiments, the subject exhibits rigidity, bradykinesia, postural reflect impairment, resting tremor, or a combination thereof. In some embodiments, the subject exhibits abnormal $[_{18}F]$-L-DOPA PET scan. In some embodiments, the subject exhibits $[_{18}F]$-DG-PET evidence for a Parkinson's Disease Related Pattern (PDRP).

In some embodiments, the neurodegenerative disease is Parkinsonism. In some embodiments, the neurodegenerative disease is Parkinson's disease. In some embodiments, the neurodegenerative disease is idiopathic Parkinson's disease. In some embodiments, the neurodegenerative disease is a familial form of Parkinson's disease. In some embodiments, the subject has mild Parkinson's disease. In some embodiments, the subject has a Movement Disorder Society-Unified Parkinson's Disease Rating Scale (MDS-UPDRS) motor score of less than or equal to 32. In some embodiments, the subject has moderate or advanced Parkinson's disease. In some embodiments, the subject has mild Parkinson's disease. In some embodiments, the subject has a MDS-UPDRS motor score of between 33 and 60.

In some embodiments, a dose of cells is administered to subjects in accord with the provided methods, and/or with the provided articles of manufacture or compositions. In some embodiments, the size or timing of the doses is determined as a function of the particular disease or condition in the subject. In some cases, the size or timing of the doses for a particular disease in view of the provided description may be empirically determined.

In some embodiments, the dose of cells is administered to the striatum of the subject. In some embodiments, the dose of cells is administered to one hemisphere of the subject's striatum. In some embodiments, the dose of cells is administered to both hemispheres of the subject's.

In some embodiments, the dose of cells administered to the subject is about $5\times10^6$ cells. In some embodiments, the dose of cells administered to the subject is about $10\times10^6$ cells. In some embodiments, the dose of cells administered to the subject is about $15\times10^6$ cells. In some embodiments, the dose of cells administered to the subject is about $20\times10^6$ cells. In some embodiments, the dose of cells administered to the subject is about $25\times10^6$ cells. In some embodiments, the dose of cells administered to the subject is about $30\times10^6$ cells.

In some embodiments, the dose of cells comprises between at or about 250,000 cells per hemisphere and at or about 20 million cells per hemisphere, between at or about 500,000 cells per hemisphere and at or about 20 million cells per hemisphere, between at or about 1 million cells per hemisphere and at or about 20 million cells per hemisphere, between at or about 5 million cells per hemisphere and at or about 20 million cells per hemisphere, between at or about 10 million cells per hemisphere and at or about 20 million cells per hemisphere, between at or about 15 million cells per hemisphere and at or about 20 million cells per hemisphere, between at or about 250,000 cells per hemisphere and at or about 15 million cells per hemisphere, between at or about 500,000 cells per hemisphere and at or about 15 million cells per hemisphere, between at or about 1 million cells per hemisphere and at or about 15 million cells per hemisphere, between at or about 5 million cells per hemisphere and at or about 15 million cells per hemisphere, between at or about 10 million cells per hemisphere and at or about 15 million cells per hemisphere, between at or about 250,000 cells per hemisphere and at or about 10 million cells per hemisphere, between at or about 500,000 cells per hemisphere and at or about 10 million cells per hemisphere, between at or about 1 million cells per hemisphere and at or about 10 million cells per hemisphere, between at or about 5 million cells per hemisphere and at or about 10 million cells per hemisphere, between at or about 250,000 cells per hemisphere and at or about 5 million cells per hemisphere, between at or about 500,000 cells per hemisphere and at or about 5 million cells per hemisphere, between at or about 1 million cells per hemisphere and at or about 5 million cells per hemisphere, between at or about 250,000 cells per hemisphere and at or about 1 million cells per hemisphere, between at or about 500,000 cells per hemisphere and at or about 1 million cells per hemisphere, or between at or about 250,000 cells per hemisphere and at or about 500,000 cells per hemisphere.

In some embodiments, the dose of cells is between at or about 1 million cells per hemisphere and at or about 30 million cells per hemisphere. In some embodiments, the dose of cells is between at or about 5 million cells per hemisphere and at or about 20 million cells per hemisphere. In some embodiments, the dose of cells is between at or about 10 million cells per hemisphere and at or about 15 million cells per hemisphere.

In some embodiments, the dose of cells is between about $3\times10^6$ cells/hemisphere and $15\times10^6$ cells/hemisphere. In some embodiments, the dose of cells is about $3\times10^6$ cells/hemisphere. In some embodiments, the dose of cells is about $4\times10^6$ cells/hemisphere. In some embodiments, the dose of cells is about $5\times10^6$ cells/hemisphere. In some embodiments, the dose of cells is about about $6\times10^6$ cells/hemisphere. In some embodiments, the dose of cells is about about $7\times10^6$ cells/hemisphere. In some embodiments, the dose of cells is about about $8\times10^6$ cells/hemisphere. In some embodiments, the dose of cells is about about $9\times10^6$ cells/hemisphere. In some embodiments, the dose of cells is about $10\times10^6$ cells/hemisphere. In some embodiments, the dose of cells is about $11\times10^6$ cells/hemisphere. In some embodiments, the dose of cells is about $12\times10^6$ cells/hemisphere. In some embodiments, the dose of cells is about $13\times10^6$ cells/hemisphere. In some embodiments, the dose of cells is about $14\times10^6$ cells/hemisphere. In some embodiments, the dose of cells is about $15\times10^6$ cells/hemisphere.

In some embodiments, the number of cells administered to the subject is between about $0.25\times10^6$ total cells and about $20\times10^6$ total cells, between about $0.25\times10^6$ total cells and about $15\times10^6$ total cells, between about $0.25\times10^6$ total cells and about $10\times10^6$ total cells, between about $0.25\times10^6$ total cells and about $5\times10^6$ total cells, between about $0.25\times10^6$ total cells and about $1\times10^6$ total cells, between about $0.25\times10^6$ total cells and about $0.75\times10^6$ total cells, between about $0.25\times10^6$ total cells and about $0.5\times10^6$ total cells, between about $0.5\times10^6$ total cells and about $20\times10^6$ total cells, between about $0.5\times10^6$ total cells and about $15\times10^6$ total cells, between about $0.5\times10^6$ total cells and about $10\times10^6$ total cells, between about $0.5\times10^6$ total cells and about $5\times10^6$ total cells, between about $0.5\times10^6$ total cells and about $1\times10^6$ total cells, between about $0.5\times10^6$ total cells and about $0.75\times10^6$ total cells, between about $0.75\times10^6$ total cells and about $20\times10^6$ total cells, between about $0.75\times10^6$ total cells and about $15\times10^6$ total cells, between about $0.75\times10^6$ total cells and about $10\times10^6$ total cells, between about $0.75\times10^6$ total cells and about $5\times10^6$ total cells, between about $0.75\times10^6$ total cells and about $1\times10^6$ total cells, between about $1\times10^6$ total cells and about $20\times10^6$ total cells, between about $1\times10^6$ total cells and about $15\times10^6$ total cells, between about $1\times10^6$ total cells and about $10\times10^6$ total cells, between about $1\times10^6$ total cells and about $5\times10^6$ total cells, between about $5\times10^6$ total cells and about $20\times10^6$ total cells, between about $5\times10^6$ total cells and about $15\times10^6$ total cells, between about $5\times10^6$ total cells and about $10\times10^6$ total cells, between about $10\times10^6$ total cells and about $20\times10^6$ total cells, between about $10\times10^6$ total cells and about $15\times10^6$ total cells, or between about $15\times10^6$ total cells and about $20\times10^6$ total cells.

In certain embodiments, the cells, or individual populations of sub-types of cells, are administered to the subject at a range of about 5 million cells per hemisphere to about 20 million cells per hemisphere or any value in between these ranges. Dosages may vary depending on attributes particular to the disease or disorder and/or patient and/or other treatments.

In some embodiments, the patient is administered multiple doses, and each of the doses or the total dose can be within any of the foregoing values. In some embodiments, the dose of cells comprises the administration of from or from about 5 million cells per hemisphere to about 20 million cells per hemisphere, each inclusive.

In some embodiments, the dose of cells, e.g., determined dopaminergic neuronal progenitor cells or committed dopaminergic neuronal progenitor cells, is administered to the subject as a single dose or is administered only one time within a period of two weeks, one month, three months, six months, 1 year or more.

In the context of stem cell transplant, administration of a given "dose" encompasses administration of the given amount or number of cells as a single composition and/or single uninterrupted administration, e.g., as a single injection or continuous infusion, and also encompasses administration of the given amount or number of cells as a split dose or as a plurality of compositions, provided in multiple individual compositions or infusions, over a specified period of time, such as a day. Thus, in some contexts, the dose is a single or continuous administration of the specified number of cells, given or initiated at a single point in time. In some contexts, however, the dose is administered in multiple injections or infusions in a single period, such as by multiple infusions over a single day period.

Thus, in some aspects, the cells of the dose are administered in a single pharmaceutical composition. In some embodiments, the cells of the dose are administered in a plurality of compositions, collectively containing the cells of the dose.

In some embodiments, cells of the dose may be administered by administration of a plurality of compositions or solutions, such as a first and a second, optionally more, each containing some cells of the dose. In some aspects, the plurality of compositions, each containing a different population and/or sub-types of cells, are administered separately or independently, optionally within a certain period of time.

In some embodiments, the administration of the composition or dose, e.g., administration of the plurality of cell compositions, involves administration of the cell compositions separately. In some aspects, the separate administrations are carried out simultaneously, or sequentially, in any order.

In some embodiments, the subject receives multiple doses, e.g., two or more doses or multiple consecutive doses, of the cells. In some embodiments, two doses are administered to a subject. In some embodiments, multiple consecutive doses are administered following the first dose, such that an additional dose or doses are administered following administration of the consecutive dose. In some aspects, the number of cells administered to the subject in the additional dose is the same as or similar to the first dose and/or consecutive dose. In some embodiments, the additional dose or doses are larger than prior doses.

In some aspects, the size of the first and/or consecutive dose is determined based on one or more criteria such as response of the subject to prior treatment, e.g., disease stage and/or likelihood or incidence of the subject developing adverse outcomes, e.g., dyskinesia.

In some embodiments, the dose of cells is generally large enough to be effective in improving symptoms of the disease.

In some embodiments, the cells are administered at a desired dosage, which in some aspects includes a desired dose or number of cells or cell type(s) and/or a desired ratio of cell types. In some embodiments, the dosage of cells is based on a desired total number (or number per kg of body weight) of cells in the individual populations or of individual cell types (e.g., TH+ or TH−). In some embodiments, the dosage is based on a combination of such features, such as a desired number of total cells, desired ratio, and desired total number of cells in the individual populations.

Thus, in some embodiments, the dosage is based on a desired fixed dose of total cells and a desired ratio, and/or based on a desired fixed dose of one or more, e.g., each, of the individual sub-types or sub-populations.

In particular embodiments, the numbers and/or concentrations of cells refer to the number of TH-negative cells. In other embodiments, the numbers and/or concentrations of cells refer to the number or concentration of all cells administered.

In some embodiments, the cells are administered at a desired dosage, which in some aspects includes a desired dose or number of cells or cell type(s) and/or a desired ratio of cell types. Thus, the dosage of cells in some embodiments is based on a total number of cells and a desired ratio of the individual populations or sub-types. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

Thus, in some embodiments, the dosage is based on a desired fixed dose of total cells and a desired ratio, and/or based on a desired fixed dose of one or more, e.g., each, of the individual sub-types or sub-populations.

In particular embodiments, the numbers and/or concentrations of cells refer to the number of TH-negative cells. In other embodiments, the numbers and/or concentrations of cells refer to the number or concentration of all cells administered.

In some aspects, the size of the dose is determined based on one or more criteria such as response of the subject to prior treatment, e.g., disease type and/or stage, and/or likelihood or incidence of the subject developing toxic outcomes, e.g., dyskinesia.

E. Articles of Manufacture and Kits

Also provided are articles of manufacture, systems, apparatuses, and kits useful in performing the provided methods. Also provided are articles of manufacture, including: (i) one or more reagents for differentiation of pluripotent stem cells into floor plate midbrain progenitor cells, dopaminergic neuronal progenitor cells, determined dopaminergic neuronal progenitor cells, committed dopaminergic neuronal progenitor cells and/or dopaminergic neuronal cells; and (ii) instructions for use of the one or more reagents for performing any methods described herein.

In some of any such embodiments, the reagent for differentiation is or includes a small molecule, capable of inhibiting TGF-β/activin-Nodal signaling. In some of any such embodiments, the reagent for differentiation is or includes SB431542. In some of any such embodiments, the reagent for differentiation is or includes a small molecule, capable of activating SHH signaling. In some of any such embodiments, the reagent for activating SHH signaling is or includes SHH. In some of any such embodiments, the reagent for activating SHH signaling is or includes purmorphamine. In some of any such embodiments, the reagent for activating SHH signaling is or includes SHH and purmorphamine. In some of any such embodiments, the reagent for differentiation is or includes a small molecule, capable of inhibiting BMP signaling. In some of any such embodiments, the reagent for inhibiting BMP signaling is LDN193189. In some of any such embodiments, the reagent for differentiation is or includes a small molecule, capable of inhibiting GSK3β signaling. In some embodiments, the reagent is or includes CHIR99021. In some embodiments, the reagent for differentiation is or includes one or more of BDNF, GDNF, dbcAMP, ascorbic acid, TGFβ3, and DAPT. The reagents in the kit in one embodiment may be in solution, may be frozen, or may be lyophilized.

Also provided are articles of manufacture, including (i) any composition described herein; and (ii) instructions for administering the composition to a subject.

In some embodiments, the articles of manufacture or kits include one or more containers, typically a plurality of containers, packaging material, and a label or package insert on or associated with the container or containers and/or packaging, generally including instructions for use, e.g., instructions for reagents for differentiation of pluripotent cells, e.g., differentiation of iPSCs into floor plate midbrain progenitor cells, determined dopaminergic neuronal progenitor cells, committed dopaminergic neuronal progenitor cells and/or dopaminergic neuronal cells, and instructions to carry out any of the methods provided herein. In some aspects, the provided articles of manufacture contain reagents for differentiation and/or maturation of cells, for example, at one or more steps of the manufacturing process, such as any reagents described in any steps of Sections B and C.

Also provided are articles of manufacture and kits containing differentiated cells, such as those generated using the methods provided herein, and optionally instructions for use, for example, instructions for administering. In some embodiments, the instructions provide directions or specify methods for assessing if a subject, prior to receiving a cell therapy, is likely or suspected of being likely to respond and/or the degree or level of response following administration of differentiated cells expressing a recombinant receptor for treating a disease or disorder. In some aspects, the articles of manufacture can contain a dose or a composition of differentiated cells.

The articles of manufacture provided herein contain packaging materials. Packaging materials for use in packaging the provided materials are well known to those of skill in the art. See, for example, U.S. Pat. Nos. 5,323,907, 5,052,558 and 5,033,252, each of which is incorporated herein in its entirety. Examples of packaging materials include, but are not limited to, blister packs, bottles, tubes, inhalers, pumps, bags, vials, containers, syringes, disposable laboratory supplies, e.g., pipette tips and/or plastic plates, or bottles. The articles of manufacture or kits can include a device so as to facilitate dispensing of the materials or to facilitate use in a high-throughput or large-scale manner, e.g., to facilitate use in robotic equipment. Typically, the packaging is non-reactive with the compositions contained therein.

In some embodiments, the reagents and/or cell compositions are packaged separately. In some embodiments, each container can have a single compartment. In some embodiments, other components of the articles of manufacture or kits are packaged separately, or together in a single compartment.

EXAMPLES

The following examples are included for illustrative purposes only and are not intended to limit the scope of the invention.

A. Example 1: Neuronal Differentiation of iPSCs

Induced pluripotent stem cells (iPSCs) were created from fibroblasts obtained from human donors with Parkinson's disease and subjected to a dopaminergic neuronal differentiation protocol.

iPSCs from the human donors were maintained by plating in Laminin-511 E8-coated 6-well plates. The cells were cultured without feeder cells in mTeSR™1-based media until they reached approximately 75-90% confluence. The iPSCs were then washed with sterile PBS and detached from the 6-well plates by enzymatic dissociation with Accutase™. The collected iPSCs were then used in the subsequent differentiation protocol.

The collected iPSCs were re-suspended in "basal induction media" (see below) and seeded under non-adherent conditions using 24-well AggreWell™ plates. The iPSCs were seeded at $3.6\times10^6$ cells/well at Day 0, with approximately 3,000 cells/microwell in media supplemented as described below for each of the enumerated days of the differentiation method, e.g., Day 0 through Day 16. The cells were cultured for 7 days under non-adherent conditions, with media replacement as detailed below, to form spheroids. On Day 7, the resulting spheroids were dissociated into single cells by enzymatic dissociation with Accutase™, and the cells were plated as monolayers at a concentration of 800,000 cells/cm$^2$ on plates coated with a Laminin-511 E8 fragment for the remainder of culture, and further supplemented with nutrients and small molecules as described below.

A schematic of the exemplary non-adherent differentiation protocol is shown in FIG. 1 and Table E1, which depict the small molecule compounds that were added at various days during the differentiation method. From Days 0 to 10, cells were cultured in the basal induction media, which was formulated to contain Neurobasal™ media and DMEM/F12 media at a 1:1 ratio (and with N-2 and B27 supplements, non-essential amino acids (NEAA), GlutaMAX™, L-glutamine, β-mercaptoethanol, and insulin), and supplemented with the appropriate small molecule compound(s). From Day 11 up to harvest, e.g., at Day 16, cells were cultured in a "maturation media" (Neurobasal™ media containing N-2 and B27 supplements, non-essential amino acids (NEAA), and GlutaMAX™), and supplemented with the appropriate small molecule compound(s). The basal induction media also included a serum replacement.

TABLE E1

| Differentiation Protocol | | | | | | | | |
|---|---|---|---|---|---|---|---|---|
| Day | Media | Small Molecules | | | | | | |
| 0* | Basal Induction | 5% S | LDN | SB | | | | ROCKi |
| 1 | Basal Induction | 5% S | LDN | SB | SHH | PUR | CHIR | |
| 2 | Basal Induction | 2% S | LDN | SB | SHH | PUR | CHIR | |
| 3 | Basal Induction | 2% S | LDN | SB | SHH | PUR | CHIR | |
| 4 | Basal | 2% S | LDN | SB | SHH | PUR | CHIR | |

TABLE E1-continued

| Differentiation Protocol | | | | | | | | | |
|---|---|---|---|---|---|---|---|---|---|
| Day | Media | Small Molecules | | | | | | | |
| | Induction | | | | | | | | |
| 5 | Basal Induction | 2% S | LDN | | SHH | PUR | CHIR | | |
| 6 | Basal Induction | 2% S | LDN | | SHH | PUR | CHIR | | |
| 7* | Basal Induction | 2% S | LDN | | | | CHIR | ROCKi | |
| 8 | Basal Induction | 2% S | LDN | | | | CHIR | | |
| 9 | Basal Induction | 2% S | LDN | | | | CHIR | | |
| 10 | Basal Induction | 2% S | LDN | | | | CHIR | | |
| 11 | Maturation | | BDNF | GDNF | ascorbic | dbcAMP | CHIR | TGFβ3 | DAPT |
| 12 | Maturation | | BDNF | GDNF | ascorbic | dbcAMP | CHIR | TGFβ3 | DAPT |
| 13 | Maturation | | BDNF | GDNF | ascorbic | dbcAMP | | TGFβ3 | DAPT |
| 14 | Maturation | | BDNF | GDNF | ascorbic | dbcAMP | | TGFβ3 | DAPT |
| 15 | Maturation | | BDNF | GDNF | ascorbic | dbcAMP | | TGFβ3 | DAPT |
| 16 | Maturation | | BDNF | GDNF | ascorbic | dbcAMP | | TGFβ3 | DAPT |
| 17 | Maturation | | BDNF | GDNF | ascorbic | dbcAMP | | TGFβ3 | DAPT |

S: Serum replacement;
LDN: LDN193189;
SB: SB431542;
SHH: recombinant mouse Sonic Hedgehog (rmSHH);
PUR: Purmorphamine;
CHIR: CHIR99021;
ROCKi: Y-27632;
BDNF: recombinant human brain-derived neurotrophic factor (rhBDNF);
GDNF: recombinant human glial cell-derived neurotrophic factor (rhGDNF);
TGFβ3: recombinant human transforming growth factor beta 3 (rhTGFβ3);
dbcAMP: dibutyryl cyclic AMP;
Ascorbic: ascorbic acid;
*Indicates media supplemented with ROCK inhibitor (Y-27632)

On Day 0, the basal induction media was formulated to contain: 5% serum replacement, 0.1 μM LDN (1×), 10 μM SB (1×), and 10 μM of the ROCK inhibitor Y-27632. On Day 1, basal induction media was formulated to contain: 5% serum replacement, 0.2 μM LDN (2×), 20 μM SB (2×), 0.2 μg/mL SHH (2×), 4 μM PUR (2×), and 2 μM of the GSK3β inhibitor CHIR99021, and was added by a 50% media exchange. Since the basal induction media added on Days 1 through 6 were added by a daily 50% media exchange, the concentrations of small molecules LDN, SHH, and PUR in the basal induction media were doubled (2×) on Days 1 to 6 as compared to if a complete replacement of media was performed, and the concentration of small molecule SB was doubled (2×) on Days 1 to 4, as compared to if a complete replacement of media was performed. Also, the basal induction media on Days 2 to 6 was formulated to contain 2% serum replacement and 4 μM CHIR99021. Accordingly, the basal induction media formulated for Days 2 to 4 contained 2% serum replacement, 0.2 μM LDN, 20 μM SB, 0.2 μg/mL SHH, 4 μM PUR, and 4 μM CHIR99021, and the basal induction media formulated for Days 5 and 6 contained 2% serum replacement, 0.2 μM LDN, 0.2 μg/mL SHH, 4 μM PUR, and 4 μM CHIR99021.

The cells were transferred to substrate-coated plates on Day 7, as described above, using a basal induction media that was formulated to contain: 2% serum replacement, 0.1 μM LDN, 2 μM CHIR99021, and 10 μM Y-27632. The media was completely replaced daily from Days 8 to 10, with basal induction media formulated to contain 2% serum replacement, 0.1 μM LDN, and 2 μM CHIR99021.

Starting on Day 11, the media was switched to maturation media formulated to contain: 20 ng/mL BDNF, 0.2 mM ascorbic acid, 20 ng/mL GDNF, 0.5 mM dbcAMP, and 1 ng/mL TGFβ3 (collectively, "BAGCT"), 10 μM DAPT, and 2 μM CHIR99021. The media was completely replaced on Day 12 with the same media formulation containing the same concentrations of small molecule compounds as on Day 11. From Day 13 until harvest, the media was replaced every day with maturation media formulated to contain BAGCT and DAPT (collectively, "BAGCT/DAPT") at the same concentrations as on Days 11 and 12.

Cells were harvested on Day 16.

B. Example 2: Comparative Analysis of Neuronal Differentiation Methods

The neuronal differentiation method as described in Example 1 was compared with an adherent neuronal differentiation method and three alternative non-adherent neuronal differentiation methods.

iPSCs were created from fibroblasts obtained from human donors with Parkinson's disease and subjected to each of these five neuronal differentiation methods through at least Day 10 for comparative purposes.

The adherent neuronal differentiation method (also referred to herein as "2D adherent culture") involved culturing the iPSCs in mTeSR1 based media until they reached approximately 75-90% confluence. The iPSCs were then washed with sterile PBS and detached from the 6-well plates by enzymatic dissociation with Accutase™. On Day −1, the cells were seeded at approximately 300,000 cells/$cm^2$ with 10 μM of the ROCK inhibitor Y-27632 overnight, with $2.9e^6$ cells per well of a 6-well plate in mTeSR1 based media. The cells were then cultured in a basal induction media containing the components as shown in Table E2, below, beginning on Day 0 for each of the enumerated days through Day 10.

The media was completed replaced each of Days 0 through 10 with the media as shown in Table E2. The basal induction media contained, when indicated: LDN at a concentration of 0.1 μM LDN; SB at a concentration of 10 μM SB; SHH at a concentration of 0.1 μg/mL; and PUR at a concentration of 2 μM.

TABLE E2

| 2D Adherent Culture | | | | | | | | |
|---|---|---|---|---|---|---|---|---|
| Day | Media | Small Molecules | | | | | | |
| −1 | mTeSR1 | | | | | | | ROCKi |
| 0 | Basal Induction | 5% S | LDN | SB | | | | |
| 1 | Basal Induction | 5% S | LDN | SB | SHH | PUR | | |
| 2 | Basal Induction | 2% S | LDN | SB | SHH | PUR | CHIR | |
| 3 | Basal Induction | 2% S | LDN | SB | SHH | PUR | CHIR | |
| 4 | Basal Induction | 2% S | LDN | SB | SHH | PUR | CHIR | |
| 5 | Basal Induction | 2% S | LDN | | SHH | PUR | CHIR | |
| 6 | Basal Induction | 2% S | LDN | | SHH | PUR | CHIR | |
| 7 | Basal Induction | 2% S | LDN | | | | CHIR | |
| 8 | Basal Induction | 2% S | LDN | | | | CHIR | |
| 9 | Basal Induction | 2% S | LDN | | | | CHIR | |
| 10 | Basal Induction | 2% S | LDN | | | | CHIR | |

S: Serum replacement;
LDN: LDN193189;
SB: SB431542;
SHH: recombinant mouse Sonic Hedgehog (rmSHH);
PUR: Purmorphamine;
CHIR: CHIR99021;
ROCKi: Y-27632

The non-adherent neuronal differentiation method as described in Example 1 (also referred to as "3D) Condition 2") was performed in addition to three alternative non-adherent methods (referred to as "3D) Condition 1," "3D) Condition 3," and 3D Condition 4") that were each performed using the same method as 3D Condition 2 except for the differences as indicated in Table E3, below. Specifically, each of 3D Conditions 1, 2, 3, and 4 are the same except for differences in the small molecules contained in the basal induction media on Day 0 and Day 1. The basal induction media of Day 2 and beyond for each of 3D Conditions 1, 2, 3, and 4 was the same, thereby resulting in the same methodology and media used except for Days 0 and 1, as shown in Table E3. In particular, the basal induction media of 3D Condition 1 prepared for Day 1 did not contain CHIR until Day 2, whereas the basal induction media of 3D Conditions 2 and 3 prepared for Day 1 each contained CHIR at a different concentration (2 μM for 3D Condition 2; and 4 μM for 3D Condition 3). The basal induction media for 3D Condition 4 that was prepared for Day 0 further included SHH, PUR, and CHIR at the indicated concentrations. 3D Condition 4 is the non-adherent neuronal differentiation method as described in Example 1 of WO2021/146349.

TABLE E3

| Conditions of D0 and D1 Basal Induction Media for 3D Conditions 1, 2, 3, and 4 | | |
|---|---|---|
| Condition | Day 0 | Day 1 |
| 3D Condition 1 | 5% serum replacement<br>LDN (0.1 μM)<br>SB (10 μM) | 5% serum replacement<br>LDN (0.2 μM)<br>SB (20 μM)<br>SHH (0.2 μg/mL)<br>PUR (4 μM) |
| 3D Condition 2 | 5% serum replacement<br>LDN (0.1 μM)<br>SB (10 μM) | 5% serum replacement<br>LDN (0.2 μM)<br>SB (20 μM)<br>SHH (0.2 μg/mL)<br>PUR (4 μM)<br>CHIR (2 μM) |
| 3D Condition 3 | 5% serum replacement<br>LDN (0.1 μM)<br>SB (10 μM) | 5% serum replacement<br>LDN (0.2 μM)<br>SB (20 μM)<br>SHH (0.2 μg/mL)<br>PUR (4 μM)<br>CHIR (4 μM) |
| 3D Condition 4 | 5% serum replacement<br>LDN (0.1 μM)<br>SB (10 μM)<br>SHH (0.1 μg/mL)<br>PUR (2 μM)<br>CHIR (2 μM) | 5% serum replacement<br>LDN (0.2 μM)<br>SB (20 μM)<br>SHH (0.2 μg/mL)<br>PUR (4 μM)<br>CHIR (4 μM) |

Cells were differentiated in accordance with each of the five differentiation methods and were analyzed at days including Day 7 and Day 10 for expression of various markers.

Figure 2:
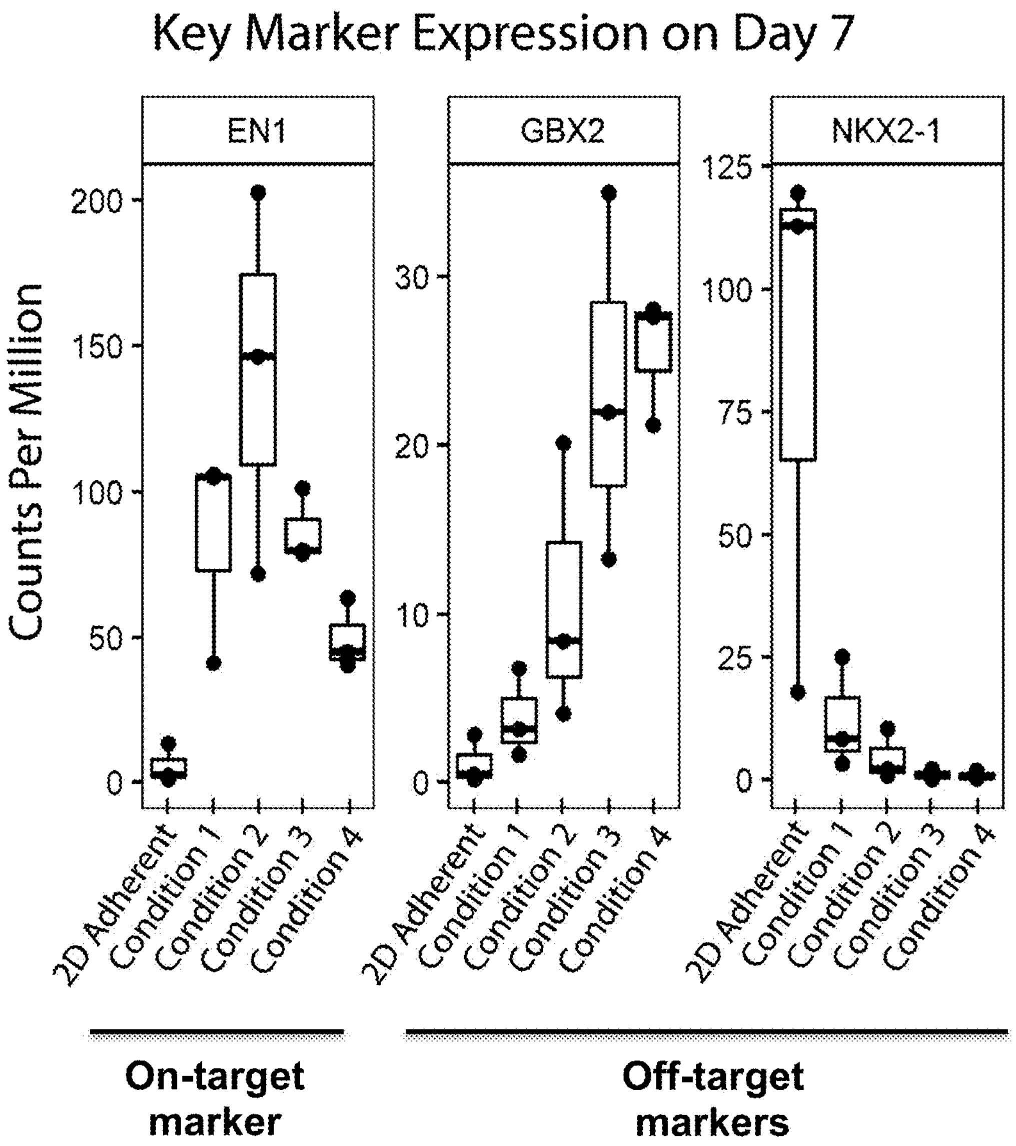
FIG. 2 shows EN1, GBX2, and NKX2-1 marker expression (counts per million) in Day 7 cells cultured using each of the following methods: 2D adherent culture, 3D Condition 1, 3D Condition 2, 3D Condition 3, and 3D Condition 4.

EN1 is a midbrain dopaminergic lineage marker. Expression levels of the EN1 dopaminergic lineage marker were compared between cells generated from each of the five differentiation methods at Day 7. As shown in FIG. 2, the cells cultured using the 2D adherent culture method exhibited very low EN1 expression on Day 7, and the lowest among all five methods tested, whereas the cells cultured using 3D Condition 2 exhibited the highest expression of EN1 on Day 7 of all five differentiation methods, and was nearly three times higher on average than when the cells were cultured with 3D Condition 4.

GBX2 and NKX2-1 are off-target non-dopaminergic lineage markers. As shown in FIG. 2, on Day 7, expression of the GBX2 marker is relatively low for all five differentiation methods, as the average counts per million is below 30 for each of the methods, and expression of the NKX2-1 marker is also very low (under 30 counts per million) for all four non-adherent methods (3D Conditions 1, 2, 3, and 4). Surprisingly, the non-adherent methods (3D Conditions 1, 2, 3, and 4) exhibit considerably less NKX2-1 marker expression on Day 7 than the 2D adherent culture method (approximately 10-fold less on average), thereby demonstrating the superior ability of the non-adherent methods, including 3D Condition 2, to preferentially promote a dopaminergic lineage fate.

LMX1A is a ventral midbrain marker indicative of dopaminergic lineage fate. As shown in FIGS. 3A and 3B, on Day 10, expression of LMX1A in cells cultured in 3D Conditions 1 and 2 was similar to expression of LMX1A in cells cultured in the 2D adherent culture, which were all higher than the expression of LMX1A in cells cultured in 3D Conditions 3 and 4.

Collectively, this data demonstrates that 3D Condition 2 is superior with regards to promoting a dopaminergic lineage fate early on in the differentiation process, as compared to the 2D adherent culture method and the three alternative non-adherent methods (3D Conditions 1, 3, and 4), which includes 3D Condition 4 in which the cells are exposed to LDN, SB, SHH, PUR, and CHIR beginning on Day 0.

Figure 5:
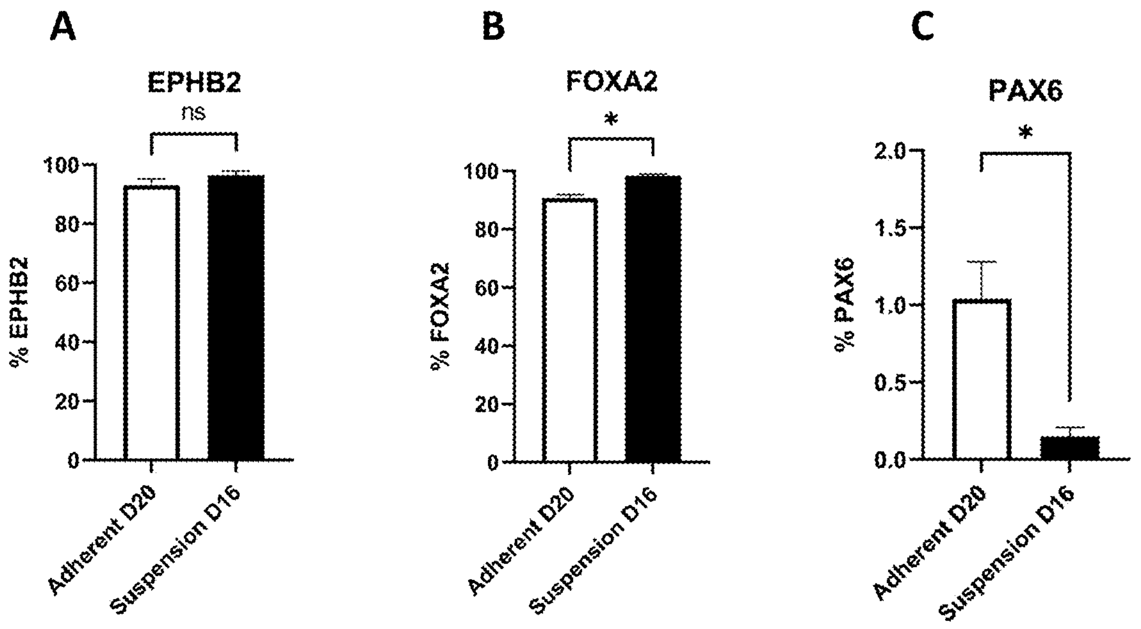
FIG. 5 shows flow cytometry measurements of key lineage markers in dopaminergic progenitor cells obtained using adherent and suspension culture methods (n=4). Adherent cultured cells were harvested at Day 20, while suspension culture cells were harvested at Day 16. EphB2, a pan-neuronal marker, shows no difference between cells obtained using adherent and suspension culture techniques (FIG. 5A). FOXA2 expression is characteristic of floorplate lineage in brain development and suspension culture increased expression of FOXA2 compared to adherent culture via flow cytometry pointing towards a more accurate ventral midbrain dopaminergic neuronal cell fate (*$p<0.05$) (FIG. 5B). PAX6 expression is characteristic of forebrain lineage in brain development, and flow cytometry shows roughly a 10-fold decrease in PAX6 for suspension culture cells compared to adherent culture cells (*$p<0.05$)(FIG. 6C). Error bars are shown as the standard error of the mean (S.E.M.).

FIG. 5 shows a comparison of marker expression by neuronal cells produced using adherent cell culture versus the Day 1 suspension culture protocol described herein. The Day 1 suspension culture cells were harvested on Day 16, while the adherent cultured cells were harvested on Day 20. FIG. 5A shows expression of the pan-neuronal marker EPHB2, which is indicative of the neuronal cell lineage in general. Similar levels of EPHB2 were expressed by neuronal cells obtained using adherent and suspension culture, indicating that both differentiation protocols produce neuronal progenitor cells. FIG. 5B shows expression of FOXA2, which is characteristic of the floorplate lineage in brain development. The desired dopaminergic neuronal progenitor cells are of the floorplate lineage. Neuronal cells obtained using the cell suspension culture method exhibited higher FOXA2 expression than neuronal cells produced using adherent culture, thereby demonstrating that the suspension culture differentiation protocol more accurately directs cells towards the desired ventral midbrain dopaminergic neuronal cell fate. FIG. 5C shows a comparison of PAX6 expression by cells produced using adherent culture versus cells produced using the suspension culture protocol. PAX6 expression of the forebrain lineage in brain development. Cells produced using the suspension culture differentiation method exhibited an approximately 10-fold decrease in PAX6 expression compared to cells produced using adherent culture, thereby providing further confirmation that that the suspension culture differentiation method more accurately directs differentiation towards the desired ventral midbrain dopaminergic neuronal cell fate.

Figure 6:
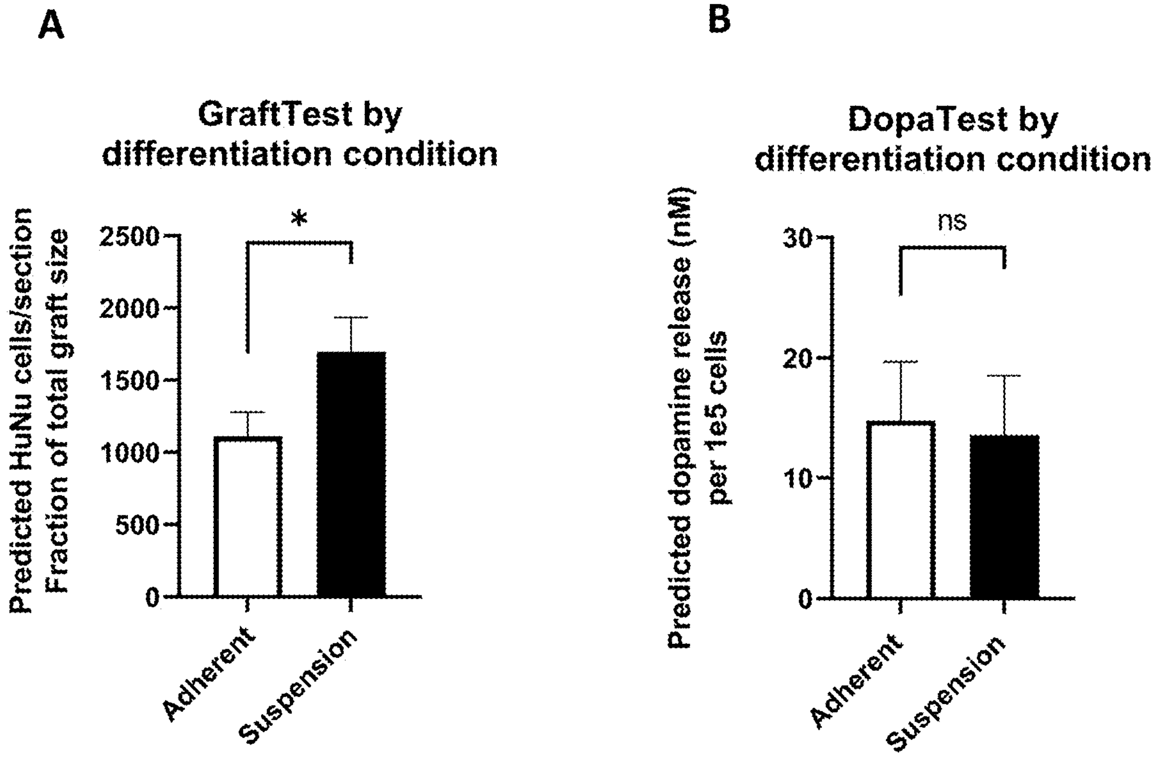
FIG. 6A shows predicted graft size, after implantation into a subject brain, of neuronal cells derived from obtained from neuronal progenitor cells obtained from adherent culture and suspension culture. Graft size predictions were estimated across donor backgrounds (n=4). Across all donors, graft sizes were predicted to be larger under suspension culture conditions. When grouped by culture condition, suspension culture was associated with significantly greater predicted graft sizes (*=$p<0.05$). Error bars are shown as the standard error of the mean (S.E.M.).
FIG. 6B shows estimated dopamine release, after implantation into a subject brain, by neuronal cells derived from the neuronal progenitor cells obtained using the adherent culture and suspension culture protocols. When grouped by culture condition, there was no significant difference in predicted dopamine release across differentiation conditions ($p>0.05$). Error bars are shown as the standard error of the mean (S.E.M.).

Cells obtained using the "Day 1" suspension culture differentiation method described herein were then compared to cells produced using the adherent culture differentiation protocol for predicted graft size and dopamine production after the cells are implanted into a subject brain. The Day 1 suspension culture cells were harvested on Day 16, while the adherent cultured cells were harvested on Day 20. Predicted graft sizes were obtained GraftTest™, which is an in silico predictive tool that uses bulk RNAseq data to estimate graft size (number of human nuclei in a rodent brain hemisphere). GraftTest is described in U.S. Provisional Application No. 63/598,533 entitled "METHODS OF PREDICTING CHARACTERISTICS OF DIFFERENTIATED NEURONAL CELLS," filed Nov. 13, 2023. The model was trained on graft features (human nuclei) that were measured after the precursor cells had engrafted and matured in the rodent brain for 21 days. Importantly, predictions are underestimates of the total graft size since models were trained on cell counts found in one sixth of the total graft volume in each hemisphere. Each estimate represents the mean of several hemispheres. Training data typically included estimates based on four to five rodents and two hemispheres per rodent. FIG. 6A shows that dopaminergic neuronal progenitor cells produced using the suspension culture differentiation method are predicted to produce significantly larger grafts after implantation than neuronal progenitor cells produced using the adherent culture differentiation method.

Predicted dopamine release levels after implantation for cells produced using the Day 1 suspension culture differentiation method compared to cells produced using the adherent culture differentiation protocol are shown in FIG. 6B. The Day 1 suspension culture cells were harvested on Day 16, while the adherent cultured cells were harvested on Day 20. The predicted dopamine release levels were obtained using DopaTest™, which is an in silico predictive tool that uses bulk RNAseq data to estimate the quantity of dopamine released by cells after extended culture. DopaTest is described in U.S. Provisional Application No. 63/598,533. In the training data set, dopamine was quantified using Liquid Chromatography Mass Spectrometry (LCMS) and transcriptome features at the precursor focal timepoint were used to train the model. Predictions of dopamine release therefore represent a measure of expected cell performance after extended culture. Dopamine release estimates are based on predicted dopamine production (nM) of 1e5 mature dopaminergic neuron cells. As shown in FIG. 6B, predicted dopamine release levels were not significantly different for cells produced using Day 1 suspension culture versus cells produced using the adherent culture method.

Figure 7:
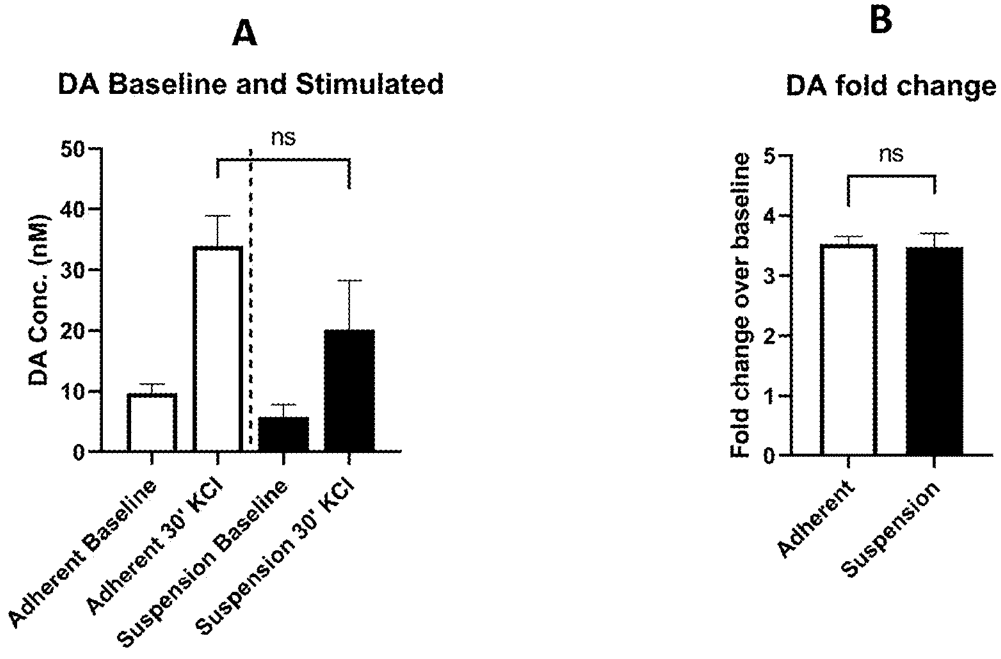
FIG. 7A shows a graph comparing dopamine concentration of the supernatant in nM at the baseline timepoint and after a 30 minute KCl treatment for both adherent and suspension culture protocols, without normalization. There is no significant difference in the raw dopamine release between the adherent and suspension culture protocols (n.s. $p>0.05$)
FIG. 7B shows the fold change of dopamine release into the supernatant upon stimulation compared to dopamine release at baseline. There is no significant difference between adherent and suspension culture protocols (n.s. $p>0.05$). Error bars are shown as the standard error of the mean (S.E.M.). n=4 for all plots.

Liquid Chromatography Mass Spectrometry (LCMS) was used to compare dopamine and serotonin release by cells obtained using the Day 1 suspension culture differentiation method were compared to those produced using adherent culture. The Day 1 suspension culture cells were harvested on Day 16, while the adherent cultured cells were harvested on Day 20. Cells were then cultured for 60 days in a defined neuronal maturation media. On the day of collection, cells were rinsed once with warm Hank's balanced salt solution (HBSS), then incubated in HBSS for 15 minutes at 37 deg. Celsius. Samples were collected after 15 minutes in triplicates to establish baseline neurotransmitter release. Cells were then incubated at 37 deg Celsius in a 56 mM potassium chloride (KCl) solution in HBSS to induce neurotransmitter release. Samples were collected in triplicate at the 30' timepoint. FIG. 7A shows dopamine concentration of the supernatant (nM) at baseline and after a 30 minute KCl treatment for both adherent and suspension culture protocols, without normalization (n=4). There was no significant difference in the raw dopamine release between differentiation conditions (n.s. $p>0.05$). FIG. 7B shows the fold change of the dopamine release upon stimulation to dopamine release at baseline. There was no significant difference in the raw dopamine release between the adherent and suspension culture protocols (n.s. $p>0.05$). Error bars are shown as the standard error of the mean (S.E.M.). n=4 for all plots.

Figure 8:
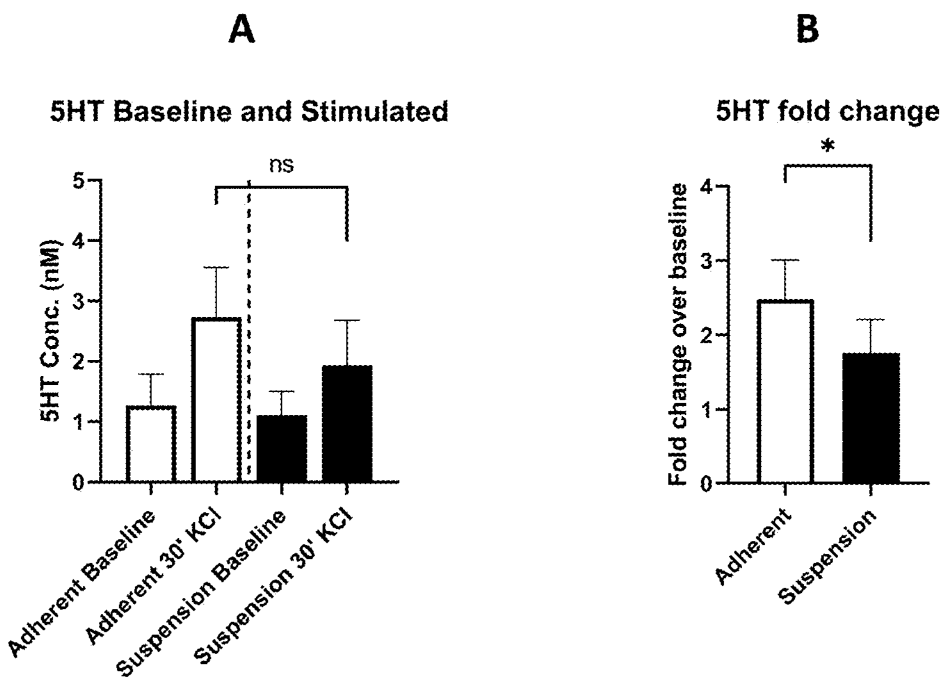
FIG. 8A shows serotonin concentration of the supernatant (nM) at baseline and 30-minute KCl treatment for both adherent and suspension culture protocols, without normalization (n=4). There was no significant difference in the raw serotonin release between the adherent and suspension culture protocols (n.s. $p>0.05$).
FIG. 8B shows the fold change of serotonin release upon stimulation compared to baseline, demonstrating a significant decrease in serotonin production by dopaminergic neuronal progenitor cells produced using the suspension culture condition compared to cells produced using adherent culture (n=4)(*$p<0.05$). Thus, cells generated using the suspension culture produce similar amounts of dopamine while producing less serotonin than cells from the adherent condition. Error bars are shown as the standard error of the mean (S.E.M.). n=4 for all plots. 5HT=5-hydroxy tryptamine (serotonin).

FIG. 8A shows serotonin concentration of the supernatant (nM) at baseline and after a 30-minute KCl treatment for both adherent and suspension culture protocols, without normalization (n=4). There was no significant difference in the raw serotonin release between the adherent and suspension culture protocols (n.s. $p>0.05$). FIG. 8B shows normalization of serotonin release upon KCl stimulation compared to baseline. The data show that there is a significant decrease in serotonin (5HT) production by cells produced using the Day 1 suspension culture differentiation method compared to cells produced using the adherent culture differentiation method (n=4)(*$p<0.05$). Error bars are shown as the standard error of the mean (S.E.M.). These results demonstrate that the Day 1 suspension culture differentiation method yields cells that have an enhanced safety profile compared to cells produced using adherent cell culture.

Figure 9:
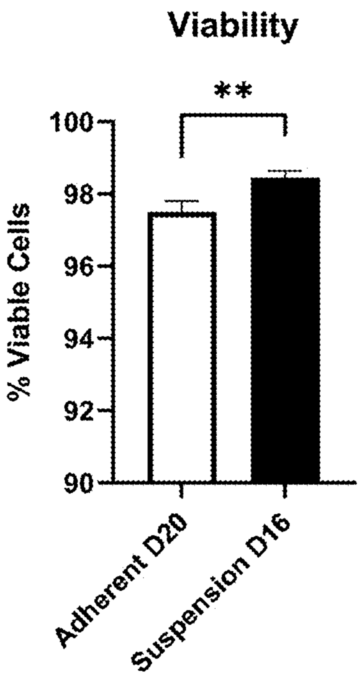
FIG. 9 shows cell viability for dopaminergic neuronal progenitor cells produced using suspension culture compared to those produced using adherent as determined using the "cell count and viability" protocol on a Nucleocounter NC-200 (n=4). Cells generated using the suspension culture condition showed a significant increase in percentage of viable cells (**$p<0.01$).

We then compared viability of cells produced using the Day 1 suspension culture differentiation method to that of cells produced using the adherent cell culture differentiation method. The Day 1 suspension culture cells were harvested on Day 16, while the adherent cultured cells were harvested on Day 20. Cell viability was tested by running the "cell count and viability" protocol on the Nucleocounter NC-200. Cells were generated either using the adherent or suspension culture conditions (n=4). Cells generated using the Day 1 suspension culture condition showed a significant increase in percentage of viable cells as shown in FIG. 9.

Figure 10:
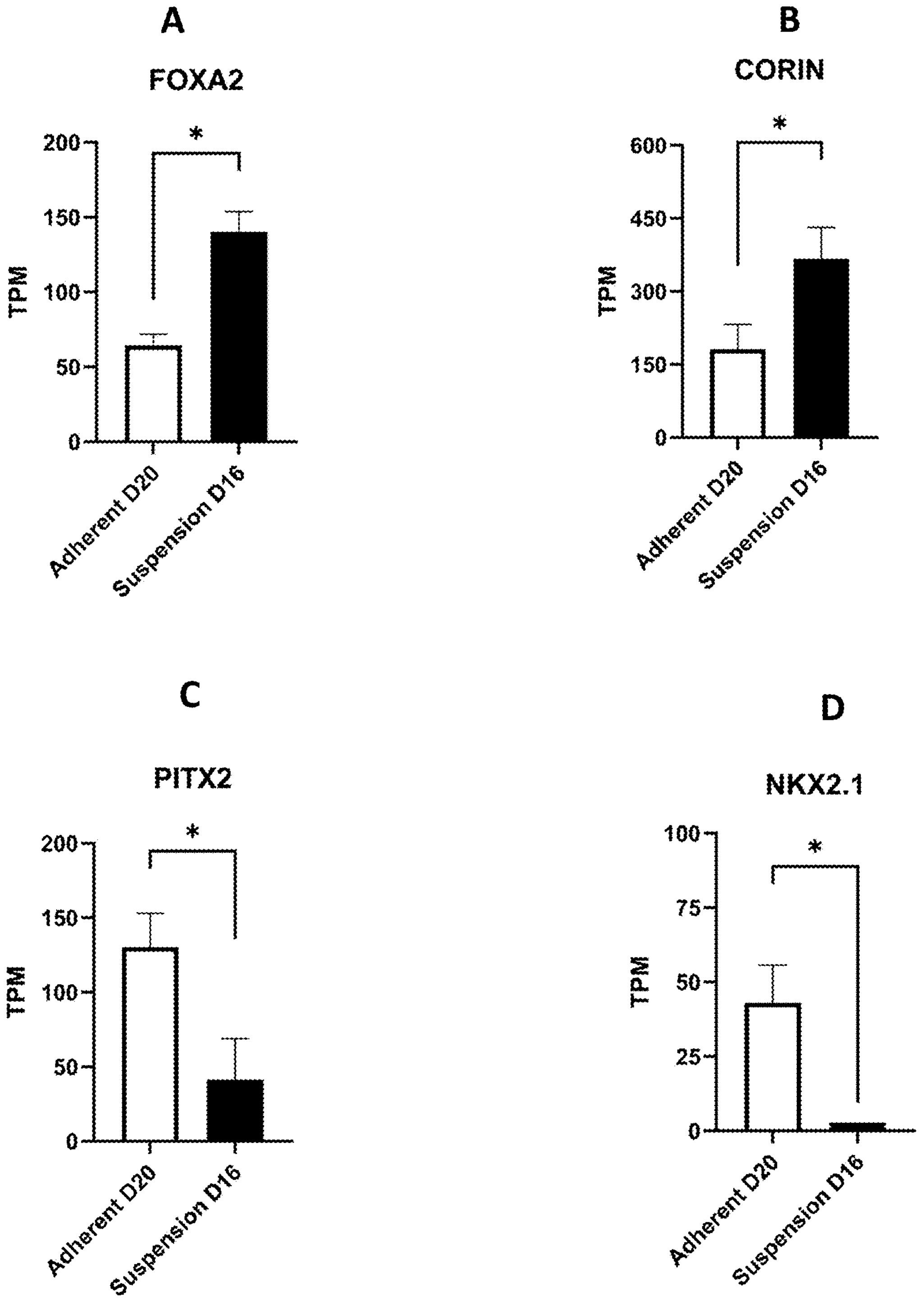
FIG. 10 shows expression of two "on target" markers FOXA2 (FIG. 10A) and CORIN (FIG. 10B) for which increased expression is indicative of dopaminergic neuronal progenitor cells, and two "off target" markers PITX2 (FIG. 10C) and NKX2.1 (FIG. 10D) for which increased expression is not characteristic of dopaminergic neuronal progenitor cells. The data in this figure thus demonstrate that the cells produced using the Day 1 suspension culture differentiation protocol disclosed herein are more characteristic of dopaminergic neuronal progenitor cells than cells produced using a differentiation protocol in which both the first and the second incubations are performed in adherent culture.

Cells produced using the Day 1 suspension culture differentiation method were compared to those produced using adherent cell culture differentiation with respect to expression of two "on-target" markers and two "off-target" markers. The Day 1 suspension culture cells were harvested on Day 16, while the adherent cultured cells were harvested on Day 20. RNAseq analysis shows that cells produced using the Day 1 suspension culture method exhibited higher levels of "on target" FOXA2 (FIG. 10A) and CORIN expression (FIG. 10B) than cells produced using the adherent method, thereby indicating that the Day 1 suspension culture cells are more characteristic of the desired dopaminergic neuronal progenitor cells than are cells produced using adherent culture. Cells produced using the Day 1 suspension culture method also expressed significantly less of the "off-target" markers PITX2 (FIG. 9C) and NKX2.1 (FIG. 9D), providing further evidence that the Day 1 suspension culture differentiation method produces cells that are more accurately directed to the desired dopaminergic neuronal progenitor cell type.

C. Example 3: Analysis of Differentiation Time Using Adherent vs. Non-Adherent Differentiation Methods The results obtained in Example 2 suggest that differentiating iPSCs using non-adherent conditions, such as described in Example 1, advantageously allows for an accelerated timeline for differentiating the iPSCs into determined dopaminergic progenitor cells and/or committed dopaminergic progenitor cells. To confirm this, a study was conducted where iPSCs were differentiated using the non-adherent method as described in Example 1 (also referred to in this example as the "3D-differentiated samples"), and harvested on Day 16, and gene expression data from those cells was compared to gene expression data obtained from cells differentiated using the 2D adherent culture method of Example 2 and harvested on Days 17, 18, 19, 20, 21, 22, and 25 (also referred to in this example as the "2D-differentiated" samples). The 2D adherent culture method included culturing the cells through Day 10 as described in Example 2, and beginning on Day 11 through harvest were cultured using the maturation media as described in Example 1. The cells cultured using the 2D adherent culture method were passaged on Day 16 and, if applicable, Day 20, in the maturation media that further included the ROCK inhibitor.

Relative transcriptome maturity of cell preparations was assessed via a supervised principal components analysis (PCA). The gene set that was used in the transcriptome maturity test was identified in a differentiation time course experiment on 2D-differentiated dopamine neuron precursor cells (DANPCs) using the 2D adherent culture method described above. Briefly, n=12 independent DANPCs were assayed by bulk RNAseq at each of seven timepoints corresponding with Day 17, Day 18, Day 19, Day 20, Day 21, Day 22, and Day 25 of differentiation (training set). Genes whose expression was statistically associated with monotonic change over the time course were identified using the edgeR library (Robinson et al., Bioinformatics, 2009, 26(1): 139-140), implemented in R (R Core Team, R: A language and environment for statistical computing, 2021, R Foundation for Statistical Computing, Vienna, Austria). The top 50 statistically p-value-ranked down-regulating genes were used as the gene set for the supervised PCA. The first principal component (PC1) in the training set explains ~85.8% of the variance in gene expression in the maturity gene set and is henceforth used as a proxy of relative transcriptome maturity. Cell preparations with higher PC1 scores are associated with more mature transcriptomes, and vice versa.

The test set was composed of n=15 3D-differentiated samples that were differentiated using the non-adherent method as described in Example 1, assayed via bulk RNAseq on Day 16. The test set transcriptomes were ordinated using the trained supervised PCA (above) and predicted PC1 values were aligned and compared to the training set (see FIG. 4).

As shown in FIG. 4, all 16 3D-differentiated samples using the non-adherent method as described in Example 1 contained transcriptomes that were, on average, more mature than the mean maturity of the 2D-differentiated training set at Day 20 using the 2D adherent culture method described above. Fifteen out of sixteen (93.8%) 3D-differentiated samples were within the upper bound of 1.96× standard deviations of the mean of Day 20 2D-differentiated cells. One 3D-differentiated sample was outside of this range and was more consistent with a Day 21-22 sample. Most Day 16 3D-differentiated samples overlapped the Day 21 2D-differentiated training set PC1 distribution.

This data demonstrates that differentiating iPSCs using the non-adherent "Day 1" suspension culture method of Example 1 is able to accelerate the differentiation timeline of iPSC-derived determined dopaminergic neuronal progenitor cells and/or committed dopaminergic neuronal progenitor cells as compared to other methods, such as the 2D adherent culture method. This is advantageous in several ways, particularly relating to manufacturing since this can reduce the amount of time and resources needed to produce iPSC-derived determined dopaminergic neuronal progenitor cells and/or committed dopaminergic neuronal progenitor cells that are suitable for therapeutic use.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

What is claimed is:

1. A method of differentiating pluripotent stem cells into dopaminergic neuronal progenitor cells, the method comprising:

a) performing a first incubation comprising non-adherently culturing pluripotent stem cells in a first multiwell culture vessel under conditions to produce a cellular spheroid, wherein the first incubation comprises:

(i) exposing the pluripotent stem cells to at least one inhibitor of TGF-β/activin-Nodal signaling and at least one inhibitor of bone morphogenetic protein (BMP) signaling for at least one day, wherein Day 0 is the first day on which the pluripotent stem cells are exposed to the inhibitor of TGF-β/activin-Nodal signaling and the inhibitor of bone morphogenetic protein (BMP) signaling, in the absence of: x) an activator of Sonic Hedgehog (SHH) signaling, and y) an inhibitor of glycogen synthase kinase 3ß (GSK3ß) signaling; and (ii) starting on Day 1 of the first incubation, wherein Day 1 is one day after the first day that the pluripotent stem cells are first exposed to the inhibitor of TGF-β/activin-Nodal signaling and the inhibitor of bone morphogenetic protein (BMP) signaling, exposing the cells obtained from step (i) to at least one activator of Sonic Hedgehog (SHH) signaling and at least one inhibitor of glycogen synthase kinase 3β (GSK3β) to produce the cellular spheroid; and b) performing a second incubation comprising adherently culturing cells of the spheroid in a second culture vessel under conditions to further differentiate the cells into dopaminergic neuronal progenitor cells;

wherein the dopaminergic neuronal progenitor cells exhibit increased expression of FOXA2 and CORIN and decreased expression of NKX2.1 and PITX2 compared to cells differentiated in a method that comprises performing the first incubation in adherent culture.

2. The method of claim 1, wherein the pluripotent stem cells are induced pluripotent stem cells.

3. The method of claim 1, wherein the pluripotent stem cells are autologous to a subject to be treated with the dopaminergic neuronal progenitor cells.

4. The method of claim 1, wherein the first incubation further comprises exposing the pluripotent stem cells to a ROCK inhibitor (ROCKi) starting on Day 0.

5. The method of claim 4, wherein the pluripotent stem cells were not exposed to a ROCKi prior to exposing the pluripotent stem cells to the inhibitor of TGF-β/activin-Nodal signaling and the inhibitor of bone morphogenetic protein (BMP) signaling in the first incubation.

6. The method of claim 1, wherein the method comprises exposing the pluripotent stem cells to:

a) the inhibitor of TGF-β/activin-Nodal signaling beginning on Day 0 and through Day 4;

b) the inhibitor of BMP signaling beginning on Day 0 and through Day 10;

c) the activator of Sonic Hedgehog signaling beginning on Day 1 and through Day 6; and d) the inhibitor of glycogen synthase kinase 3ß (GSK3B) signaling beginning on Day 1 and through Day 12.

7. The method of claim 1, wherein the inhibitor of BMP signaling is LDN193189.

8. The method of claim 7, wherein the cells are exposed to LDN193189 at a concentration of between 10 nM and 500 nM, between 20 nM and about 400 nM, between 50 nM and 200 nM, or between 75 nM and 150 nM, optionally 100 nM.

9. The method of claim 1, wherein the inhibitor of TGF-β/activin-Nodal signaling is SB431542.

10. The method of claim 9, wherein the cells are exposed to SB431542 at a concentration of between 1 μM and 20 μM, between 5 μM and 15 μM, or between 8 μM and 12 μM, optionally 10 μM.

11. The method of claim 1, wherein the activator of SHH signaling is SHH or purmorphamine.

12. The method of claim 11, wherein the cells are exposed to SHH at a concentration of between 10 ng/mL and 500 ng/mL, between 20 ng/ml and 400 ng/mL, between 50 ng/mL and 200 ng/mL, or between 75 ng/mL and about 150 ng/mL, about 100 ng/mL.

13. The method of claim 11, wherein the cells are exposed to purmorphamine at a concentration of between 0.1 μM and 20 μM, between 0.5 μM and 10 μM, between 1 μM and about 5 μM, between 1 μM and 3 μM, or between 1.5 μM and 2.5 μM, optionally at 2 μM.

14. The method of claim 1, wherein the inhibitor of GSK3β signaling is CHIR99021.

15. The method of claim 14, wherein the cells are exposed to CHIR99021 at a concentration of between 0.1 μM and 5 μM, between 0.5 μM and 4 μM, between 0.5 UM and 2 μM, optionally 1 μM; and on each of Days 2 through 12, the cells are exposed to CHIR99021 at a concentration of between 0.1 μM and 5 μM, between 0.5 μM and 4 μM, or between 1 μM and 3 μM, optionally 2 μM.

16. The method of claim 1, wherein the first incubation comprises a media exchange on one or more of Days 1 through 6.

17. The method of claim 16, wherein the first incubation comprises a media exchange on each of Days 1 through 6.

18. The method of claim 1, wherein the second incubation begins on Day 7.

19. The method of claim 1, wherein the cells of the spheroid are disassociated to produce a cell suspension prior to the second incubation, and cells of the cell suspension are adherently cultured in the second culture vessel.

20. The method of claim 1, wherein the second incubation comprises exposing the cells of the spheroid to an inhibitor of bone morphogenetic protein (BMP) signaling and an inhibitor of GSK3β signaling.

21. The method of claim 20, wherein the second incubation further comprises exposing the cells to (i) brain-derived neurotrophic factor (BDNF); (ii) ascorbic acid; (iii) glial cell-derived neurotrophic factor (GDNF); (iv) dibutyryl cyclic AMP (dbcAMP); (v) transforming growth factor beta-3 (TGFβ3); and (vi) an inhibitor of Notch signaling.

22. The method of claim 1, further comprising harvesting the dopaminergic neuronal progenitor cells.

23. The method of claim 22, wherein the dopaminergic neuronal progenitor cells are harvested on Day 14 or later.

24. The method of claim 22, further comprising formulating the harvested dopaminergic neuronal progenitor cells with a cryoprotectant.

25. The method of claim 24, further comprising cryopreserving the formulated harvested dopaminergic neuronal progenitor cells.

26. The method of claim 1, wherein each well of the first multiwell culture vessel comprises a plurality of microwells.

27. The method of claim 1, wherein the dopaminergic neuronal progenitor cells:

a) express Forkhead Box A2 (FOXA2) at greater than 100 transcripts per million (TPM) in bulk RNA sequencing (RNAseq) analysis;

b) express Corin, serine peptidase (CORIN) at greater than 300 TPM in bulk RNAseq analysis;

c) express Paired Like Homeodomain 2 (PITX2) at less than 50 TPM in bulk RNAseq analysis; and d) express NK2 Homeobox 1 (NKX2.1) at less than 10 TPM in bulk RNAseq analysis.

28. The method of claim 1, wherein the dopaminergic neuronal progenitor cells produce significantly less serotonin compared to cells differentiated in a method that comprises performing the first incubation in adherent culture.

* * * * *